(12) United States Patent
Li et al.

(10) Patent No.: US 7,172,764 B2
(45) Date of Patent: Feb. 6, 2007

(54) RESCUE AGENTS FOR TREATING BOTULINUM TOXIN INTOXICATIONS

(75) Inventors: Shengwen Li, Irvine, CA (US); Kei Roger Aoki, Coto de Caza, CA (US); Lance E. Steward, Irvine, CA (US); Joseph Francis, Aliso Viejo, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 10/715,810

(22) Filed: Nov. 17, 2003

(65) Prior Publication Data

US 2005/0106182 A1    May 19, 2005

(51) Int. Cl.
*A61K 39/08* (2006.01)
*C07K 14/33* (2006.01)

(52) U.S. Cl. .................. 424/239.1; 424/9.1; 424/236.1; 514/12; 530/350; 435/325; 435/69.1; 435/320.1; 536/23.7

(58) Field of Classification Search ................ 424/9.1, 424/239.1, 236.1; 514/12; 530/350; 435/325, 435/69.1, 320.1; 536/23.7
See application file for complete search history.

(56) References Cited

U.S. PATENT DOCUMENTS

| | | | |
|---|---|---|---|
| 5,437,291 A | 8/1995 | Pasricha et al. | |
| 5,670,484 A | 9/1997 | Binder | |
| 5,714,468 A | 2/1998 | Binder | |
| 5,766,605 A | 6/1998 | Sanders et al. | |
| 6,051,239 A | 4/2000 | Simpson et al. | |
| 6,063,768 A | 5/2000 | First | |
| 6,113,915 A | 9/2000 | Aoki et al. | |
| 6,139,845 A | 10/2000 | Donovan | |
| 6,143,306 A | 11/2000 | Donovan | |
| 6,203,794 B1 | 3/2001 | Dolly et al. | |
| 6,265,379 B1 | 7/2001 | Donovan | |
| 6,299,893 B1 | 10/2001 | Schwartz et al. | |
| 6,306,403 B1 | 10/2001 | Donovan | |
| 6,306,423 B1 | 10/2001 | Donovan | |
| 6,312,708 B1 | 11/2001 | Donovan | |
| 6,328,977 B1 | 12/2001 | Donovan | |
| 6,358,513 B1 | 3/2002 | Voet et al. | |
| 6,365,164 B1 | 4/2002 | Schmidt | |
| 6,395,277 B1 | 5/2002 | Graham | |
| 6,423,319 B1 | 7/2002 | Brooks et al. | |
| 6,458,365 B1 | 10/2002 | Aoki et al. | |
| 6,464,986 B1 | 10/2002 | Aoki et al. | |

FOREIGN PATENT DOCUMENTS

WO    WO02/089834    11/2002

OTHER PUBLICATIONS

Park and Simpson, "Inhalational poisoning botulinium toxin and inhalation vaccination with its heavy-chain component," Infect. Immun. (2003) 71:1147-1154.

Atassi and Oshima, "Structure, activity and immune (T and B cell) recognition of botulinum neurotoxins," Crit. Rev. Immunol. (1999) 19:219-260.

Marchese Ragona, et al., "Management of parotid sialocele with botulinum toxin," The Laryngoscope (1999) 109:1344-1346.

Wiegand, et al., "125-I labelled botulinum A neurotoxin: pharmacokinetics in cats after intramuscular injection," Naunyn-Schmiedeberg's Arch. Pharmacol. (1976) 292:161-165.

Habermann, "125-I labeled neurotoxin from Clostridium botulinum A: preparation, binding to synaptosomes and ascent to the spinal cord," Naunyn-Schmiedeberg's Arch. Pharmacol. (1974) 281:47-56.

Moyer, et al., "Botulinum Toxin Type B: Experimental and Clinical Experience," in Therapy with Botlinum Toxin, Jankovic, ed., 1994, pp. 71-84.

Gonelle-Gispert, "SNAP-25a and -25b isoforms are both expressed in insulin secreting cells and can function in insulin secretion," Biochem. J. (1999) 339:159-165.

International Conference on Botulinum Toxin: Basic Science and Clinical Therapeutics, Mov. Disord. (1995) 10:361-408.

Haberman, et al., "Tetanus toxin and botulinum A and C neurotoxins inhibit noradrenaline release from cultured mouse brain," J. Neurochem. (1988) 51:522-527.

Sanchez-Prieto, et al., "Botulinum toxin A blocks glutamate exocytosis from guinea pig cerebral cortical synaptosomes," Eur. J. Biochem. (1987) 165:675-681.

Pearce, "Pharmacologic characterization of botuinum toxin for basic science and medicine," Toxicon (date) 35:1373-1412.

Bigalke, et al., "Botulinum A neurotoxin inhibits non-cholinergic synaptic transmission in mouse spinal cord neurons in culture," Brain Res. (1985) 360:318-324.

Habermann, "Inhibition by tetanus and botulinum A toxin of the relaease of [3H] noradrenaline and [3H] GABA from rat brain homogenate," Experientia (1988) 44:224-226.

Bigalke, et al., "Tetanus toxin and botulinum A toxin inhibit release and uptake of various transmitters as studied with particulate preparations from rat brain and spinal cord," Naunyn-Schmiedelberg's Arch. Pharmacol. (1981) 316:244-251.

Jancovic, et al., eds., "Therapy with Botulinum Toxin," New York, Marcel Dekkar, 1994. p. 5.

Schantz, et al., "Properties and use of botulinum toxin and other microbial neurotoxins in medicine," Microbial Rev. (1992) 56:80-99.

Sloop, et al., "Reconstituted botulinum toxin type A does not lose potency in humans if it is refrozen or refrigerated for two weeks before use," Neurology (1997) 48:249-253.

(Continued)

*Primary Examiner*—Chih-Min Kam
(74) *Attorney, Agent, or Firm*—Dean G. Stathakis; Joel B. German; Martin A. Voet

(57) ABSTRACT

The present invention relates to rescue agents for use in the treatments of toxin intoxication—for example botulinum intoxication, which can result from food poisoning, an act of bioterrorism, or from accidental overdose in the course of treatment. In some embodiments, the rescue agents comprise at least one of an inactive *botulinum* toxin and a modified nontoxic nonhemagglutinin. The present invention also provides for glycosylated active and inactive toxins and methods of using same.

16 Claims, 13 Drawing Sheets

OTHER PUBLICATIONS

Galbiati, et al., "Identification, sequence and developmental expression of invertebrate flotillins from Drosophila melanogaster," Gene (1998) 210:229-237.

Li, et al., "Src tyrosine kinases, Galpha subunits, and H-ras share a common membrane-anchored scaffolding protein, caveolin," J. Biol. Chem. (1996) 271:29182-29190.

Ishizaka, et al., "Angiotensin II tyhpe receptor: Relationship with caveolae and caveolin after initial agonist simulation," Hypertension (1998) 32:459-466.

Ju, et al., "Inhibitory interactions of the bradykinin B2 receptor with endothelial nitric-acid synthase," J. Biol. Chem. (1998) 273:24025-24029.

Webb, et al., "SR-BII, and isoform of the scavenger receptor BI containing an alternate cytoplasmic tail, mediates lipid transfer between high density lipoprotein and cells," J. Biol. Chem. (1998) 273:15241-15248.

Drab, et al., "Loss of caveolae, vascular dysfunction, and prliminary defects in caveolin-1 gene-disrupted mice," Science (2001) 293:2449-2452.

Bouillot, et al., "Axonal amyloid precursor protein expressed by neurons in vitro is present in a membrane fraction with caveolae-like properties," J. Biol. Chem. (1996) 271:7640-7644.

Razani, et al., "Caveolae: From cell biology to animal physiology," Pharmacol. Rev. (2002) 54:431-467.

Li, et al., "Phosphorylation of caveolin by src tyrosine kinases," J. Biol. Chem. (1996) 271:3863-3868.

Razani and Lisanti, "Caveolin-deficient mice:insights into caveolar function and human disease," J. Clin. Investig. (2001) 108:1553-1561.

Garcia-Cardena, et al., "Dissecting the Interaction between nitric oxide synthase (NOS) and caveolin," J. Biol. Chem. (1997) 272:25437-25440.

Sotgia, et al., "Intracellular retention of glycophosphatidylinositol-linked proteins in caveolin-deficient cells," Mol. Cell. Biol. (2002) 22:3905-3926.

Frank, et al., "Influence of caveolin-1 on cellular cholesterol efflux mediated by high-density lipoproteins," Am. J. Physiol. Cell Physiol. (2001) 280:C1204-C1214.

Galbiati, et al., "Caveolin-1 expression negatively reguates cell cycle progression by inducing G0/G1 arrest via a p53/p21WAF1/Cip1-dependent mechanism," Mol. Biol. Cell. (2001) 12:2229-2244.

Frank, et al., "Adenovirus-mediated expression of cavolin-1 in mouse liver increases plasma high-density lipoprotein levels," Biochemistry (2001) 40:10892-10900.

Lee, et al., "Src-induced phosphorylation of caveolin-2 on tyrosine 19," J. Biol. Chem. (2002) 277:34556-34567.

Couet, et al., "Identification of peptide and protein ligands for the caveolin-scaffolding domain," J. Biol. Chem. (1997) 272:6525-6533.

Lee, et al., "Constitutive and growth factor-regulated phosphorylation of caveolin-1 ocurrs at the same site (Tyr-14) in vivo: identification of a c-src/cav-1/grb7 signalling cassette," Mol. Endocrinol. (2000) 14:1750-1775.

Sato, et al., "Reconstitution of src-dependent phospholipase Cgamma phosphorylation and transient calcium release by using membrane rafts and cell-free extracts from Xenopus eggs," J. Biol. Chem (2003) 278:38413-38420.

Gargalovic and Dory, "Cellular apoptosis is associated with increased caveolin-1 expression in macrophages," J. Lipid Res. (2003) 44:1622-1632.

Hamer, et al., "Rational design of drugs that induce human immunodeficiency virus replication," J. Virol. (2003) 77:10227-10236.

McIntosh, et al., "Targeting endothelium and its dynamic caveolae for tissue-specific transcytosis in vivo: a pathway to overcome cell barriers to drug and gene delivery," Proc. Natl. Acad. Sci. USA (2002) 99:1996-2001.

Li, et al., "Baculovirus-based expression of mammalian caveolin in Sf21 insect cells," J. Biol. Chem. (1996) 271:28647-28654.

Li, et al., "Expression and characterization of recombinant caveolin," J. Biol. Chem. (1996) 271:568-573.

Dobrosotskaya, et al., "Reconstitution of sterol-regulated endoplasmic reticulum-to-Golgi transport of SREBP-2 in insect cells by co-expression of mammalian SCAP and insigs," J. Biol. Chem. (2003) 278:35837-35843.

Schnitzer, et al., "Endothelial caveolae have the molecular transport machinary for vesicle budding, docking, and fusion including VAMP, NSF, SNAP, annexins and GTPases," J. Biol. Chem. (1995) 270:14399-14404.

Hayashi, et al., "Amyloid precursor protein in unique cholesterol-rich microdomains different from caveolae-like domains," Biochim. Biophys. Acta (2000) 1483:81-90.

Banwait, et al., "Role of nitric acid in beta(3)-adrenoreceptor activation on basal tone of internal anal sphincter," Am. J. Physiol.-Gastroint. Liver Physiol. (2003) 285:G547-G555.

McLoon and Christiansen, "Increasing extraocular muscle strength with insulin-like growth factor," Investig. Opthamol. Visual Sci. (2003) 44:3866-3872.

Carver and Schnitzer, "Caveolae: mining little caves for new cancer targets," Nature Reviews Cancer (2003) 3:571-581.

Schnitzer, "Caveolae: from basic trafficking mechanisms to targeting transcytosis for tissue-specific drug and gene delivery in vivo," Adv. Drug. Deliv. Rev. (2001) 28:265-280.

McIntosh and Schnitzer, "Caveolae require intact VAMP for targeted transport in vascular endothelium," Am. J. Physiol. (1999) 277:H2222-H2232.

Lee, et al., "Tumor cell growth inhibition by caveolin re-expression in human breast cancer cells," Oncogene (1998) 16:1391-1397.

Pajvani, et al., "Structure-function studies of the adipocyte-secreted hormone Acrp30/adiponectin. Implications for metabolic regulation and bioactivity," J. Biol. Chem. (2003) 278:9073-9085.

Mynarcik, et al., "Adiponectin and leptin levels in HIV-infected subjects with insulin resistance and body fat redistribution," J. Acquir. Immun. Defic. Syndr. (2002) 31:514-520.

Rajala, et al., "Adipose-derived resistin and gut-derived resistin-like molecule-beta selectively impair insulin action on glucose production," J. Clin. Invest. (2003) 11:225-230.

Menzaghi, et al., "A haplotype at the adiponectin locus is associated with obesity and other features of the insulin resistance syndrome," Diabetes (2002) 51:2306-2312.

Iyengar, et al., "Adipocyte-sereted factors synergistically promote mammary tumorigenesis through induction of anti-apoptotic transcriptional programs and proto-oncogene stabilization," Oncogene (2003) 22:6408-6423.

Cohen, et al., "Role of caveolin and caveolae in insulin signaling and diabetes," Am. J. Physiol. Endocrinol. Metab. (2003) 285:E1151-E1160.

Kratchmarova, et al., "A proteomic approach for identification of secreted proteins during the differentiation of 3T3-L1 preadipocytes to adipocytes," Mol. Cell. Proteomics (2002) 1:213-222.

Combs, et al., "Induction of adipocyte complement-related protein of 30 kilodaltons by PPARgamma agonists: a potential mechanism of insulin sensitization," Endocrinology (2002) 143:998-1007.

Berg, et al., "ACRP30/adiponectin: an adipokine regulating glucose and lipid metabolism," Trends Endocrinol. Metab. (2002) 13:84-89.

Combs, et al., "Endogenous glucose production is inhibited by the adipose-derived protein Acrp30," J. Clin. Invest. (2001) 108:1875-1881.

Razani, et al., "Caveolin-1-deficient mice are lean, resistant to diet-inuced obesity, and show hypertriglyceridemia with adipocyte abnormalities," J. Biol. Chem. (2002) 277:8635-8647.

Shin, et al., "Involvement of cellular caveolae in bacterial entry into mast cells," Science (2000) 289:785-788.

Burgueno, et al., "Metabotropic glutamate type 1aplha receptor localizes in low-density caveolin-rish plasma membrane fractions," J. Neurochem. (2003) 86:785-791.

Tang, et al., "Expression of metabotropic glutamate receptor 1alpha in the hippocampus of rat pilocarpine model of status epilepticus," Epilepsy Res. (2001) 46:179-189.

Ciruela, et al., "Metabotropic glutamate 1alpha and adenosine A1 receptors assemble into functionally interacting complexes," J. Biol. Chem. (2001) 276:18345-18351.

Zhang, et al., "Localization and regulation of the delta-opiod receptor in dorsal root ganglia and spinal cord of the rat and monkey: evidence for association with the membrane of large dense-core vesicles," Neuroscience (1998) 82:1225-1242.

Skoff, et al., "Nerve growth factor (NF) and glial cell line-derived neurotrophic factor (GDNF) regulate substance P release in adult spinal sensory neurons," Neurochem. Res. (2003) 28:847-854.

Schaible, et al., "Mechanisms of pain in arthritis," Ann. NY Acad. Sci. (2002) 966:343-354.

Xu et al., "On the role of galanin, substance P and other neuropeptides in primary sensory neurons of the rat: studies on spinal reflex excitability and peripheral axotomy," Eur. J. Neurosci. (1990) 2:733-743.

Trevisani, et al., "Ethanol elicits and potentiates nocicepter responses via the vanilloid receptor," Nat. Neurosci. (2002) 5:546-551.

Malcangio, et al., "A novel control mechanism based on GDNF modulation of somatostatin release from sensory neurones," FASEB J. (2002) 16:730-732.

Southall, et al., "Twenty-four hour exposure to prostaglandin down regulates prostanoid receptor binding but does not alter PGE(2)-mediated sensitization or rat sensory neurons," Pain (2002) 96:285-296.

Marvizon, et al., "Neurokinin 1 receptor internalization in spinal cord slices induce by dorsal root stimulation is mediated by NMDA receptors," J. Neurosci. (1997) 17:8129-8136.

Morioka, et al., "Interleukin-1beta-induced substance P release from rat cultured primary afferent neurons driven by two phospholipase A2 enzymes: secretory type IIA and cystolic type IV," J. Neurochem. (2002) 80:989-997.

Allen, et al., "Noxious cutaneous thermal stimuli induce a graded release of endogenous substance P in the spinal cord: imaging peptide action in vivo," J. Neurosci. (1997) 17:5921-5927.

Harris, et al., "Expression of caveolin by bovine lymphocytes and antigen-presenting cells," Immunology (2002) 105:190-195.

Shin and Abraham, "Glycosylphophatidylinositol-anchored receptor-mediated bacterial endocytosis," FEMS Microbiol. Lett. (2001) 197:131-138.

Field, et al., "Fc epsilon RI-mediated recruitment of p53/56lyn to detergent resistent membrane domains accompnies cellular signalling," Proc. Natl. Acad. Sci. USA (1995) 92:9201-9205.

Baig, et al., "Agonist activated adrenocorticotropin receptor internalizes via a clathrin-mediated G protein receptor kinase dependent mechanism," Endocrin. Res. (2002) 28:281-289.

Kohno, et al., "N-glycans of sphingosine 1-phosphate receptor Edg-1 regulate ligand-induced receptor internalization," FASEB J. (2002) 16:983-992.

Dale, et al., "Agonist-stimulated and tonic internalization of metabotropic glutamate receptor 1a in human embryonic kidney 293 cells: agonist-stimulated endocytosis is beta-arrestin 1 isoform-specific," Mol. Pharmacol. (2001) 60:1243-1253.

Ostrom, et al., "Receptor number and caveolar co-localization determine receptor coupling efficiency to adenylyl cyclase," J. Biol. Chem. (2001) 276:42063-42069.

Ostrom, et al., "Stoichiometry and compartmentation in G protein-coupled receptor signalling: implications for therapeutic interventions involving G(s)," J. Pharmacol. Exp. Ther. (2000) 294:407-412.

Riddell, et al., "Compartmentalization of beta-secretase (Asp20 into low-bouyant density, noncaveolar lipid rafts," Curr. Biol. (2001) 11:1288-1293.

Rouvinski, et al., "Both raft- and non-raft proteins associate with CHAPS-insoluble complexes: some APP in large complexes," Biochem. Biophys. Res. Comm. (2003) 308:750-758.

Ikezu, et al., "Caveolae, plasma membrane microdomains for alpha-secretase-mediated processing of the amyloid secretory protein," J. Biol. Chem. (1998) 273:10485-10495.

Figure 1. N-linked oligosaccharides for glycosylation

Peptide sequence (SEQ ID NO:5):
```
MPFVNKQFNY KDPVNGVDIA YIKIPNAGQM QPVKAFKIHN KIWVIPERDT FTNPEEGDLN
PPPEAKQVPV SYYDSTYLST DNEKDNYLKG VTKLFERIYS TDLGRMLLTS IVRGIPFWGG
STIDTELKVI DTNCINVIQP DGSYRSEELN LVIIGPSADI IQFECKSFGH EVLNLTRNGY
GSTQYIRFSP DFTFGFEESL EVDTNPLLGA GKFATDPAVT LAHELIHAGH RLYGIAINPN
RVFKVNTNAY YEMSGLEVSF EELRTFGGHD AKFIDSLQEN EFRLYYYNKF KDIASTLNKA
KSIVGTTASL QYMKNVFKEK YLLSEDTSGK FSVDKLKFDK LYKMLTEIYT EDNFVKFFKV
LNRKTYLNFD KAVFKINIVP KVNYTIYDGF NLRNTNLAAN FNGQNTEINN MNFTKLKNFT
GLFEFYKLLC VRGIITSKTK SLDKGYNKAL NDLCIKVNNW DLFFSPSEDN FTNDLNKGEE
ITSDTNIEAA EENISLDLIQ QYYLTFNFDN EPENISIENL SSDIIGQLEL MPNIERFPNG
KKYELDKYTM FHYLRAQEFE HGKSRIALTN SVNEALLNPS RVYTFFSSDY VKKVNKATEA
AMFLGWVEQL VYDFTDETSE VSTTDKIADI TIIIPYIGPA LNIGNMLYKD DFVGALIFSG
AVILLEFIPE IAIPVLGTFA LVSYIANKVL TVQTIDNALS KRNEKWDEVY KYIVTNWLAK
VNTQIDLIRK KMKEALENQA EATKAIINYQ YNQYTEEEKN NINFNIDDLS SKLNESINKA
MININKFLNQ CSVSYLMNSM IPYGVKRLED FDASLKDALL KYIYDNRGTL IGQVDRLKDK
VNNTLSTDIP FQLSKYVDNQ RLLSTFTEYI KNIINTSILN LRYESNHLID LSRYASKINI
GSKVNFDPID KNQIQLFNLE SSKIEVILKN AIVYNSMYEN FSTSFWIRIP KYFNSISLNN
EYTIINCMEN NSGWKVSLNY GEIIWTLQDT QEIKQRVVFK YSQMINISDY INRWIFVTIT
NNRLNNSKIY INGRLIDQKP ISNLGNIHAS NNIMFKLDGC RDTHRYIWIK YFNLFDKELN
EKEIKDLYDN QSNSGILKDF WGDYLQYDKP YYMLNLYDPN KYVDVNNVGI RGYMYLKGPR
GSVMTTNIYL NSSLYRGTKF IIKKYASGNK DNIVRNNDRV YINVVVKNKE YRLATNASQA
GVEKILSALE IPDVGNLSQV VVMKSKNDQG ITNKCKMNLQ DNNGNDIGFI GFHQFNNIAK
LVASNWYNRQ IERSSRTLGC SWEFIPVDDG WGERPL
```

Peptides containing the motif 'N-X-S/T/C (X not P)'(underlined):

| position | Peptide | SEQ ID NO: |
|---|---|---|
| 167-177 | SFGHEVLNLTR | 6 |
| 382-393 | VNYTIYDGFNLR | 7 |
| 394-415 | NTNLAANFNGQNTEINNMNFTK | 8 |
| 418-427 | NFTGLFEFYK | 9 |
| 457-477 | VNNWDLFFSPSEDNFTNDLNK | 10 |
| 478-536 | GEEITSDTNIEAAEENISLD LIQQYYLTFNFDNEPENISI ENLSSDIIGQLELMPNIER | 11 |
| 773-779 | LNESINK | 12 |
| 787-806 | FLNQCSVSYLMNSMIPYGVK | 13 |
| 841-855 | VNNTLSTDIPFQLSK | 14 |
| 872-882 | NIINTSILNLR | 15 |
| 930-948 | NAIVYNSMYENFSTSFWIR | 16 |
| 952-975 | YFNSISLNNEYTIINCMENNSGWK | 17 |
| 1001-1013 | YSQMINISDYINR | 18 |
| 1024-1028 | LNNSK | 19 |
| 1086-1098 | DLYDNQSNSGILK | 20 |
| 1141-1156 | GSVMTTNIYLNSSLYR | 21 |
| 1193-1204 | LATNASQAGVEK | 22 |
| 1205-1224 | ILSALEIPDVGNLSQVVVMK | 23 |

Figure 1 Continue.

Peptide sequence (SEQ ID NO:39):
```
KTKSLDKGYN KALNDLCIKV NNWDLFFSPS EDNFTNDLNK GEEITSDTNI EAAEENISLD
LIQQYYLTFN FDNEPENISI ENLSSDIIGQ LELMPNIERF PNGKKYELDK YTMFHYLRAQ
EFEHGKSRIA LTNSVNEALL NPSRVYTFFS SDYVKKVNKA TEAAMFLGWV EQLVYDFTDE
TSEVSTTDKI ADITIIIPYI GPALNIGNML YKDDFVGALI FSGAVILLEF IPEIAIPVLG
TFALVSYIAN KVLTVQTIDN ALSKRNEKWD EVYKYIVTNW LAKVNTQIDL IRKKMKEALE
NQAEATKAII NYQYNQYTEE EKNNINFNID DLSSKLNESI NKAMININKF LNQCSVSYLM
NSMIPYGVKR LEDFDASLKD ALLKYIYDNR GTLIGQVDRL KDKVNNTLST DIPFQLSKYV
DNQRLLSTFT EYIKNIINTS ILNLRYESNH LIDLSRYASK INIGSKVNFD PIDKNQIQLF
NLESSKIEVI LKNAIVYNSM YENFSTSFWI RIPKYFNSIS LNNEYTIINC MENNSGWKVS
LNYGEIIWTL QDTQEIKQRV VFKYSQMINI SDYINRWIFV TITNNRLNNS KIYINGRLID
QKPISNLGNI HASNNIMFKL DGCRDTHRYI WIKYFNLFDK ELNEKEIKDL YDNQSNSGIL
KDFWGDYLQY DKPYYMLNLY DPNKYVDVNN VGIRGYMYLK GPRGSVMTTN IYLNSSLYRG
TKFIIKKYAS GNKDNIVRNN DRVYINVVVK NKEYRLATNA SQAGVEKILS ALEIPDVGNL
SQVVVMKSKN DQGITNKCKM NLQDNNGNDI GFIGFHQFNN IAKLVASNWY NRQIERSSRT
LGCSWEFIPV DDGWGERPL
```

Peptides containing the motif 'N-X-S/T/C (X not P)':

| position | peptide | SEQ ID NO: |
|---|---|---|
| 20-40 | VNNWDLFFSPSEDNFTNDLN K | 25 |
| 41-99 | GEEITSDTNIEAAEENISLD LIQQYYLTFNFDNEPENISI ENLSSDIIGQLELMPNIER | 26 |
| 336-342 | LNESINK | 27 |
| 350-369 | FLNQCSVSYLMNSMIPYGVK | 28 |
| 404-418 | VNNTLSTDIPFQLSK | 29 |
| 435-445 | NIINTSILNLR | 30 |
| 493-511 | NAIVYNSMYENFSTSFWIR | 31 |
| 515-538 | YFNSISLNNEYTIINCMENN SGWK | 32 |
| 564-576 | YSQMINISDYINR | 33 |
| 587-591 | LNNSK | 34 |
| 649-661 | DLYDNQSNSGILK | 35 |
| 704-719 | GSVMTTNIYLNSSLYR | 36 |
| 756-767 | LATNASQAGVEK | 37 |
| 768-787 | ILSALEIPDVGNLSQVVVMK | 38 |

Figure 2.
Peptide sequence (SEQ ID NO: 5):

```
MPFVNKQFNY KDPVNGVDIA YIKIPNAGQM QPVKAFKIHN KIWVIPERDT FTNPEEGDLN
PPPEAKQVPV SYYDSTYLST DNEKDNYLKG VTKLFERIYS TDLGRMLLTS IVRGIPFWGG
STIDTELKVI DTNCINVIQP DGSYRSEELN LVIIGPSADI IQFECKSFGH EVLNLTRNGY
GSTQYIRFSP DFTFGFEESL EVDTNPLLGA GKFATDPAVT LAHELIHAGH RLYGIAINPN
RVFKVNTNAY YEMSGLEVSF EELRTFGGHD AKFIDSLQEN EFRLYYYNKF KDIASTLNKA
KSIVGTTASL QYMKNVFKEK YLLSEDTSGK FSVDKLKFDK LYKMLTEIYT EDNFVKFFKV
LNRKTYLNFD KAVFKINIVP KVNYTIYDGF NLRNTNLAAN FNGQNTEINN MNFTKLKNFT
GLFEFYKLLC VRGIITSKTK SLDKGYNKAL NDLCIKVNNW DLFFSPSEDN FTNDLNKGEE
ITSDTNIEAA EENISLDLIQ QYYLTFNFDN EPENISIENL SSDIIGQLEL MPNIERFPNG
KKYELDKYTM FHYLRAQEFE HGKSRIALTN SVNEALLNPS RVYTFFSSDY VKKVNKATEA
AMFLGWVEQL VYDFTDETSE VSTTDKIADI TIIIPYIGPA LNIGNMLYKD DFVGALIFSG
AVILLEFIPE IAIPVLGTFA LVSYIANKVL TVQTIDNALS KRNEKWDEVY KYIVTNWLAK
VNTQIDLIRK KMKEALENQA EATKAIINYQ YNQYTEEEKN NINFNIDDLS SKLNESINKA
MININKFLNQ CSVSYLMNSM IPYGVKRLED FDASLKDALL KYIYDNRGTL IGQVDRLKDK
VNNTLSTDIP FQLSKYVDNQ RLLSTFTEYI KNIINTSILN LRYESNHLID LSRYASKINI
GSKVNFDPID KNQIQLFNLE SSKIEVILKN AIVYNSMYEN FSTSFWIRIP KYFNSISLNN
EYTIINCMEN NSGWKVSLNY GEIIWTLQDT QEIKQRVVFK YSQMINISDY INRWIFVTIT
NNRLNNSKIY INGRLIDQKP ISNLGNIHAS NNIMFKLDGC RDTHRYIWIK YFNLFDKELN
EKEIKDLYDN QSNSGILKDF WGDYLQYDKP YYMLNLYDPN KYVDVNNVGI RGYMYLKGPR
GSVMTTNIYL NSSLYRGTKF IIKKYASGNK DNIVRNNDRV YINVVVKNKE YRLATNASQA
GVEKILSALE IPDVGNLSQV VVMKSKNDQG ITNKCKMNLQ DNNGNDIGFI GFHQFNNIAK
LVASNWYNRQ IERSSRTLGC SWEFIPVDDG WGERPL
```

Peptides containing S or T (underlined):

| position | peptide | SEQ ID NO: |
|---|---|---|
| 49-66 | DTFTNPEEGDLNPPPEAK | 40 |
| 67-84 | QVPVSYYDSTYLSTDNEK | 41 |
| 90-93 | GVTK | 42 |
| 98-105 | IYSTDLGR | 43 |
| 106-113 | MLLTSIVR | 44 |
| 114-128 | GIPFWGGSTIDTELK | 45 |
| 129-145 | VIDTNCINVIQPDGSYR | 46 |
| 146-166 | SEELNLVIIGPSADIIQFEC K | 47 |
| 167-177 | SFGHEVLNLTR | 48 |
| 178-187 | NGYGSTQYIR | 49 |
| 188-212 | FSPDFTFGFEESLEVDTNPL LGAGK | 50 |
| 213-231 | FATDPAVTLAHELIHAGHR | 51 |
| 245-264 | VNTNAYYEMSGLEVSFEELR | 52 |
| 265-272 | TFGGHDAK | 53 |
| 273-283 | FIDSLQENEFR | 54 |
| 292-299 | DIASTLNK | 55 |
| 302-314 | SIVGTTASLQYMK | 56 |
| 321-330 | YLLSEDTSGK | 57 |
| 331-335 | FSVDK | 58 |
| 344-356 | MLTEIYTEDNFVK | 59 |
| 365-371 | TYLNFDK | 70 |
| 382-393 | VNYTIYDGFNLR | 71 |
| 394-415 | NTNLAANFNGQNTEINNMNF TK | 72 |
| 418-427 | NFTGLFEFYK | 73 |
| 433-438 | GIITSK | 74 |
| 439-440 | TK | 75 |
| 441-444 | SLDK | 76 |

Figure 2
Continue

| Range | Sequence | # |
|---|---|---|
| 457-477 | VNNWDLFFSPSEDNFTNDLN K | 77 |
| 478-536 | GEEITSDTNIEAAEENISLD LIQQYYLTFNFDNEPENISI ENLSSDIIGQLELMPNIER | 78 |
| 548-555 | YTMFHYLR | 79 |
| 564-565 | SR | 80 |
| 566-581 | IALTNSVNEALLNPSR | 81 |
| 582-592 | VYTFFSSDYVK | 82 |
| 597-626 | ATEAAMFLGWVEQLVYDFTD ETSEVSTTDK | 83 |
| 627-649 | IADITIIPYIGPALNIGNM LYK | 84 |
| 650-688 | DDFVGALIFSGAVILLEFIP EIAIPVLGTFALVSYIANK | 85 |
| 689-701 | VLTVQTIDNALSK | 86 |
| 712-720 | YIVTNWLAK | 87 |
| 721-729 | VNTQIDLIR | 88 |
| 734-744 | EALENQAEATK | 89 |
| 745-759 | AIINYQYNQYTEEEK | 90 |
| 760-772 | NNINFNIDDLSSK | 91 |
| 773-779 | LNESINK | 92 |
| 787-806 | FLNQCSVSYLMNSMIPYGVK | 93 |
| 808-816 | LEDFDASLK | 94 |
| 828-836 | GTLIGQVDR | 95 |
| 841-855 | VNNTLSTDIPFQLSK | 96 |
| 862-871 | LLSTFTEYIK | 97 |
| 872-882 | NIINTSILNLR | 98 |
| 883-893 | YESNHLIDLSR | 99 |
| 894-897 | YASK | 100 |
| 898-903 | INIGSK | 101 |
| 912-923 | NQIQLFNLESSK | 102 |
| 930-948 | NAIVYNSMYENFSTSFWIR | 103 |
| 952-975 | YFNSISLNNEYTIINCMENN SGWK | 104 |
| 976-994 | VSLNYGEIIWTLQDTQEIK | 105 |
| 1001-1013 | YSQMINISDYINR | 106 |
| 1014-1023 | WIFVTITNNR | 107 |
| 1024-1028 | LNNSK | 108 |
| 1035-1056 | LIDQKPISNLGNIHASNNIM FK | 109 |
| 1062-1065 | DTHR | 110 |
| 1086-1098 | DLYDNQSNSGILK | 111 |
| 1141-1156 | GSVMTTNIYLNSSLYR | 112 |
| 1157-1159 | GTK | 113 |
| 1165-1170 | YASGNK | 114 |
| 1193-1204 | LATNASQAGVEK | 115 |
| 1205-1224 | ILSALEIPDVGNLSQVVVMK | 116 |
| 1225-1226 | SK | 117 |
| 1227-1234 | NDQGITNK | 118 |
| 1261-1269 | LVASNWYNR | 119 |
| 1274-1276 | SSR | 120 |
| 1277-1296 | TLGCSWEFIPVDDGWGERPL | 121 |

M. See Blue Plus2 marker
1. pBAC-1/LCA, H227Y
2. pBAC-1/LCA
3. pBACgus-1/LCA, H227Y
4. pBACgus-1/LCA
5. AcNPV, negative control
6. Sf9 insect cells only
7. E.coli expressed LCA

Figure 4

BoNT/LC —

WB: Anti-His mAb

LC/A —

WB: Anti-LCA pAb 1. pBAC-1/LCA, H227Y
2. pBAC-1/LCA
3. pBACgus-1/LCA, H227Y
4. pBACgus-1/LCA
5. AcNPV, negative control
6. Sf9 insect cells only
7, 8, E.coli expressed LCA
$M_1$, SeeBlue Plus2

1. pBAC-1/LCA, inactive (H227Y)
2. pBAC-1/LCA, active
3. pBACgus-1/LCA, inactive (H227Y)
4. pBACgus-1/LCA
5. AcNPV, negative control
6. Sf9 insect cell lysate only
7. rLCA, positive control
8. Substrate only

Figure 6

| | | | | | | | | | | | |
|---|---|---|---|---|---|---|---|---|---|---|---|
| M | 5 | 4 | 3 | 2 | 1 | 6 | 5 | 4 | 3 | 2 | 1 | iBoNT/A →

120 kDa →

100 kDa →

WB: anti-LCA
(1:30,000)

WB: anti-Toxin A
(1:5,000)

1. pBAC-1/iBoNT/A, 0.5 µg
2. pBACgus-1/iBoNT/A, 0.5 µg
3. AcNPV only
4. pBAC-1/iBoNT/A, 1 µg
5. pBACgus-1/iBoNT/A, 1 µg
6. Uninfected Sf21 cells
M1. MagicMark
M2. Prestained SeeBlue Plus2 marker

Figure 7.

IB: BoNT/A pAb

Lane 1: vector alone
Lane 2: BoNT/A-HC

IB: His Tag mAb

Lane 1: vector alone
Lane 2: BoNT/A-HC

Figure 8.

A) pAb: anti-LCA

B) pAb: anti-Toxin A

A) Samples

M1 Magic Marker
1. LCA-mutant in pBAC-1, 25 µg
2. LCA-wt in pBAC-1, 25 µg
3. LCA-mutant in pBACgus-1, 25µg
4. LCA-wt in pBACgus-1, 25 µg
5. AcNPV only, 25 µg
6. uninfected Sf21, 25 µg
M2 SeebluePlus marker B) Samples M1 Magic Marker
1. iBoNT/A in pBAC-1, 50 µg
2. iBoNT/A in pBACgus-1, 50 µg
3. iBoNT/A in pBAC-1, 50 µg
4. iBoNT/A in pBACgus-1, 50 µg
5. AcNPV only, 50 µg
6. uninfected Sf21, 50 µg
7. iBoNT/A in pBAC-1, 100 µg
8. iBoNT/A in pBACgus-1, 100 µg

Figure 9.

1. LCA in pBAC-1, 11/02
2. LCA-mutant in pBAC-1
3. LCA-wt in pBAC-1
4. LCA-mutant in pBACgus-1
5. LCA-wt in pBACgus-1
6. iBoNT/A in pBAC-1, 0.5 μg
7. iBoNT/A in pBACgus-1, 0.5 μg
8. iBoNT/A in pBAC-1, 1 μg
9. iBoNT/A in pBACgus-1, 1 μg
10. AcNPV only, negative control
11. Uninfected Sf21
12. E.Coli expressed rLCA
13. Substrate

Figure 10

```
   1    MPFVNKQFNY  KDPVNGVDIA  YIKIPNAGQM  QPVKAFKIHN  KIWVIPERDT
  51    FTNPEEGDLN  PPPEAKQVPV  SYYDSTYLST  DNEKDNYLKG  VTKLFERIYS
 101    TDLGRMLLTS  IVRGIPFWGG  STIDTELKVI  DTNCINVIQP  DGSYRSEELN
 151    LVIIGPSADI  IQFECKSFGH  EVLNLTRNGY  GSTQYIRFSP  DFTFGFEESL
 201    EVDTNPLLGA  GKFATDPAVT  LAHELIYAGH  RLYGIAINPN  RVFKVNTNAY
 251    YEMSGLEVSF  EELRTFGGHD  AKFIDSLQEN  EFRLYYYNKF  KDIASTLNKA
 301    KSIVGTTASL  QYMKNVFKEK  YLLSEDTSGK  FSVDKLKFDK  LYKMLTEIYT
 351    EDNFVKFFKV  LNRKTYLNFD  KAVFKINIVP  KVNYTIYDGF  NLRNTNLAAN
 401    FNGQNTEINN  MNFTKLKNFT  GLFEFYKLLC  VRGIITSKTK  SLDKGYNKAL
 451    NDLCIKVNNW  DLFFSPSEDN  FTNDLNKGEE  ITSDTNIEAA  EENISLDLIQ
 501    QYYLTFNFDN  EPENISIENL  SSDIIGQLEL  MPNIERFPNG  KKYELDKYTM
 551    FHYLRAQEFE  HGKSRIALTN  SVNEALLNPS  RVYTFFSSDY  VKKVNKATEA
 601    AMFLGWVEQL  VYDFTDETSE  VSTTDKIADI  TIIIPYIGPA  LNIGNMLYKD
 651    DFVGALIFSG  AVILLEFIPE  IAIPVLGTFA  LVSYIANKVL  TVQTIDNALS
 701    KRNEKWDEVY  KYIVTNWLAK  VNTQIDLIRK  KMKEALENQA  EATKAIINYQ
 751    YNQYTEEEKN  NINFNIDDLS  SKLNESINKA  MININKFLNQ  CSVSYLMNSM
 801    IPYGVKRLED  FDASLKDALL  KYIYDNRGTL  IGQVDRLKDK  VNNTLSTDIP
 851    FQLSKYVDNQ  RLLSTFTEYI  KNIINTSILN  LRYESNHLID  LSRYASKINI
 901    GSKVNFDPID  KNQIQLFNLE  SSKIEVILKN  AIVYNSMYEN  FSTSFWIRIP
 951    KYFNSISLNN  EYTIINCMEN  NSGWKVSLNY  GEIIWTLQDT  QEIKQRVVFK
1001    YSQMINISDY  INRWIFVTIT  NNRLNNSKIY  INGRLIDQKP  ISNLGNIHAS
1051    NNIMFKLDGC  RDTHRYIWIK  YFNLFDKELN  EKEIKDLYDN  QSNSGILKDF
1101    WGDYLQYDKP  YYMLNLYDPN  KYVDVNNVGI  RGYMYLKGPR  GSVMTTNIYL
1151    NSSLYRGTKF  IIKKYASGNK  DNIVRNNDRV  YINVVVKNKE  YRLATNASQA
1201    GVEKILSALE  IPDVGNLSQV  VVMKSKNDQG  ITNKCKMNLQ  DNNGNDIGFI
1251    GFHQFNNIAK  LVASNWYNRQ  IERSSRTLGC  SWEFIPVDDG  WGERPLHHHH
1301    HH
```

Figure 11.

M, MagicMark
1, AcNPV, negative control
2, pBAC-1/iBoNT/A (H227Y)-His6
3, pBACgus-1/iBoNT/A (H227Y)-His6
4, uninfected Sf21 cells
5, Native BoNT/A, Pure A, 10 ng
6, Native BoNT/A, Pure A, 20 ng
7, Native BoNT/A, Pure A, 50 ng

RESCUE AGENTS FOR TREATING BOTULINUM TOXIN INTOXICATIONS

FIELD OF THE INVENTION

The present invention is directed to methods of treating *botulinum* toxin intoxication in a mammal with rescue agents. Rescue agents include inactive *botulinum* toxin and/or nontoxic nonhemagglutinin. The present invention is also directed to the method of making and using glycosylated *botulinum* toxins. Additionally, the present invention is also directed to methods of making di-chain *botulinum* toxins.

BACKGROUND OF THE INVENTION

*Botulinum* toxins have been used in clinical settings for the treatment of neuromuscular disorders characterized by hyperactive skeletal muscles. In 1989 a *botulinum* toxin type A complex has been approved by the U.S. Food and Drug Administration for the treatment of blepharospasm, strabismus and hemifacial spasm. Subsequently, a *botulinum* toxin type A was also approved by the FDA for the treatment of cervical dystonia and for the treatment of glabellar lines, and a *botulinum* toxin type B was approved for the treatment of cervical dystonia. Non-type A *botulinum* toxin serotypes apparently have a lower potency and/or a shorter duration of activity as compared to *botulinum* toxin type A. Clinical effects of peripheral intramuscular *botulinum* toxin type A are usually seen within one week of injection. The typical duration of symptomatic relief from a single intramuscular injection of *botulinum* toxin type A averages about three months, although significantly longer periods of therapeutic activity have been reported.

It has been reported that *botulinum* toxin type A has been used in clinical settings as follows:

(1) about 75–125 units of BOTOX® per intramuscular injection (multiple muscles) to treat cervical dystonia;

(2) 5–10 units of BOTOX® per intramuscular injection to treat glabellar lines (brow furrows) (5 units injected intramuscularly into the procerus muscle and 10 units injected intramuscularly into each corrugator supercilii muscle);

(3) about 30–80 units of BOTOX® to treat constipation by intrasphincter injection of the puborectalis muscle;

(4) about 1–5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.

(5) to treat strabismus, extraocular muscles have been injected intramuscularly with between about 1–5 units of BOTOX®, the amount injected varying based upon both the size of the muscle to be injected and the extent of muscle paralysis desired (i.e. amount of diopter correction desired).

(6) to treat upper limb spasticity following stroke by intramuscular injections of BOTOX® into five different upper limb flexor muscles, as follows:

(a) flexor digitorum profundus: 7.5 U to 30 U
 (b) flexor digitorum sublimus: 7.5 U to 30 U
 (c) flexor carpi ulnaris: 10 U to 40 U
 (d) flexor carpi radialis: 15 U to 60 U
 (e) biceps brachii: 50 U to 200 U.

Each of the five indicated muscles has been injected at the same treatment session, so that the patient receives from 90 U to 360 U of upper limb flexor muscle BOTOX® by intramuscular injection at each treatment session.

(7) to treat migraine, pericranial injected (injected symmetrically into glabellar, frontalis and temporalis muscles) injection of 25 U of BOTOX® has showed significant benefit as a prophylactic treatment of migraine compared to vehicle as measured by decreased measures of migraine frequency, maximal severity, associated vomiting and acute medication use over the three month period following the 25 U injection.

Additionally, intramuscular *botulinum* toxin has been used in the treatment of tremor in patient's with Parkinson's disease, although it has been reported that results have not been impressive. Marjama-Jyons, J., et al., *Tremor-Predominant Parkinson's Disease*, Drugs & Aging 16(4);273–278: 2000.

It is known that *botulinum* toxin type A can have an efficacy for up to 12 months (*European J. Neurology* 6 (Supp 4): S111-S1150:1999), and in some circumstances for as long as 27 months. *The Laryngoscope* 109:1344–1346:1999. However, the usual duration of an intramuscular injection of Botox® is typically about 3 to 4 months.

The success of *botulinum* toxin type A to treat a variety of clinical conditions has led to interest in other *botulinum* toxin serotypes. Two commercially available botulinum type A preparations for use in humans are BOTOX® available from Allergan, Inc., of Irvine, Calif., and Dysport® available from Beaufour Ipsen, Porton Down, England. A Botulinum toxin type B preparation (MyoBloc®) is available from Elan Pharmaceuticals of San Francisco, Calif.

In addition to having pharmacologic actions at the peripheral location, *botulinum* toxins may also have inhibitory effects in the central nervous system. Work by Weigand et al, *Nauny-Schmiedeberg's Arch. Pharmacol.* 1976; 292, 161–165, and Habermann, *Nauny-Schmiedeberg's Arch. Pharmacol.* 1974; 281, 47–56 showed that *botulinum* toxin is able to ascend to the spinal area by retrograde transport. As such, a *botulinum* toxin injected at a peripheral location, for example intramuscularly, may be retrograde transported to the spinal cord.

A *botulinum* toxin has also been proposed for the treatment of rhinorrhea, hyperhydrosis and other disorders mediated by the autonomic nervous system (U.S. Pat. No. 5,766, 605), tension headache, (U.S. Pat. No. 6,458,365), migraine headache (U.S. Pat. No. 5,714,468), post-operative pain and visceral pain (U.S. Pat. No. 6,464,986), pain treatment by intraspinal toxin administration (U.S. Pat. No. 6,113,915), Parkinson's disease and other diseases with a motor disorder component, by intracranial toxin administration (U.S. Pat. No. 6,306,403), hair growth and hair retention (U.S. Pat. No. 6,299,893), psoriasis and dermatitis (U.S. Pat. No. 5,670, 484), injured muscles (U.S. Pat. No. 6,423,319, various cancers (U.S. Pat. No. 6,139,845), pancreatic disorders (U.S. Pat. No. 6,143,306), smooth muscle disorders (U.S. Pat. No. 5,437,291, including injection of a *botulinum* toxin into the upper and lower esophageal, pyloric and anal sphincters)), prostate disorders (U.S. Pat. No. 6,365,164), inflammation, arthritis and gout (U.S. Pat. No. 6,063,768), juvenile cerebral palsy (U.S. Pat. No. 6,395,277), inner ear disorders (U.S. Pat. No. 6,265,379), thyroid disorders (U.S. Pat. No. 6,358,513), parathyroid disorders (U.S. Pat. No. 6,328,977). Additionally, controlled release toxin implants are known (see e.g. U.S. Pat. Nos. 6,306,423 and 6,312,708).

Seven generally immunologically distinct *botulinum* neurotoxins have been characterized: *botulinum* neurotoxin serotypes A, B, $C_1$, D, E, F and G. These serotypes are distinguished by neutralization with type-specific antibodies. The different serotypes of *botulinum* toxin vary in the animal species that they affect and in the severity and duration of the paralysis they evoke. For example, it has been determined that *botulinum* toxin type A is 500 times more potent, as measured by the rate of paralysis produced in the rat, than is botulinum toxin type B. Additionally, *botulinum* toxin type B has been determined to be non-toxic in primates at a dose of 480 U/kg which is about 12 times the primate $LD_{50}$ for *botulinum* toxin type A. Moyer E et al., *Botulinum Toxin Type B: Experimental and Clinical Experience*, being chapter 6, pages 71–85 of "Therapy With Botulinum Toxin", edited by Jankovic, J. et al. (1994), Marcel Dekker, Inc. *Botulinum* toxin apparently binds with high affinity to cholinergic motor neurons, is translocated into the neuron and blocks the release of acetylcholine.

Regardless of serotype, the molecular mechanism of toxin intoxication appears to be similar and to involve at least three steps or stages. In the first step of the process, the toxin binds to the presynaptic membrane of the target neuron through a specific interaction between the heavy chain, H chain, and a cell surface receptor; the receptor is thought to be different for each type of *botulinum* toxin and for tetanus toxin. The carboxyl end segment of the H chain, $H_C$, appears to be important for targeting of the toxin to the cell surface.

In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This step is thought to be mediated by the amino end segment of the H chain, $H_N$, which triggers a conformational change of the toxin in response to a pH of about 5.5 or lower. Endosomes are known to possess a proton pump which decreases intra-endosomal pH. The conformational shift exposes hydrophobic residues in the toxin, which permits the toxin to embed itself in the endosomal membrane. The toxin (or at a minimum the light chain) then translocates through the endosomal membrane into the cytoplasm.

The last step of the mechanism of *botulinum* toxin activity appears to involve reduction of the disulfide bond joining the heavy chain, H chain, and the light chain, L chain. The entire toxic activity of *botulinum* and tetanus toxins is contained in the L chain of the holotoxin; the L chain is a zinc (Zn++) endopeptidase which selectively cleaves proteins essential for recognition and docking of neurotransmitter-containing vesicles with the cytoplasmic surface of the plasma membrane, and fusion of the vesicles with the plasma membrane. Tetanus neurotoxin, *botulinum* toxin types B, D, F, and G cause degradation of synaptobrevin (also called vesicle-associated membrane protein (VAMP)), a synaptosomal membrane protein. Most of the VAMP present at the cytoplasmic surface of the synaptic vesicle is removed as a result of any one of these cleavage events. *Botulinum* toxin serotype A and E cleave SNAP-25. *Botulinum* toxin serotype $C_1$ was originally thought to cleave syntaxin, but was found to cleave syntaxin and SNAP-25. Each of the *botulinum* toxins specifically cleaves a different bond, except *botulinum* toxin type B (and tetanus toxin) which cleave the same bond.

Although all the *botulinum* toxins serotypes apparently inhibit release of the neurotransmitter acetylcholine at the neuromuscular junction, they do so by affecting different neurosecretory proteins and/or cleaving these proteins at different sites. For example, *botulinum* types A and E both cleave the 25 kiloDalton (kD) synaptosomal associated protein (SNAP-25), but they target different amino acid sequences within this protein. *Botulinum* toxin types B, D, F and G act on vesicle-associated protein (VAMP, also called synaptobrevin), with each serotype cleaving the protein at a different site. Finally, botulinum toxin type $C_1$ has been shown to cleave both syntaxin and SNAP-25. These differences in mechanism of action may affect the relative potency and/or duration of action of the various *botulinum* toxin serotypes. Apparently, a substrate for a *botulinum* toxin can be found in a variety of different cell types. See e.g. *Biochem, J* 1;339 (pt 1):159–65:1999, and *Mov Disord*, 10(3):376:1995 (pancreatic islet B cells contains at least SNAP-25 and synaptobrevin).

The molecular weight of the *botulinum* toxin protein molecule, for all seven of the known *botulinum* toxin serotypes, is about 150 kD. Interestingly, the *botulinum* toxins are released by Clostridial bacterium as complexes comprising the 150 kD *botulinum* toxin protein molecule along with associated non-toxin proteins. Thus, the *botulinum* toxin type A complex can be produced by Clostridial bacterium as 900 kD, 500 kD and 300 kD forms. Botulinum toxin types B and $C_1$ is apparently produced as only a 700 kD or 500 kD complex. Botulinum toxin type D is produced as both 300 kD and 500 kD complexes. Finally, botulinum toxin types E and F are produced as only approximately 300 kD complexes. The complexes (i.e. molecular weight greater than about 150 kD) are believed to contain a non-toxin hemagglutinin protein and a non-toxin and non-toxic non-hemagglutinin protein. These two non-toxin proteins (which along with the *botulinum* toxin molecule comprise the relevant neurotoxin complex) may act to provide stability against denaturation to the *botulinum* toxin molecule and protection against digestive acids when toxin is ingested. Additionally, it is possible that the larger (greater than about 150 kD molecular weight) *botulinum* toxin complexes may result in a slower rate of diffusion of the *botulinum* toxin away from a site of intramuscular injection of a *botulinum* toxin complex.

In vitro studies have indicated that *botulinum* toxin inhibits potassium cation induced release of both acetylcholine and norepinephrine from primary cell cultures of brainstem tissue. Additionally, it has been reported that *botulinum* toxin inhibits the evoked release of both glycine and glutamate in primary cultures of spinal cord neurons and that in brain synaptosome preparations *botulinum* toxin inhibits the release of each of the neurotransmitters acetylcholine, dopamine, norepinephrine (Habermann E., et al., *Tetanus Toxin and Botulinum A and C Neurotoxins Inhibit Noradrenaline Release From Cultured Mouse Brain*, J Neurochem 51(2);522–527:1988) CGRP, substance P and glutamate (Sanchez-Prieto, J., et al., *Botulinum Toxin A Blocks Glutamate Exocytosis From Guinea Pig Cerebral Cortical Synaptosomes*, Eur J. Biochem 165;675–681:1897. Thus, when adequate concentrations are used, stimulus-evoked release of most neurotransmitters is blocked by botulinum toxin. See e.g. Pearce, L. B., *Pharmacologic Characterization of Botulinum Toxin For Basic Science and Medicine*, Toxicon 35(9);1373–1412 at 1393; Bigalke H., et al., *Botulinum A Neurotoxin Inhibits Non-Cholinergic Synaptic Transmission in Mouse Spinal Cord Neurons in Culture*, Brain Research 360;318–324:1985; Habermann E., *Inhibition by Tetanus and Botulinum A Toxin of the release of [$^3H$]Noradrenaline and [$^3H$]GABA From Rat Brain Homogenate*, Experientia 44;224–226:1988, Bigalke H., et al., *Tetanus Toxin and Botulinum A Toxin Inhibit Release and Uptake of Various Transmitters, as Studied with Particulate Preparations From Rat Brain and Spinal Cord*, Naunyn-Schmiedeberg's Arch Pharmacol 316;244–251:1981, and; Jankovic J. et al., *Therapy With Botulinum Toxin*, Marcel Dekker, Inc., (1994), page 5.

*Botulinum* toxin type A can be obtained by establishing and growing cultures of *Clostridium botulinum* in a fermenter and then harvesting and purifying the fermented mixture in accordance with known procedures. All the *botulinum* toxin serotypes are initially synthesized as inactive single chain proteins which must be cleaved or nicked by proteases to become neuroactive. The bacterial strains that make *botulinum* toxin serotypes A and G possess endogenous proteases and serotypes A and G can therefore be recovered from bacterial cultures in predominantly their active form. In contrast, *botulinum* toxin serotypes $C_1$, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the *botulinum* toxin type B serotype only cleave a portion of the toxin produced. The exact proportion of nicked to unnicked molecules depends on the length of incubation and the temperature of the culture. Therefore, a certain percentage of any preparation of, for example, the *botulinum* toxin type B toxin is likely to be inactive, possibly accounting for the known significantly lower potency of *botulinum* toxin type B as compared to *botulinum* toxin type A. The presence of inactive *botulinum* toxin molecules in a clinical preparation will contribute to the overall protein load of the preparation, which has been linked to increased antigenicity, without contributing to its clinical efficacy. Additionally, it is known that *botulinum* toxin type B has, upon intramuscular injection, a shorter duration of activity and is also less potent than botulinum toxin type A at the same dose level.

High quality crystalline *botulinum* toxin type A can be produced from the Hall A strain of *Clostridium botulinum* with characteristics of $\geq 3 \times 10^7$ U/mg, an $A_{260}/A_{278}$ of less than 0.60 and a distinct pattern of banding on gel electrophoresis. The known Shantz process can be used to obtain crystalline *botulinum* toxin type A, as set forth in Shantz, E. J., et al, *Properties and use of Botulinum toxin and Other Microbial Neurotoxins in Medicine*, Microbiol Rev. 56;80–99:1992. Generally, the *botulinum* toxin type A complex can be isolated and purified from an anaerobic fermentation by cultivating *Clostridium botulinum* type A in a suitable medium. The known process can also be used, upon separation out of the non-toxin proteins, to obtain pure *botulinum* toxins, such as for example: purified botulinum toxin type A with an approximately 150 kD molecular weight with a specific potency of $1-2 \times 10^8$ $LD_{50}$ U/mg or greater; purified *botulinum* toxin type B with an approximately 156 kD molecular weight with a specific potency of $1-2 \times 10^8$ $LD_{50}$ U/mg or greater, and; purified botulinum toxin type F with an approximately 155 kD molecular weight with a specific potency of $1-2 \times 10^7$ $LD_{50}$ U/mg or greater.

*Botulinum* toxins and/or *botulinum* toxin complexes can be obtained from List Biological Laboratories, Inc., Campbell, California; the Centre for Applied Microbiology and Research, Porton Down, U.K.; Wako (Osaka, Japan), Metabiologics (Madison, Wis.) as well as from Sigma Chemicals of St Louis, Mo. Pure *botulinum* toxin can also be used to prepare a pharmaceutical composition.

As with enzymes generally, the biological activities of the *botulinum* toxins (which are intracellular peptidases) is dependant, at least in part, upon their three dimensional conformation. Thus, *botulinum* toxin type A is detoxified by heat, various chemicals surface stretching and surface drying. Additionally, it is known that dilution of the toxin complex obtained by the known culturing, fermentation and purification to the much, much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the toxin may be used months or years after the toxin containing pharmaceutical composition is formulated, the toxin can stabilized with a stabilizing agent such as albumin and gelatin.

A commercially available *botulinum* toxin containing pharmaceutical composition is sold under the trademark BOTOX® (available from Allergan, Inc., of Irvine, Calif.). BOTOX® consists of a purified *botulinum* toxin type A complex, albumin and sodium chloride packaged in sterile, vacuum-dried form. The *botulinum* toxin type A is made from a culture of the Hall strain of *Clostridium botulinum* grown in a medium containing N-Z amine and yeast extract. The *botulinum* toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. The vacuum-dried product is stored in a freezer at or below −5° C. BOTOX® can be reconstituted with sterile, non-preserved saline prior to intramuscular injection. Each vial of BOTOX® contains about 100 units (U) of *Clostridium botulinum* toxin type A purified neurotoxin complex, 0.5 milligrams of human serum albumin and 0.9 milligrams of sodium chloride in a sterile, vacuum-dried form without a preservative.

To reconstitute vacuum-dried BOTOX®, sterile normal saline without a preservative; (0.9% Sodium Chloride Injection) is used by drawing up the proper amount of diluent in the appropriate size syringe. Since BOTOX® may be denatured by bubbling or similar violent agitation, the diluent is gently injected into the vial. For sterility reasons BOTOX® is preferably administered within four hours after the vial is removed from the freezer and reconstituted. During these four hours, reconstituted BOTOX® can be stored in a refrigerator at about 2° C. to about 8° C. Reconstituted, refrigerated BOTOX® has been reported to retain its potency for at least about two weeks. *Neurology*, 48:249–53:1997.

Botulism or *botulinum* toxin intoxication is a potentially lethal disease caused by certain serotypes of neurotoxic proteins usually produced by *Clostridium botulinum*. Five different forms of botulism are known: 1) foodborne botulism, caused by ingestion of contaminated food, 2) wound botulism, caused by infection of wounds and increasingly observed in intravenous drug users, 3) infant botulism, the most frequent form, resulting from ingestion of *C. botulinum* and its colonization in the intestine, 4) hidden botulism in adults with abnormal intestines, and 5) inadvertant botulism after treatments for movement disorders. Furthermore, botulism may also be affected by deliberate acts of terrorists. The symptoms of *botulinum* toxin intoxication includes acute symmetric, descending flaccid paralysis with prominent bulbar palsies, typically presenting within 12 to 72 hours after exposure.

Currently, a pentavalent vaccine that protects against active BoNT serotypes A–E and a separate monovalent vaccine that protects against active BoNT serotype F are available as Investigational New Drugs. However, there are numerous shortcomings associated with the toxoid vaccines.

For example, serious adverse response to the antitoxins, such as anaphylaxis, has been reported to occur in 2% of recipients.

Other methods of combating *botulinum* intoxication are under investigation—most of which involve the administration of an antigen for the production of antibodies against the toxin. For example, Simpson et al. reports an inactive BoNT that may be administered orally to stimulate production of antibody in a mammal. See U.S. Pat. No. 6,051,239, the disclosure of which is incorporated in its entirety herein by reference. These methods which rely on the production of antibodies are not very practical because they require the mammal to be vaccinated before becoming intoxicated with the toxin. For example, if a non-vaccinated mammal is intoxicated with *botulinum* toxin, the administration of an antigen (e.g., an inactive BoNT) to stimulate antibodies production against the active BoNT is futile because the production of antibodies by the mammal would not be timely enough to ward off the deleterious effects of active BoNT, which occur within about 12 to 72 hours.

Further, as the use of *botulinum* toxin is becoming more common and frequent, for example as a therapeutic, it is important to have safer and more effective toxins. For example, it is advantageous to have toxins that have reduced antigenicity and can clear the circulatory system quickly.

Thus, there is a continued need to have more effective drugs and methods for treating botulism. Additionally, there is a continued need to have safer, more effective botulinum toxins. The present invention provides for such improvements.

SUMMARY OF THE INVENTION

The present invention provides for effective methods of treating botulinum intoxication. In some embodiments, the methods of treating *botulinum* toxin intoxication in a mammal comprise administering to the mammal an effective amount of a rescue agent. In some embodiments, the rescue agent is effective to treat *botulinum* intoxication when it is administered to the mammal after the mammal is intoxicated by an active *botulinum*. In some embodiments, a rescue agent comprises at least one of an inactive *botulinum* toxin ("iBoNT"), a modified nontoxic nonhemagglutinin ("NTNH") or combinations thereof. In some embodiments, the iBoNT has a reduced antigenicity, for example, from being glycosylated. In some embodiments, the modified NTNH comprises a targeting moiety covalently linked to a NTNH.

The present invention also provides for glycosylated *botulinum* toxin and methods of using same. In some embodiments, the glycosylated *botulinum* toxin clears from the circulation faster than the same *botulinum* toxin which is not glycosylated. In some embodiments, the glycosylated *botulinum* toxin may be employed to treat muscular disorders, autonomic nervous system disorders and/or pain.

The present invention also provides for methods of making di-chain botulinum toxins. In some embodiments, the method comprises expressing a single chain botulinum toxin and a NTNH in a non-*Clostridium botulinum* cell, whereby the NTNH facilitates the nicking of the single chain toxin into a di-chain toxin.

Any feature or combination of features described herein are included within the scope of the present invention provided that the features included in any such combination are not mutually inconsistent as will be apparent from the context, this specification, and the knowledge of one of ordinary skill in the art.

Additional advantages and aspects of the present invention are apparent in the following detailed description and claims.

BRIEF DESCRIPTION OF THE DRAWINGS

FIG. 1 shows the regions of *botulinum* toxin type A for possible glycosylation (N-linked oligosaccharides). Sugars for glycosylation include: hexose (e.g., man., gal.), hexNAc (e.g., GlcNAc, GalNAc), deoxyhexose (e.g., fucose), NeuAc, NeuGc, pentose (e.g., xylose), KDN, and HexA (e.g., glucuronic acid).

FIG. 2 shows the regions of *botulinum* toxin type A for possible glycosylation (O-linked oligosaccharides). Sugars for glycosylation include: hexose (e.g., man., gal.), hexNAc (e.g., GlcNAc, GalNAc), deoxyhexose (e.g., fucose), NeuAc, NeuGc, pentose (e.g., xylose), KDN, and HexA (e.g., glucuronic acid).

FIG. 4 shows expression of BoNT/A-LC in insect cells with baculovirus expression system, wherein BoNT/A-LC is specifically recognized by both anti-BoNT/A-LC pAb and His-tag mAb. Upper panel: anti-His-tag mAb; lower panel: anti-LC/A pAb.

FIG. 6 shows full length inactive BoNT/A (iBoNT/A) expressed in insect cells with baculovirus expression system. iBoNT/A is specifically recognized by both anti-BoNT/A-LC pAb and anti-toxin/A pAb, indicating that BEVS has the capacity of expressing full length BoNT.

FIG. 7 shows BoNT/A-HC Expressed in baculovirus expression system is specifically recognized by either anti-toxin pAb or anti-his-tag mAb.

FIG. 8 shows BoNT/A-LC or iBoNT/A expressed in baculovirus expression system, wherein BoNT/A-LC and iBoNT/A is specifically recognized by either anti-toxin-LC pAb or anti-toxin-A pAb, respectively.

FIG. 9 shows that iBoNT/A and iBoNT/A-LC are inactive indicated by the GFP—SNAP25 cleavage enzymatic activity assay.

FIG. 10 shows the amino acid sequence (SEQ ID NO:4) for iBoNT/A-Hall (Allergan) (H227Y)-His6 baculovirus expression vector system (rec-iBoNT/A (H227Y)-His6). This rec-iBoNT/A is recognized by Anti-Toxin polyclonal antibody.

FIG. 11 shows that BEVS-expressed rec-iBoNT/A (H227Y)-His6 has a different mobility from the native Clostridial-produced BoNT/A pure A, which may indicate that the BEVS-expressed rec-iBoNT/A (H227Y)-His6 is glycosylated in insect cells.

DEFINITIONS

Figure 3:
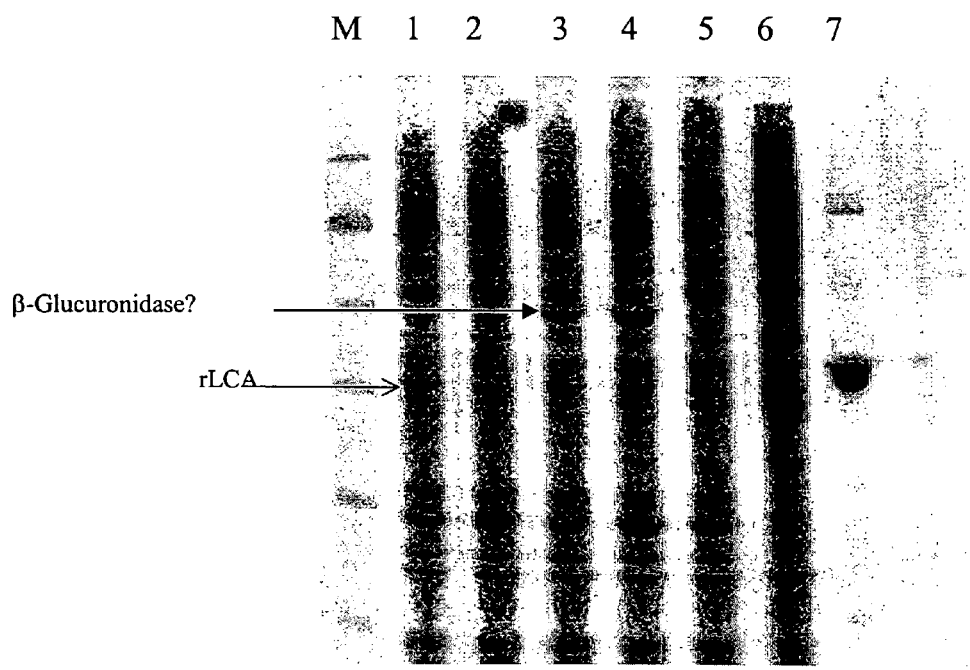
FIG. 3 shows the expression of BoNT/A-LC in insect cells with baculovirus expression system: SDS-PAGE: Coomassie blue stain.

The term "rescue agent" means any molecule that is effective to compete (directly or indirectly) with an active *botulinum* toxin, and thereby neutralizes the intoxicating effects of the active *botulinum* toxin. For example, a rescue agent may comprise an iBoNT that can compete with the active *botulinum* toxin at receptor sites on a nerve ending, and prevent the active *botulinum* toxin from entering into the nerve ending. Rescue agents comprising iBoNTs have reduced antigenicity, e.g., the iBoNT have reduced antigenicity. In accordance with the present invention, rescue agents comprising an iBoNT which does not have reduced antigenicity is to be administered to the mammal for treatment after the mammal has become exposed to *botulinum* toxin intoxication. The term "rescue agent" also means any molecule that can bind to the active *botulinum* toxin and facilitate its removal from the circulatory system. For example, a rescue agent may comprise a modified NTNH that can bind to the active *botulinum* toxin to form a complex, whereby the complex is cleared by the liver and/or kidney. As used herein, "rescue agents" exclude antigenic iBoNTs that are administered prior to *botulinum* toxin intoxication, antibodies/antitoxins to *botulinum* toxins, gamma globulins, human hyperimmune globulins, metalloprotease inhibitors (e.g. BABIM), 3,4-diaminopyridines (3,4-DAP), The excluded rescue agents are not part of the present invention because they are not very effective, e.g., they neutralize the *botulinum* toxins too slowly, have very low affinity to the toxins, and/or does not effectively facilitate the clearance of the toxins.

The term "*botulinum* toxin intoxication" means a condition caused by one or more of the seven serotypes of active *botulinum* toxins usually produced by *Clostridium botulinum*. The symptoms of *botulinum* toxin intoxication include acute symmetric, descending flaccid paralysis with prominent bulbar palsies, typically presenting within 12 to 72 hours after exposure. *Botulinum* toxin intoxication may be fatal if it is not properly treated.

The term "*botulinum* toxin" ("BoNT") means active or inactive *botulinum* toxin, unless it is specifically designated as inactive *botulinum* toxin ("iBoNT) or active BoNT. The term "*botulinum* toxin" also means a single chain *botulinum* toxin or a di-chain botulinum toxin, unless it is specifically designated.

The term "single chain *botulinum* toxin" means a *botulinum* toxin having a light chain and a heavy chain being within a single peptide.

The term "di-chain *botulinum* toxin" means a *botulinum* toxin having a light chain on one peptide, and a heavy chain on another peptide, wherein the light chain and the heavy chain are linked by a disulfide bond.

The term "heavy chain" means the heavy chain of a *botulinum* toxin. It has a molecular weight of about 100 kDa and can be referred to herein as heavy chain or as H.

The term "$H_N$" means a fragment (having a molecular weight of about 50 kDa) derived from the Heavy chain of a *botulinum* toxin, which is approximately equivalent to the amino terminal segment of the Heavy chain, or the portion corresponding to that fragment in the intact Heavy chain. It is believed to contain the portion of the natural or wild type botulinum toxin involved in the translocation of the light chain across an intracellular endosomal membrane.

The term "$H_C$" means a fragment (about 50 kDa) derived from the Heavy chain of a botulinum toxin which is approximately equivalent to the carboxyl terminal segment of the Heavy chain, or the portion corresponding to that fragment in the intact Heavy chain. It is believed to be immunogenic and to contain the portion of the natural or wild type botulinum toxin involved in high affinity binding to various neurons (including motor neurons), and other types of target cells.

The term "light chain" means the light chain of a *botulinum* toxin. It has a molecular weight of about 50 kDa, and can be referred to as light chain, L or as the proteolytic domain (amino acid sequence) of a *botulinum* toxin. The light chain is believed to be effective as an inhibitor of exocytosis, including as an inhibitor of neurotransmitter (i.e. acetylcholine) release when the light chain is present in the cytoplasm of a target cell.

The term "active *botulinum* toxin" means a *botulinum* toxin that is capable of substantially inhibiting release of neurotransmitters from nerve terminals or cells. In some embodiments, the active *botulinum* toxins are di-chain, having a light chain and a heavy chain linked by a disulfide bond.

The term "inactive *botulinum* toxin" ("iBoNT") means a *botulinum* toxin that is not toxic to a cell. For example, an iBoNT has minimal or no ability to interfere with the release of neurotransmitters from a cell or nerve endings. In some embodiments, the iBoNT has less than about 50% of the neurotoxic effect (e.g., ability to inhibit release of neurotransmitter) of an identical BoNT that is active. For example, an iBoNT/A has less than about 50% of the neurotoxic effect of an identical BoNT/A that is active. In some embodiments, the iBoNT has less than about 25% of the neurotoxic effect of an identical BoNT that is active. In some embodiments, the iBoNT has less than about 10% of the neurotoxic effect of an identical BoNT that is active. In some embodiments, the iBoNT has less than about 5% of the neurotoxic effect of an identical BoNT that is active. Inactive *botulinum* toxins are well known to those skilled in the art. For example, see U.S. Pat. No. 6,051,239 to Simpson et al. In some embodiments, the iBoNT comprises a heavy chain and a light chain, wherein the light chain is mutated as to have minimal or no ability to interfere with the release of neurotransmitters from a cell or a nerve ending. In some embodiments, the heavy chain is modified as to reduce antigenicity. In some embodiments, iBoNT is a single chain peptide.

The term "reduced antigenicity" means the ability to induce the production of antibody in a mammal is minimal or non-existence. For example, molecules which are glycosylated have reduced antigenicity because they have minimal or no ability to induce an immune response for the production of antibody in a mammal. Also, epitope regions on a molecule are responsible for the induction of antibodies in a mammal. Thus, molecules with epitope regions mutated or deleted have reduced antigenicity because these regions are no longer present on the molecule to stimulate antibody production. For example, an iBoNT comprising a mutated or deleted epitope region within its heavy chain at the carboxy terminal (Hc) has reduced antigenicity (discussed below). In some embodiments, the administration of a glycosylated BoNT into a mammal induces less production of antibody as compared to an administration of an identical BoNT which is not glycosylated, by about 2-fold, preferably 4-fold, more preferably 8-fold or more.

The term "targeting moiety" means a molecule that is recognized by and binds to a transporter in the liver and/or kidney, wherein the transporter transports the molecule out of the circulatory system.

The term "mammal" as used herein includes, for example, humans, rats, rabbits, mice and dogs.

The term "local administration" means direct administration by a non-systemic route at or in the vicinity of the site of an affliction, disorder or perceived pain.

DESCRIPTION OF EMBODIMENTS

The present invention relates to rescue agents for use in the treatments of toxin intoxication—for example *botulinum* intoxication, which can result from food poisoning, an act of bioterrorism, or from accidental overdose in the course of treatment.

In some embodiments, one or more rescue agents may be administered after the exposure to the toxin. In some embodiments, the rescue agents do not rely on the production of antibodies to render therapeutic effects. As such, the rescue agents may be administered shortly before the intoxication and may still be effective to neutralize the deleterious effects of the active *botulinum* toxin.

In some embodiments, a rescue agent comprises an iBoNT. The iBoNT can be any inactive toxin. In some embodiments, the iBoNT include, but are not limited to, inactivated botulinum toxin types A, B, C$_1$, D, E, F, G and/or fragments thereof. The iBoNT employed in accordance with the present invention has minimal or no ability to interfere with the release of neurotransmitters from a cell or nerve endings. In some embodiments, the iBoNT comprises a heavy chain and a light chain, wherein the light chain is mutated as to have minimal or no ability to interfere with the release of neurotransmitters from a cell or a nerve ending. In some embodiments, the iBoNT is a single chain. In some embodiments, the iBoNT is a di-chain. In some embodiments, iBoNT is iBoNT/A having the amino acid SEQ ID NO:4 (FIG. 10).

In some embodiments, the iBoNT has reduced or no antigenicity. Reduction in antigenicity can be accomplished in many ways. Such toxins can comprise, for example, a modified or deleted Hc region. The antigenicity of the Hc region is reported in Atassi et al., Crit. Rev. Immunol., 1999, 19, 219–260, which is incorporated herein by reference in its entirety. Amino acids deemed critical or necessary for the antigenicity can be substituted for or deleted in order to reduce or eliminate antigenicity. Another method of reducing or eliminating antigenicity is through glycosylation, which is discussed in more detail below.

Preferably, the iBoNTs compete effectively with the active *botulinum* toxin, as to prevent the active *botulinum* toxin from intoxicating the mammal. In some embodiments, the iBoNT comprises a light chain having the amino acid sequence set forth in SEQ ID NO: 4.

Nontoxic nonhemagglutinin (NTNH) is a 130-kDa peptide which forms a complex with the *botulinum* toxin after the *botulinum* toxin is expressed in the anaerobic Clostridial botulinum. For BoNT/A-Hall, the NTNH may be 138 kDa. See for example, Zhang, Lin, Li and Aoki, *Complete DNA sequences o the botulinum neurotoxin complex of Clostridium botulinum type A-Hall (Allergan) strain, Gene* 351(2003): 21–32 (received Apr. 5, 2003 and accepted Jun. 24, 2003). Without wishing to limit the invention to any theory or mechanism of operation, it is believed that modified NTNH may act as a rescue agent by binding to the active *botulinum* toxin that is intoxicating the mammal and escorting it to the liver and/or kidney, wherein the modified NTNH/active BoNT complex is cleared out of the body. In some embodiments, the modified NTNH comprises an NTNH covalently linked to a targeting moiety. Non-limiting examples of targeting moieties include molecules that are recognized by transporters in the kidney and/or liver that can transport these molecules out of the circulatory system. Such transporters include the P-gp, MRP2, BSEP and ABC transporters.

In some embodiments, targeting moieties include molecules that are recognized by the ABC transporters. Non-limiting examples of the ABC transporter targeting moieties include verapamil, cyclosporin A, tamoxifen, valspodar, biricodar, tariquidar, zosuquidar, laniquidar, ONT-093, digoxin, digitalis or digitalis glycosides such as digitoxin, alpha-methyldigoxin, beta-acetyldigoxin and ouabain and mixtures thereof.

In some embodiments, the NTNH is covalently linked to the targeting moiety using chemical techniques commonly known in the art. For example, see Example 16 and U.S. Pat. No. 6,203,794 to Dolly et al., the disclosure of which is incorporated in its entirety by reference herein. In some embodiments, the NTNH and the targeting moiety are expressed as a fusion protein, using techniques know to one of ordinary skill in the art.

HA70 and HA34 are proteins are similar to NTNH in that each may bind to BoNT, as does NTNH. Accordingly, HA70 or HA34 may be linked to a targeting moiety to form a modified HA70 or a modified HA34, respectively. In some embodiments, the modified HA70 and/or modified HA34 may be used as rescue agents in a manner similar to the modified NTNH.

In some embodiments, the NTNH may be employed as rescue agents. For example, an NTNH comprising a protease site (native or non-native) that is capable of digesting BoNT may be used as a rescue agent in accordance with the present invention.

In some embodiments, the method of treating *botulinum* toxin intoxication in a mammal comprises administering to the mammal an effective amount of an iBoNT, modified NTNH, or a combination thereof.

In some embodiments, both iBoNT and modified NTNH are administered to the mammal. In some embodiments, the modified NTNH specifically binds to active botulinum toxin and does not bind to or has reduced binding to the iBoNT. As such, iBoNT should be different from the active BoNT (deletion of certain regions of iBoNT); active BoNT has a sequence/domain which is only recognized by the modified NTNH; modified active BoNT has a sequence/domain which is only recognized by the modified NTNH (for treating toxin overdose); NTNH has a protease activity that binds to active BoNT and cleave the active BoNT; NTNH has a sequestration domain that sequester BoNT to liver and kidney clearance.

The iBoNT, modified NTNH, or a combination thereof may be administered orally or intravenously. In some embodiments, the iBoNT, modified NTNH, or a combination thereof may be administered locally by injection. In some embodiments, iBoNT and/or modified NTNH may be prepared as oral formulations by methods known in the art. See for example, CA 02415712 (2003-01-10) to Frevert, the disclosure of which is incorporated in its entirety herein by reference.

An ordinarily skilled medical provider can determine the appropriate dose and frequency of administration(s) of iBoNT and/or modified NTNH to achieve an optimum clinical result. That is, one of ordinary skill in medicine would be able to administer the appropriate amount of the iBoNT and/or NTNH at the appropriate time(s) to effectively prevent or treat BoNT intoxication.

In some embodiments, the mammal being treated is additionally subjected to close respiratory monitoring and feeding by enteral tube or parenteral nutrition, intensive care, mechanical ventilation, and/or treatment of secondary infections.

Glycosylated Toxins:

The present invention is also directed to *botulinum* toxins, or fragments thereof, that are glycosylated. Hereinafter, glycostylated BoNT are referred to as "gBoNT." The fragments of the g-BoNTs include a light chain (LC) or a heavy chain (HC) of the g-BoNT. In some embodiments, the g-BoNT include, but are not limited to, active g-BoNT types A, B, $C_1$, D, E, F, G and/or fragments thereof. In some embodiments, the g-BoNT include, but are not limited to, g-iBoNT types A, B, $C_1$, D, E, F, G and/or fragments thereof. For example, active or inactive toxins that may be glycosylated include the toxins disclosed in U.S. patent application Ser. No. 10/163,106, the disclosure of which is hereby incorporated in its entirety by reference. iBoNT that may be glycosylated include the iBoNTs disclosed in U.S. Pat. No. 6,051,239, the disclosure of which is incorporated in its entirety herein by reference.

In a broad embodiment, a g-BoNT is produced biologically. For example, a nucleic acid sequence encoding a toxin may be inserted into a vector, wherein the vector is transfected into a host cell for expression. Accordingly, a nucleic acid sequence encoding an active BoNT and/or iBoNT may be expressed into active g-BoNT and/or g-iBoNT, respectively. In some embodiments, a nucleic acid sequence encoding an active BoNT/A and/or iBoNT/A may be expressed into an active g-BoNT/A and/or g-iBoNT/A, respectively. Non-limiting examples of nucleic acid sequences which encode for iBoNT include those that have mutations at the region encoding for a zinc binding motif in the light chain. For example, a wild type nucleic acid sequence comprising a sequence encoding the zinc binding motif His-Glu-x-x-His (SEQ ID NO: 1) may be mutated to express Gly-Thr-x-x-Asn, (SEQ ID NO: 2), wherein x is any amino acid. See U.S. Pat. No. 6,051,239, the disclosure of which is incorporated in its entirety herein by reference.

Any host cell may be used in accordance with this invention, as long as the host cell has the biological machinery to glycosylate the expressed toxin. In some embodiments, the host cell is capable of glycosylating the expressed toxin with at least one of an N-acetylglucosamine, mannose, glucose, galactose, fucose, sialic acid and/or an oligosaccharide comprising two or more of the identified saccharides. In some embodiments, eukaryotic systems may be used to produce g-BoNT, or fragments thereof. For example, yeast may be used to express large amounts of glycoprotein at low cost. However, a major draw back of using yeast is that both N- and O-glycosylation apparatus differs from that of higher eukaryotes. In some embodiments, mammalian cells are used as host for expression genes obtained from higher eukaryotes because the signal for synthesis, processing and secretion of these proteins are usually recognized by the cells. For example, Chinese Hamster Ovary (CHO) cells are very well known for production of eukaryotic proteins or glycoproteins, since these cells can grow either attached to the surface or in suspension and adapt well to growth in the absence of serum. Researchers have developed several CHO mutant cell lines carrying one or more glycosylation mutation/s. Stanley, P., Molecular and Cellular Biology, 9(2): 377–383 (1989). These mutant cell lines are called "Lec" for Lectin resistant. Stanley, P. et al., Cell, 6: 121–128 (1975). These cell lines lack one or more of the key enzymes involved in the glycosylation pathway, thus resulting in the production of glycoprotein with carbohydrates of defined structure and minimal heterogeneity. Lec-1 is one such cell line which lacks a key enzyme N-acetyl Glucosaminetransferase-1. The absence of this enzyme results in the inhibition of glycosylation pathway after the carbohydrates trim down to Man(2)GlcNAc(2), leading to production of reduced, but homogeneous glycosylation (Man=manose and GlcNAc=n-acetylglucosamine).

In some embodiments, the g-BoNT of the present invention may be expressed in insect cells. For example, baculovirus based expression system makes insect cell lines an ideal system for high-level transient expression of glycoproteins. Proteins that are N-glycosylated in vertebrate cells are also generally glycosylated in insect cells. The first step of N-glycosylation in insect cells is similar to that in vertebrates. Usually, the Man(9)GlcNaC(2) moiety is trimmed to shorter oligosaccharide structures of Man(3)GlcNAc(2) in both insect cells and vertebrates. In vertebrates, these shorter core structures serve as the framework for complex oligosaccharide synthesis, while in insect cells this additional, complex oligosaccharide synthesis does not appear to occur in many cases, thus leading to restricted and less heterogeneous glycosylation.

In some embodiments, an insect cell comprising a baculovirus is employed to express a g-BoNT or a g-iBoNT. In some embodiment, an insect cell comprising a baculovirus is employed to express an active g-BoNT/A, an active g-BoNT/A-LC, an active g-BoNT/A-HC, a g-iBoNT/A, a g-iBoNT/A-LC and/or a g-iBoNT/A-HC.

Sometimes the natural glycosylation system in insect cells may not meet the requirement of the complex glycosylation for protein therapeutics. In such a case, a special cell line may be used, such as Mimic Sf9 insect cell (available from Invitrogen, Carlsbad, Calif., USA) for high level expression of complex glycoproteins in insect cells. Hollister, J. et al., Biochemistry, 41:15093–15104 (2002); Hollister, J. et al., Glycobiology 11:1–9 (2001); Hollister, J. et al., Glycobiology, 8:473–480 (1998); Jarvis, D. et al., Curr Opin Biotechnol, 9:528–533 (1998); and Seo, N. S. et al., Protein Expr Purif, 22: 234–241. Briefly, mammalian cells require expensive media supplements and expression levels are relatively low when compared to expression in other hosts. Insect cells offer several advantages over mammalian cells—growth at room temperature, lower media costs, and production of high levels of recombinant protein. The disadvantage of using insect cells is that the majority of proteins produced do not exhibit the complex glycosylation seen in mammlian cells. This can affect protein function, structure, antigeniticity and stabililty. The Mimic Sf9 Insect Cell Line contains stably integrated mammalian glycosyltransferases, resulting in the production of biantennary N-glycans. Mimic Sf9 Insect Cells enable expression of proteins that are similar to what would be produced in mammalian cells, making them suitable for producing proteins to of the present invention.

In some embodiments, the g-BoNTs are glycosylated at one or more N-glycosylation sites of a *botulinum* toxin. For example, an N-glycosylation site include the consensus pattern Asn-Xaa-Ser/Thr. It is noted, however, that the presence of the consensus tripeptide is not sufficient to conclude that an asparagine residue is glycosylated, due to the fact that the folding of the protein plays an important role in the regulation of N-glycosylation. It has been shown that the presence of proline between Asn and Ser/Thr will inhibit N-glycosylation. This aspect has been confirmed by recent statistical analysis of glycosylation sites, which also shows that about 50% of the sites that have a proline C-terminal to Ser/Thr are not glycosylated. It is also noted that there are a few reported cases of glycosylation sites with the pattern Asn-Xaa-Cys.

In some embodiments, known glycosylation sites may be deleted or mutated to create a desirable glycosylation pattern on the g-BoNT. Various mutation techniques are known and may be employed in accordance with the present invention. For example, site directed mutagenesis can be used to change the N-glycosylation sites. Asn of Asn-X-Ser/Thr (consensus sequence for N-glycosylation site) can be changed to Gln, since Gln is structurally similar to Asnand it posses a single net charge also. Single, double and triple mutants of glycosylation may be generated to study the effect of specific glycosylation inhibition on protein expression and function.

For example, site directed mutagenesis is a useful technique which allows one of ordinary skill to specifically mutate a single base pair leading to change in amino acid (e.g., glycosylation site) and study its effect on the function of the enzyme or on activity of the protein. Change in molecular weight of the protein will provide the information about glycosylation at that particular site. If a protein has more than one glycosylation site, it will help in determining which oligosaccharide structure exists on which glycosylation site. These studies help figure out which glycosylation site is most important in activity of a protein and thus could provide some information about the protein's ligand binding site. Some of the studies include, for example, Chiang et al., Archives of Biochemistry and Biophysics, 352(2):207–213 (1998), which reported that glycosylation on either site of thrombane A2 receptor is sufficient for ligand recognition, but glycosylation on both sites is required to maintain binding affinity and specificity. Planquart et al., European Journal of Biochemistry, 262:644–651 (1999), reported that only one of the four glycosylation sites of HGL significantly influences the enzymatic activity and presence of carbohydrates on HGL might protect it from the digestive enzymes in the stomach. Fan et al., European Journal of Biochemistry 246:243–251 (1997), observed that three N-glycosylaton mutants showed reduced half-life and different degrees of inhibition of processing of their N-glycans. Also, they reported that mutants of one particular site abolished the enzymatic activity, eliminated cell-surface expression and prevented the dimerization of the DPPIV protein. In another report, solubility of the protein CIP was found to be linearly dependent on the number of carbohydrate residues attached. See also Tams et al., Biochimica et Biophysica Act 1432: 214–221 (1999).

In some embodiments, the g-BoNT is glycosylated at one or more O-glycosylation sites. O-glycosylation sites are usually found in helical segments which means they are uncommon in the beta-sheet structure. Currently, there is no known consensus pattern for an O-glycosylation site.

Crystal structure of BoNT/A-Allergan shows the potential sites of N-glycosylation on the surface as follows: 173-NLTR (SEQ ID NO: 106), 382-NYTI (SEQ ID NO: 107), 411-NFTK (SEQ ID NO: 108), 417-NFTG (SEQ ID NO: 109), 971-NNSG (SEQ ID NO: 110), 1010-NISD (SEQ ID NO: 111), 1198-NASQ (SEQ ID NO: 112), 1221-NLSQ (SEQ ID NO: 113). In some embodiments, g-BoNT/A (including g-iBoNT/A) is glycosylated at 173-NLTR (SEQ ID NO: 106), 382-NYTI (SEQ ID NO: 107), 411-NFTK (SEQ ID NO: 108), 417-NFTG (SEQ ID NO: 109), 971-NNSG (SEQ ID NO: 110), 1010-NISD (SEQ ID NO: 111), 1198-NASQ (SEQ ID NO: 112) and/or 1221-NLSQ (SEQ ID NO: 113). Potential sites of N-glycosylation for BoNT/E are as follows: 97-NLSG (SEQ ID NO: 114), 138-NGSG (SEQ ID NO: 115), 161-NSSN (SEQ ID NO: 116), 164-NISL (SEQ ID NO: 117), 365-NDSI (SEQ ID NO: 118), and 370-NISE (SEQ ID NO: 119). In some embodiments, g-BoNT/E (including g-iBoNT/E) is glycosylated at 97-NLSG (SEQ ID NO: 114), 138-NGSG (SEQ ID NO: 115), 161-NSSN (SEQ ID NO: 116), 164-NISL (SEQ ID NO: 117), 365-NDSI (SEQ ID NO: 118), and/or 370-NISE (SEQ ID NO: 119).

In some embodiments, BEVS-insect cells may glycosylate a protein in endoplasmic reticulum (ER) on its consensus Asn-X-Ser/Thr recognized in an appropriate context by oligosaccharyltransferase found in the ER and Golgi complex. Like most eukaryotic ERs, insect ER enzymes can attach at least a $Glc_3Man_9GlcNAc_2$ (molecular weight of about 2600 dalton). The $Glc_3Man_9GlcNAc_2$ is the core structure that serves as the framework for complex oligosaccharide synthesis involving further GlcNAc, Gal or sialic-acid additions.

In some embodiments, a g-BoNT (including g-iBoNT) of the present invention comprises more than one $Glc_3Man_9GlcNAc_2$, for example five to twenty $Glc_3Man_9GlcNAc_2$. In some embodiments, the glycosylation constitute more than about 2% of the g-BoNT (including g-iBoNT) by weight. In some embodiments, the glycosylation constitute more than about 5% of the g-BoNT (including g-iBoNT) by weight. In some embodiments, the glycosylation constitute more than about 10% of the g-BoNT (including g-iBoNT) by weight.

In some embodiments, the g-BoNT/A or g-iBoNT/A is about 150 kDa, and the glycosylation adds about 20 to 30 kDa to the protein. In some embodiments, the g-BoNT/A or the g-iBoNT/A has about eight to twelve $Glc_3Man_9GlcNAc_2$ (molecular weight of about 2600 dalton). In some embodiments, the g-BoNT/A or g-iBoNT/A is glycosylated with $Glc_3Man_9GlcNAc_2$ at positions 173-NLTR (SEQ ID NO: 106), 382-NYTI (SEQ ID NO: 107), 411-NFTK (SEQ ID NO: 108), 417-NFTG (SEQ ID NO: 109), 971-NNSG (SEQ ID NO: 110), 1010-NISD (SEQ ID NO: 111), 1198-NASQ (SEQ ID NO: 112), 1221-NLSQ (SEQ ID NO: 113).

In some embodiments, a toxin may be glycosylated chemically to form a g-BoNT. One of ordinary skill may refer to the following references as a guide to chemically glycosylating a toxin of the present invention: Sofia, M. J., 1:27–34 (1996); Meldal, M., 4:710–718 (1994); Meldal, M., et al., 41:250–260 (1993); Vetter, D., et al., 34: 60–63 (1995); Chan, T.-Y. et al., "Abstracts of Papers", 211th National Meeting of the American Chemical Society, New Orleans, La., March, 1996; American Chemical Society: Washington, D.C., 1996; MED 198; Allanson, N., et al. "Abstracts of Papers", 211th National Meeting of the American Chemical Society, New Orleans, La., March, 1996; American Chemical Society: Washington, D.C., 1996; MED 199.

In some embodiments, attaching a saccharide unit can be accomplished either by direct glycosylation of the toxin or by construction of a non-glycosidic linkage between the sugar and the toxin subunit. Construction of glycopeptide conjugates on the solid phase is the most developed of conjugate strategies for application to combinatorial constructions. In fact, the construction of several glycopeptide libraries has been reported. Two approaches which have been successful implemented for library generation are the "building blocks" and "convergent" strategies.

The "building blocks" approach uses preformed glycosylated amino acids and relies on the formation of the peptide bond between each amino acid. This approach allows diversity to be introduced by varying the nature of the glycosylated amino acid in a fashion similar to the generation of a standard peptide combinatorial library. The construction of glycopeptide libraries employing the building blocks strategy has been reported.

Successful demonstrations of the "convergent" approach for the construction of glycopeptides include the attachment of the sugar unit to the peptide through an amide bond construction. These demonstrations have either the peptide or the saccharide attached to the solid support. The alternative approach, requiring site-selective glycosylation of a polymer bound peptide, has not been successfully demonstrated for the formation of peptide conjugates.

One of ordinary skill in the art may also employ the emerging chemical GlycoConjugation/GlycoPEGylation technology for making glycoproteins and their mimetics to attach different molecules to BoNTs, again via the glycans.

Glycosylation and Clearance:

In some embodiments, the g-BoNTs are used to treat various conditions that may be treated with the traditional toxins. For example, a active g-BoNT may be used to treat muscular disorder, autonomic nervous system disorder and pain. Non-limiting examples of neuromuscular disorders that may be treated with a modified neurotoxin include strabismus, blepharospasm, spasmodic torticollis (cervical dystonia), oromandibular dystonia and spasmodic dysphonia (largyngeal dystonia). Non-limiting examples of autonomic nervous system disorders include rhinorrhea, otitis media, excessive salivation, asthma, chronic obstructive pulmonary disease (COPD), excessive stomach acid secretion, spastic colitis and excessive sweating. Non-limiting examples of pain which may be treated in accordance to the present invention include migraine headache pain that is associated with muscle spasm, vascular disturbances, neuralgia, neuropathy and pain associated with inflammation.

As with the traditional toxins, the active g-BoNTs would be administered locally, e.g., intramuscularly, to render a localized effect. However, if the locally administered active toxin or active g-BoNT accidentally enters into the circulatory system, the active g-BoNT is advantageous over the active non-glycosylated toxin in that it will clear the circulatory system relatively quickly—minimizing potential systemic toxicity. In some embodiments, the active g-BoNTs clears the circulatory system faster than an identical active non-glycosylated toxin by a factor of 2, preferably 4, more preferably 8 or more. In some embodiments, the active g-BoNT clears the circulatory system faster than an identical active non-glycosylated BoNT by a factor of 2, preferably 4, more preferably 8 or more. In some embodiments, the active g-BoNT type A clears the circulatory system faster than an identical active non-glycosylated BoNT type A by a factor of 2, preferably 4, more preferably 8 or more.

Glycosylation Reduces Antigenicity:

Without wishing to limit the invention to any theory or mechanism of operation, it is believed that the absence of glycosylation in a protein leads to the formation of aggregates and the aggregates enhance immunogenicity. Thus, it is further believed that the presence of glycosylation reduces aggregation, resulting in reduced immunogenicity. Schellekens, H., Nat Rev Drug-Discov 1, 457–462 (2002), and Schellekens, H., Clin Ther 24, 1720–1740 (2002).

Accordingly, g-BoNTs are more advantageous over an identical non-glycosylated toxin for use in the clinic, because repeated use of a non-glycosylated toxin will induce an immune response (which ultimately causes non-responsiveness); wherein the g-BoNT has reduced antigenicity, and the use of which will not substantially induce an immune response. Consequently, g-BoNTs may be employed more frequently and for a longer duration of time. In some embodiments, the administration of a g-BoNT into a mammal induces less production of antibody as compared to an administration of an identical toxin which is not glycosylated, by about 2-fold, preferably 4-fold, more preferably 8-fold or more. In some embodiments, the administration of a active g-BoNT into a mammal induces less production of antibody as compared to an administration of an identical active BoNT which is not glycosylated, by about 2-fold, preferably 4-fold, more preferably 8-fold or more. In some embodiments, the administration of an active g-BoNT/A into a mammal induces less production of antibody as compared to an administration of an identical active BoNT/A which is not glycosylated, by about 2-fold, preferably 4-fold, more preferably 8-fold or more.

In some embodiments, an active BoNT and an active g-BoNT are co-administered (sequentially or simultaneously) as therapeutics. For example, an active g-BoNT/A and an active g-BoNT/A may be co-administered (sequentially or simultaneously) to treat any of the conditions mentioned above.

Of course, an ordinarily skilled medical provider can determine the appropriate dose and frequency of administration(s) to achieve an optimum clinical result. That is, one of ordinary skill in medicine would be able to administer the appropriate amount of the of active g-BoNT at the appropriate time(s) to effectively treat a condition. The dose of the g-BoNT to be administered depends upon a variety of factors, including the severity of the condition. The dose of the g-BoNTs employed in accordance with this invention may be equivalent to the dose of BOTOX® used in accordance with the present invention described herein. In the various methods of the present invention, a g-BoNT at a dose equivalent to about 0.1 U/kg to about 15 U/kg, of a BOTOX®, e.g., *botulinum* toxin type A, can be administered effectively as a therapeutic. In some embodiments, a g-BoNT at a dose equivalent to about 1 U/kg to about 20 U/kg of BOTOX® may be administered effectively as a therapeutic.

g-BoNTs that are inactive may also be administered to prevent or treat the intoxicating effects of an active toxin. The use of g-iBoNT to neutralize a toxin does not rely on the production of antibodies. This is advantageous because the g-iBoNT will compete and neutralize the toxin immediately, wherein it would take a long time for the inactive toxin to induce antibody production after it is administered to the mammal. For example, in the event that a treating physician accidentally administers too much of a toxin during an office treatment, it would be advantageous to administer g-iBoNT (as an antidote) to neutralize the overdosed toxins immediately.

In some embodiments, a g-iBoNT is administered (as an antidote) to prevent or treat the intoxicating effects of an active BoNT. For example, an inactive g-iBoNT/A may be administered, e.g, systemically, to prevent or treat the intoxicating effects of an active BoNT/A. In some embodiments, multiple g-iBoNT types are co-administered to prevent or treat the intoxicating effects of an active BoNT. For example, a combination of inactive g-iBoNT/A, B, C, D, E, F and/or G may be administered, e.g, systemically, to prevent or treat the intoxicating effects of an active BoNT. Primarily, there are three main types of BoNT intoxifications: food borne, infant and wound botulism. And unfortunately, there is a fourth type of BoNT intoxification: bioterrorism. Foodborne botulism occurs when a person ingests pre-formed toxin that leads to illness within a few hours to days. Foodborne botulism is a public health emergency because the contaminated food may still be available to other persons besides the patient. With foodborne botulism, symptoms begin within 6 hours to 2 weeks (most commonly between 12 and 36 hours) after eating toxin-containing food. Symptoms of botulism include double vision, blurred vision, drooping eyelids, slurred speech, difficulty swallowing, dry mouth, muscle weakness that always descends through the body: first shoulders are affected, then upper arms, lower arms, thighs, calves, etc. Paralysis of breathing muscles can cause a person to stop breathing and die, unless assistance with breathing (mechanical ventilation) is provided. Infant botulism occurs in a small number of susceptible infants each year who harbor *C. botulinum* in their intestinal tract. Wound botulism occurs when wounds are infected with *C. botulinum* that secretes the toxin. Deliberate bioterror BoNT intoxification may have the following features: outbreak of a large number of cases of acute flaccid paralysis with prominent bulbar palsies; outbreak with an unusual *botulinum* toxin type (e.g., types C, D, F, G or E toxins which are not acquired from an aquatic food; outbreak with a common geographic factor among cases (e.g., airport) but without a common dietary exposure (e.g., features suggestive of an aerosol attack); and multiple simultaneous outbreaks with no common source. In the case of a bioterror intoxification, it is advantageous to administer multiple types of g-iBoNT to ensure efficient detoxification.

An ordinarily skilled medical provider can determine the appropriate dose and frequency of administration(s) to achieve an optimum clinical result. That is, one of ordinary skill in medicine would be able to administer the appropriate amount of the g-iBoNT at the appropriate time(s) to effectively prevent or treat BoNT intoxication.

Glycosylation Increases Half-life:

Without wishing to limit the invention to any theory or mechanism of operation, it is believed that glycosylation of a protein leads to increased half-life, e.g., stability of the compound in the circulatory system. For example, the production of Aranesp™, a clinically proven protein therapeutics, involves the use of oligosacharide. Aranesp™ is an erythropoiesis stimulating protein that stimulates red blood cell (RBC) production, approved in the United States by the Food and Drug Administration (FDA). Aranesp™ is approved for the treatment of chemotherapy-induced anemia in patients with nonmyeloid malignancies (July 2002), and the treatment of anemia associated with chronic renal failure, including patients on dialysis and patients not on dialysis (September 2001). Aranesp™ works by stimulating the production of oxygen-transporting RBCs. Aranesp™ has a half-life approximately three times longer than the existing standard therapy. Epoetin alfa, marketed as EPOGEN®i for anemic dialysis patients and as Procrit®ii for cancer patients receiving chemotherapy and all other indications in the United States. Structurally, Aranesp™ differs from Epoetin alfa in that it has two additional N-linked sialic acid-containing carbohydrate chain. This results in an approximately three fold longer half-life, which leads to greater biological activity and more RBC production over time. The increased potency and longer half-life of Aranesp™ allows for less-frequent dosing compared with Epoetin alfa without compromising efficacy. Less-frequent dosing results in fewer injections for patients. It allows patients and caregivers to spend less time scheduling injection visits, and will free up physicians and nurses to attend to other patients and work activity.

As described above, a g-iBoNT may be administered (as a rescue agent) to prevent or treat the intoxicating effects of an active BoNT. For example, an inactive g-iBoNT/A may be administered, e.g, systemically, to prevent or treat the intoxicating effects of an active BoNT/A. Such use of g-iBoNT is additionally advantageous because the g-iBoNT would have an increased half-life as compared to the same iBoNT that is not glycosylated. Accordingly, the g-iBoNT is in the circulatory system longer to compete with the intoxicating active BoNT. In some embodiments, the g-iBoNT is not glycosylated at sites which would facilitate in its clearance from the system, e.g., via the liver or the kidney. In some embodiments, the g-iBoNT has a half-life that is greater than an iBoNT by about 2-fold, preferably about 4-fold, more preferably more than about 8-fold.

An ordinarily skilled medical provider can determine the appropriate dose and frequency of administration(s) to achieve an optimum clinical result. That is, one of ordinary skill in medicine would be able to administer the appropriate amount of the g-iBoNT at the appropriate time(s) to effectively prevent or treat BoNT intoxication.

Although examples of routes of administration and dosage are provided, the appropriate route of administration and dosage are generally determined on a case by case basis by the attending physician. Such determinations are routine to one of ordinary skill in the art (see for example, *Harrison's Principles of Internal Medicine* (1998), edited by Anthony Fauci et al., 14$^{th}$ edition, published by McGraw Hill).

The present invention also includes formulations which comprise at least one of the compositions disclosed herein, e.g, iBoNT, modified NTNH, active g-BoNT, g-iBoNT, etc. In some embodiments, the formulations comprise at least one of a iBoNT, modified NTNH, active g-BoNT and g-iBoNT in a pharmacologically acceptable carrier, such as sterile physiological saline, sterile saline with 0.1% gelatin, or sterile saline with 1.0 mg/ml bovine serum albumin.

The BoNT (e.g., active g-BoNT, g-iBoNT, and iBoNT) employed in the methods described above may be single chain toxins or di-chain toxins. The present invention also provides for methods of making a di-chain BoNT (e.g., di-chain g-BoNT, di-chain g-iBoNT, or di-chain iBoNT). BoNTs are initially synthesized as single chain toxin, and are then nicked, or cleaved, to form di-chain toxins. *Clostridium botulinum* bacteria, the bacteria that produce *botulinum* toxins, have endogenous proteases that nick the single chain toxins to form the di-chain toxins. For example, the bacterial strains that make active BoNT serotypes A, B, F and G possess endogenous proteases that can nick the single chain toxins. Workers in the field have also employed various proteases to nick the single chain. For example, single chain toxins may be nicked with immobilized TPCK-trypsin (Pierce, Rockford, Ill.) to produce di-chains. For example, see Simpson et al. U.S. Pat. No. 6,051,239, the disclosure of which is incorporated in its entirety herein by reference.

Sagane et al. recently reported that NTNH may cleave itself. Biochem Biophys Res Commun. 2002 Mar. 29;292 (2):434–40. More particularly, Sagane et al. reported that NTNH, in both isolated form and the neurotoxin/NTNHA complexed form, was prepared protease-free from toxin complexes produced by *Clostridium botulinum* type D strain 4947. NTNH in both preparations was found to be spontaneously converted to the nicked NTNH form leading to 15- and 115-kDa fragments with the excision of several amino acid residues at specific sites on SDS-PAGE during long-term incubation, while that of the eurotoxin/NTNH/hemagglutinin complexed form remained unnicked single-chain polypeptides under the same conditions. Considering that the NTNH preparation contained small amounts of the nicked form of NTNHA and the addition of trypsin accelerated the cleavage, it was speculated that a nicked form of NTNH remaining after the purification and/or NTNHA itself catalyzes the cleavage of intact NTNHA.

It is surprisingly discovered herein that NTNH contains a peptidase M27 motif. It is also surprisingly discovered herein that NTNH may facilitate in the nicking of a single chain botulinum toxin to form a di-chain *botulinum* toxin comprising a heavy chain and a light chain linked by a disulfide bond. Accordingly, the present invention provides for methods of making a di-chain *botulinum* toxin without using *Clostridium botulinum* bacteria. In some embodiments the di-chain toxin formed may be an active *botulinum* toxin. For example, the di-chain toxin formed in accordance with the present invention may be an active BoNT type A, B, C, D, E, F and/or G. In some embodiments, the di-chain toxin formed may be an active g-BoNT.

In some embodiments, the di-chain toxin formed may be a iBoNT. In some embodiments, the di-chain toxin formed in accordance with the present invention may be an iBoNT type A, B, C, D, E, F and/or G. In some embodiments, the di-chain toxin formed may be a g-iBoNT. For example, the di-chain toxin formed in accordance with the present invention may be an iBoNT type A, B, C, D, E, F and/or G.

In some embodiments, the method comprises the step of expressing a single chain botulinum toxin and a NTNH in a non-*Clostridium botulinum* cell, whereby the NTNH facilitates the nicking of the single chain toxin into a di-chain toxin. In some embodiments, the NTNH facilitates the nicking of the single chain toxin by directly cleaving the single chain to form a di-chain. In some embodiments, the NTNH facilitates the nicking of the single chain toxin by causing another peptidase to cleave the single chain to form the di-chain.

In some embodiments, the single chain *botulinum* toxin and a NTNH are expressed in cells comprising a vector which operatively harbors a nucleotide sequence encoding for the single chain toxin and a vector which operatively harbors a nucleotide sequence encoding for the NTNH. In some embodiments, the vector which operatively harbors a nucleotide sequence encoding for the single chain toxin also operatively harbors a nucleotide sequence encoding for the NTNH. Any vector systems may be employed in accordance with the present invention. In some embodiments, the vector may be baculovirus expression system. Other systems which may be employed in accordance with the present invention include: any prokaryotic and eukaryotic expression vector: pET, GST fusion, His-tag, myc-tag, GFP fusion, BFP fusion, or yeast, plant expression vectors.

The single chain toxin expressed may be any single chain *botulinum* toxin known in the art. For example, the single *botulinum* toxin expressed may be one reported by Simpson et al. in U.S. Pat. No. 6,051,239, the disclosure of which is incorporated in its entirety by reference herein. In some embodiments, the single chain *botulinum* toxin is the BoNT/A from the Hall strain.

Except for *Clostridium botulinum* cells, any cells may be employed in accordance with the present invention for forming a di-chain toxin. For example, prokaryotic cells or eukaryotic cells may be employed. In some embodiments, the eukaryotic cells that may be employed in accordance with the present invention include, but are not limited to, PC 12 cells, SHSY-5Y cells, HIT-T15 cells, HeLa cells and HEK293 cells, Neo2 cells, CHO cells, yeast and plant. In some embodiments, the di-chain BoNT made by eukaryotic cells are glycosylated. For example, the di-chain BoNT made by insect cells are glycosylated. In some embodiments, active di-chain BoNT made by insect cells are glycosylated. In some embodiments, di-chain iBoNT made by insect cells are glycosylated.

The method of using the expressed NTNH to facilitate the nicking of the expressed single chain toxin in a cell is capable of producing di-chains comprising a light chain and a heavy chain with the correct molecular weight. Moreover, this method is very efficient. In some embodiments, more than about 25% of the single chain toxin expressed in the cell is nicked. In some embodiments, more than 50% of the expressed single chain toxin is nicked. In some embodiments, more than 75% of the expressed single chain toxin is nicked. In some embodiments, more than 90%, for example 95%, of the single chain toxin is nicked.

The present invention also features a method of making a di-chain *botulinum* toxin in a cell free system. The method comprises the step of contacting a single chain botulinum toxin with NTNH in a media, whereby the NTNH facilitates the nicking of the single chain toxin into a di-chain toxin. The single chain *botulinum* toxin and NTNH may be obtained from any source. For example, the single chain toxin and/or NTNH may be expressed in a cell and are isolated from the cell by conventional means, e.g., lysing the cell to obtain the toxin and/or NTNH.

In some embodiments, a single chain toxin peptide and a NTNH are placed in a media, whereby the NTNH facilitates the nicking of the single chain toxin. In some embodiments, the media is a physiological solution. For example, the media may comprise the following (millimolar): NaCl (137), KCl (5), $CaCl_2$ (1.8), $MgSO_4$ (1.0), $NaHCO_3$ (24), $NaH_2PO_4$ (1), D-glucose (11). Any other formulations of physiological solutions are within the scope of the present invention. In some embodiments, the single chain toxin and the NTNH are incubated in the media for about 30 minutes to 90 minutes. In some embodiments, the single chain toxin and the NTNH are incubated in the media at about 25 degree to about 35 degree Celsius.

The di-chain toxins formed from the single chain toxins may be purified by conventional techniques. For example, the expressed single chains may comprise fourteen additional amino acids (Arg-Gly-Ser-His-His-His-His-His-His-Gly-Ser-Gly-Thr (SEQ ID NO: 3) at the amino terminus. These additional amino acids will also be part of the di-chain toxin at the amino terminus one of the chains. The 6×His sequence within this fourteen amino acid segment may be used for purification and subsequent detection of synthesized protein. For example, the di-chain having these amino acids may be purified by affinity chromatography on Ni-NTA resin using the 6×His affinity tag. In some embodiments, specifically bound di-chains may be eluted with low pH (elution buffer Ph 4.5) and analyzed on SDS-PAGE. In some embodiments, the di-chain may be purified to a homogeneity of about more than 50%. In some embodiments, the di-chain may be purified to a homogeneity of about more than 75%. In some embodiment, the di-chain may be purified to a homogeneity of about more than 90%, for example 95%.

In some embodiments, the NTNH comprise a protease that is capable of cleaving the single chain BoNT to a dichain BoNT. For example, an NTNH of the present invention may comprise a trypsin. In some embodiments, the NTNH is engineered to have endokinase or Tev protease catalytic domain. Such engineered NTNH can nick the BoNT that is engineered to contain the cleavage sites by endokinase or Tev protease.

In order that the invention disclosed herein may be more efficiently understood, examples are provided below. It should be understood that these examples are for illustrative purposes only and are not to be construed as limiting the invention in any manner. Throughout these examples, molecular cloning reactions, and other standard recombinant DNA techniques, were carried out according to methods described in Maniatis et al., Molecular Cloning—A Laboratory Manual, 2nd ed., Cold Spring Harbor Press (1989), using commercially available reagents, except where otherwise noted.

EXAMPLES

Example 1

Expression of BoNT/A-LC in Insect Cells with Baculovirus Expression System

Methods: pBAC-1 and pBACgus-1 are baculovirus transfer vectors designed for simplified cloning and expression of target genes in insect cells. Both these two transfer vectors encode an optional C-terminal His tag fusion sequence, which is for easy purification of target protein. pBACgus-1 also carries the gus gene encoding beta-glucuronidase that serves as a reporter to verify recombinant virus.

Full-length iBoNT/A, LC, iLC were subcloned into pBAC-1 or pBACgus-1 vectors. For construction of inactive LC and inactive BoNT/A, the point mutant H227Y at LC of BoNT/A has been shown to abolish LC activity. Therefore, to make inactive full-length BoNT/A, we have introduced the mutant H227Y by PCR with the site mutagenesis Quick-Change XL kit (Stratagene, Calif.). The mutagenic oligonucleotide primers have been designed individually according to the desired mutation. The sense primer is 5'-GTA ACA TTA GCA CAT GAA CTT ATA TAT GCT GGA CAT AGA TTA TAT GGA ATA GCA ATT-3'(SEQ ID NO: 120). The antisense primer is 5'-AAT GCT ATT CCA ATA TAA TCT ATG TCC AGC ATA TAT AAG TTC ATG TGC TAA TGT TAC-3'(SEQ ID NO: 120). The positive clones were selected and confirmed by restriction enzymes digestion and DNA sequencing.

Expression of BoNT/A-LC in BEVS (1) Co-transfection of AcNPV with the transfer plasmid for generating recombinant baculovirus in vivo to make baculovirally-expressed BoNT/A-LC.

Each transfer vector contains a large tract of AcNPV sequence flanking the subcloning region to facilitate homologous recombination. Co-transfection of the transfer recombinant plasmid and *Autographa californica* nuclear polyhedrosis virus (AcNPV) DNA into insect Sf9 cells allows recombination between homologous sites, transferring the heterologous gene from the vector to the AcNPV DNA. AcNPV infection of Sf9 cells results in the shut-off of host gene expression allowing for a high rate of recombinant mRNA and protein production.

For each transfection, $1.25 \times 10^6$ exponentially growing Sf9 cells were seeded. The cells were allowed to attach to the plate for 20-min. During this 20-min incubation, the transfection mixture was prepared. A 500-ng of transfer plasmid LC/A gene, either wild type or mutant, 100-ng of linearized AcNPV, and 5 ul of Eufectin were respectively mixed in a sterile polystyrene tube. This DNA/Eufectin mixture was incubated at RT for 15 min. The medium instead of plasmid DNA was used as a negative control. After the DNA/Eufectin 15-min incubation was completed, 0.45 ml of room temperature medium (no antibiotics or serum) was added to the DNA/Eufectin mixture. The entire 0.5-ml of this mixture was added to the 1 ml of medium covering the cells in the plate. After 1-hour incubation at 27° C., 6 ml of medium containing 5% serum and antibiotics were added and the resultants were incubated at 27° C. for 5 days (1$^{st}$ run). The transfection samples were listed in the Table 1 below.

(2) Amplification of recombinant baculoviruses. High titer recombinant virus is critical for expression of a target protein. At the end of the 1$^{st}$ run transfection incubation, the medium containing recombinant viruses was harvested from each 60-mm dish and all the virus-containing media were used to infect fresh naïve cells. Fresh medium was used to replace the virus stock after 1 hour infection and the cells were further incubated at 27° C. for 5–7 days (2$^{nd}$ run amplification). Above steps were repeated until the titer of recombinant virus was high enough to express a detectable target protein. The virus stock was used for PCR to confirm the presence of the LC/A gene. The high-titered viruses were used to infect the insect Sf21 cells and the cell lysates were used to determine the presence of the LC/A protein.

(3) Determination of recombinant baculovirus by a reporter gene assay: beta-Glucuronidase enzymatic activity assay. The transfer vector pBACgus-1 carries the gus gene encoding enzyme beta-Glucuronidase under control of the late basic protein promoter ($P_{6.9}$), which serves as a reporter to verify recombinant viruses by using the enzymatic reaction with its substrate X-Gluc. About five days post-transfection of each run, a 100 µl sample of the medium from each dish was taken and combined with 5 µl substrate X-Gluc (20 mg/ml). After incubation of a few hours or over-night (lower titer of viruses), recombinant pBACgus-containing viruses expressing beta-Glucuronidase was indicated by the blue staining (FIG. 1).

(4) Determination of rBoNT/A-LC expression by SDS-PAGE, Western blotting by anti-LC/A antibody and anti-His-tag (tagged on LC/A gene) monoclonal antibody.

a) Expression of rLC/A indicated by SDS-PAGE and Coomassie blue staining.

Expression of BoNT/A-LC was assessed by separation using SDS-PAGE of total cell extracts followed with the Coomassie blue staining (FIG. 3). A potential target protein migrating with the right molecular weight (50 kDa) was revealed only in presence of the cells harboring the recombinant baculoviruses of BoNT/A-LC (lane 1–4, FIG. 3), which is absent in the cells without the recombinant baculoviruses (vector alone, lane 5, FIG. 3) or in the cells alone (cells alone control, lane 6, FIG. 3). Notice that a protein migrating as 62 kDa, present only in the cells harboring pBACgus-1/LC/A but not the cells with pBAC-1/LC/A or vector alone or cells alone, is likely the reporter beta-Glucuronidase.

Methods: The $2 \times 10^5$ cells (equal numbers of cells for all samples) were resuspended in 100 µl TE buffer (10 mM Tris-HCl, pH 8.0, 1 mM EDTA). 100 µl of 2× lysis buffer with reducing agent and proteinase inhibitors were mixed with the cell suspension. The mixture was heated at 95° C. for 5 min and immediately 20 µl of the above sample was loaded in each lane of the precast gel system (4–12% SDS-PAGE Nupage, Invitrogen). Notice that equal amount of proteins were loaded for all the lanes.

Example 2

Expression of BoNT/A-LC in Insect Cells with Baculovirus Expression System, wherein BoNT/A-LC is Specifically Recognized by Both anti-BoNT/A-LC pAb and His-tag mAb

Expression of rLC/A was confirmed by SDS-PAGE and Western blotting using specific anti-LC/A polyclonal antibody and specific anti-His-tag (tagged on the C-terminal LC/A gene) monoclonal antibody.

The expression of recombinant LC/A was further determined with a specific anti-LC/A polyclonal antibody (pAb) for Western blot analysis. Two duplicating protein blots were probed with either anti-LC polyclonal antibody (FIG. 4A) or anti-His tag monoclonal antibody (FIG. 4B). Both antibodies specifically recognized the 50-kDa protein only in rLC/

A-containing cells (lanes 1–4, not in vector alone or cell alone controls (lanes 5 and 6, FIG. 3).

The data clearly demonstrated that we have successfully expressed both wild type and inactive mutant rBoNT/A-LC in BEVS. The experiments also indicated that the expression of recombinant BoNT/A-LC is not toxic to insect cells and BEVS is a feasible system to express an active toxin.

Example 3

BoNT/A-LC Expressed in Insect Cells with Baculovirus Expression System, wherein BoNT/A-LC Specifically Cleaves the LC/A Specific Substrate SNAP25 as Shown by GFP-SNAP25 Cleavage Assay Evaluation of the endopeptidase enzymatic activity of rBoNT/A-LC, both wild type and inactive mutant, expressed in BEVS.

The endopeptidase enzymatic activity of both wild type and mutant rBoNT/A-LC was determined by GFP-SNAP cleavage assay. In principle, this is an in vitro fluorescence release assay for quantifying the protease activity of *botulinum* neurotoxins. It combines the ease and simplicity of a recombinant substrate with the sensitivity that can be obtained with a fluorescent signal. It is capable of measuring the activity of BoNT/A at low picomolar concentrations.

Briefly, the high titer of recombinant viruses containing either wild type LC/A or the inactive mutant LC/A from $3^{rd}$ run was used to infect the insect Sf21 cells. After 3 days post-infection, cells were harvested. $1.2 \times 10^6$ cells from each infection were pelleted and resuspended in 100 µl reaction buffer (50 mM HEPES, pH 7.4; 10 uM $ZnCl_2$; 0.1% (v/v) Tween-20; no DTT; protease inhibitor cocktail). Cells were lysed on ice for 45 min. After spin down the cell debris at 14,000 rpm for 10 min at 4° C., supernatant was collected and analyzed for protein concentration by the BCA assay. For each recombinant LC/A lysate, both 5 µl (3 ug) and 20 µl (12 ug) were diluted in toxin reaction buffer and added to black v-bottom 96-well plates (Whatman) in 25 ul aliquots. Reagents: 2×Toxin Rxn Buffer (100 mM HEPES, pH 7.2; 0.2%(v/v) TWEEN-20; 20 µM ZnCl2; 20 mM DTT).

Assay Rinse Buffer (50 mM HEPES, pH 7.4); 8M Guanadine Hydrochloride (Pierce); Co2+ Resin (Talon Superflow Metal Affinity Resin from BD Biosciences); GFP-SNAP25 (134–206) fusion protein substrate Purified.

Procedure of LC/A as a positive control: 100 µL R×n of 50 mM Hepes, pH 7.4, 10 mM DTT, 10 uM $ZnCl_2$, 0.1 mg/mL BSA, 60 µg GFP-SNAP-His, 0.0001–1.0 ug/mL rLC/A for 1 hr incubation; terminated by 8M Guanidine Hydrochloride (1 M final concentration); added 100 uL $Co^{2+}$ resin and incubated 15 min before spin and pass over resin twice. The eluted samples were assayed to measure the fluorescent unit by absorbance of an innovative microplate reader.

Figure 5:
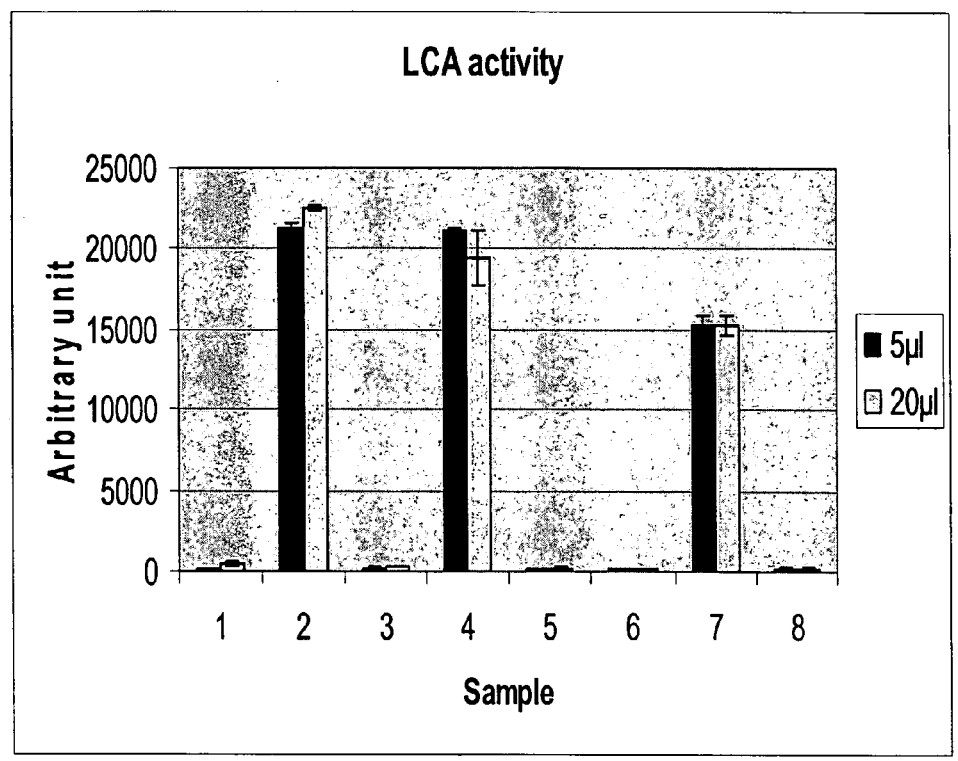
FIG. 5 shows BoNT/A-LC expressed in insect cells with baculovirus expression system, wherein BoNT/A-LC specifically cleaves the LC/A specific substrate SNAP25 as shown by GFP-SNAP25 cleavage assay, indicating that insect cells can survive with LC expression.

The endopeptidase enzymatic activity of baculovirally-expressed recombinant LC/A was shown in FIG. 5. The wild type LC/A, transfected in both transfer vectors pBAC-1 and pBACgus-1, showed significant high activity. There was no significant difference between the samples of 3 ug and 12 µg, suggesting that the activity of LC/A in 3 µg lysate reached the maximum. Whereas, little or no activity was shown in the inactive mutant LC/A, vector alone control, cells alone control, and substrate alone control, indicating that GFP-SNAP25 cleavage assay specifically detected the LC/A wild type. Taken together, the data of GFP-SNAP assay using the baculovirally-expressed LC/A demonstrated that active LC/A was successfully expressed in BEVS. As such, the wild type LC/A expressed in BEVS is endopeptidase enzymatically active while the inactive mutant LC was not active.

Example 4

Exemplary Methods for Preparing Recombinant Baculovirus Capable of Expressing a Glycosylated, Physiologically Inactive or Active *Botulinum* Toxin A in Insect Cells For high levels of expression of recombinant proteins bearing post-translational modifications such as glycosylated amino acids, insect cells can be infected with recombinant baculovirus encoding a gene of interest—here, a physiologically inactive form of the botulinum toxin A type (iBoNT/A)—and the insect cells grow and secrete the recombinant protein of interest directly into the culture medium. Thus, the recombinant, glycosylated protein can be recovered from the insect cell supernatant, saving time and money in the purification of recombinant proteins.

Using recombinant DNA technology, a transfer vector for use with baculovirus to infect *Spodoptera frugiperda* cells is constructed to contain the gene of interest (iBoNT/A cDNA). Ultimately, the iBoNT/A cDNA will be functionally linked to regulatory elements necessary for the expression of the protein in insect cells infected with the recombinant baculovirus; the iBoNT/A cDNA is placed under the control of the promoter for the polyhedrin gene of baculovirus. Toward this end, it is necessary to effect recombination between the transfer vector construct containing the gene of interest and the viral DNA to obtain a recombinant baculovirus. Transfer vector pVL1392 (Invitrogen Corporation), containing the regulatory regions of polyhedrin up- and down-stream from a polylinker containing various restriction is employed. First, appropriately spaced oligonucleotide primers encoding restriction endonuclease sites are used to amplify the iBoNT/A cDNA by PCR and create restriction sites to facilitate cloning into the transfer vector pVL1392. Next, this transfer vector construct is cotransfected into *Spodoptera frugiperda* cells together with the natural baculovirus AcMNPV (*Autographa californica* multiple nuclear polyhedrosis virus). The transfer vector is capable of introducing the sequence encoding the iBoNT/A protein into the genome of baculovirus, thereby producing a recombinant baculovirus. The recombinant baculovirus thus obtained, which carries the iBoNT/A cDNA under the control of the polyhedrin promoter and all the sequences involved in its synthesis, is purified and amplified, then used to infect cells of *Spodoptera frugiperda* in order to express this heterologous protein.

Methods of culturing insect cells for infection by baculovirus are well known to those working in this field. Procedures for their cultivation are disclosed in Summers, M. D. et al. 1987, EP Publication No. 127 839, and Smith G. E., U.S. Pat. No. 4,745,051. For the purpose of present invention, *Spodoptera frugiperda* Sf9 cells, which can be grown in monolayers or in suspension, are employed. *Spodoptera frugiperda* Sf21 cells can also be employed. Sf9 cell monolayers are incubated at 27° C. and divided twice or thrice per week, when they reach confluence. Conditions required by cultures in suspension depend on the culture medium and the volume of the culture.

Details of the methods employed to isolate the recombinant virus are well known to those skilled in the art. Generally, 2 µg of DNA of the transfer vector carrying the DNA coding for iBoNT/A and 1 μg of AcMNPV viral DNA are cotransfected in a monolayer of *Spodoptera frugiperda* cells. The cells show viral occlusions after 3–4 days, and 10–50% of the cells are infected. The virus passes into the culture medium with a titer of about $10^7$–$10^8$, and of this, 0.1–0.5% are recombinant viruses. Once the supernatant has been obtained, purification of the recombinant virus can begin. The procedure consists of associating a limiting dilution with dot-blot hybridization. The cells are seeded in a 96-well dish at a concentration of $2\times10^4$ cells per well, and infected with serial dilutions of $10^{-1}$ to $10^{-8}$ of baculovirus-containing insect cell supernatant. The dishes are incubated at 27° C., and infection is monitored. After 8–10 days, the supernatant is transferred into another dish and the cells are lysed. The DNA from each well is transferred onto a nylon membrane (Hybond-N) using a dot-blot apparatus, and it is then fixed by ultraviolet light for 3 minutes. Once fixed, the fragment representing the iBoNT/A cDNA is detected by hybridization according to conventional techniques.

The viral supernatant corresponding to the positive clone is subjected to this procedure once more. Usually, three cycles of treatment produce a pure recombinant virus that no longer produces polyhedrin molecules, but only recombinant protein molecules. Once recombinant virus containing DNA encoding the iBoNT/A has been obtained, it is amplified and production is begun, and large quantities of glycosylated, iBoNT/A protein can be recovered from large scale cultures of insect cells.

The protein obtained from infected cells is analyzed by electrophoresis in polyacrylamide gels and by Western blotting using polyclonal antibodies and/or His-tag antibodies that recognize specific amino acid sequences within the *botulinum* toxin A type protein sequence or epitope tags for confirmation that the iBoNT/A has in fact been processed and glycosylated in *Spodoptera frugiperda* cells.

Furthermore, assays for biological activity of the expressed recombinant proteins, such as enzymatic cleavage assays, can also be conducted. Additionally, one of ordinary skill in the art would be able to adapt this protocol to making active g-BoNT.

Example 5

Exemplary Methods for Co-expressing NTNH and Active or iBoNT in Insect Cells

A second baculoviral construct expressing the NTNH gene can be used to coinfect the system of Example 10, whereby high levels of expression of recombinant *botulinum* toxin A and NTNH proteins are coexpressed. In some embodiments, the cells may be infected with the construct expressing the single chain BoNT and the construct expressing the NTNH simultaneously. In some embodiments, the cells may be infected with the construct expressing the single chain BoNT and the construct expressing the NTNH sequentially, in which the construct expressing the single chain BoNT may be infected before or after the construct expressing the NTNH.

Again using recombinant DNA technology, a transfer vector for use with baculovirus to infect *Spodoptera frugiperda* cells is constructed to contain the gene of interest (in this case, the gene encoding NTNH gene [residues 963–4556 of Genbank Accession U63808]). A recombinant baculovirus with the NTNH gene under the control of the promoter for the polyhedrin gene of baculovirus is obtained by recombination in the same manner as described in Example 10. The recombinant baculovirus expressing the NTNH gene thus obtained is purified and amplified, and along with the recombinant baculovirus expressing the iBoNT/A cDNA, both recombinant baculoviral vectors are then used to infect cells of *Spodoptera frugiperda* in order to express both heterologous proteins. The co-expression of the two proteins in insect cells should produce a properly nicked iBoNT/A protein.

Once expressed, the NTNH protein can nick the co-expressed *botulinum* toxin intracellularly. Moreover, the insect cells may grow and secrete the processed di-chain botulinum toxin of interest directly into the culture medium.

Example 6

Exemplary Methods for Treatment of Pain Associated with Muscle Disorder with Active g-BoNT An unfortunate 36 year old woman has a 15 year history of temporomandibular joint disease and chronic pain along the masseter and temporalis muscles. Fifteen years prior to evaluation she noted increased immobility of the jaw associated with pain and jaw opening and closing and tenderness along each side of her face. The left side is originally thought to be worse than the right. She is diagnosed as having temporomandibular joint (TMJ) dysfunction with subluxation of the joint and is treated with surgical orthoplasty meniscusectomy and condyle resection.

She continues to have difficulty with opening and closing her jaw after the surgical procedures and for this reason, several years later, a surgical procedure to replace prosthetic joints on both sides is performed. After the surgical procedure progressive spasms and deviation of the jaw ensues. Further surgical revision is performed subsequent to the original operation to correct prosthetic joint loosening. The jaw continues to exhibit considerable pain and immobility after these surgical procedures. The TMJ remained tender as well as the muscle itself. There are tender points over the temporomandibular joint as well as increased tone in the entire muscle. She is diagnosed as having post-surgical myofascial pain syndrome and is injected with 7 U/kg of the active g-BoNT into the masseter and temporalis muscles, preferably the active g-BoNT/A.

Several days after the injections she noted substantial improvement in her pain and reports that her jaw feels looser. This gradually improves over a 2 to 3 week period in which she notes increased ability to open the jaw and diminishing pain. The patient states that the pain is better than at any time in the last 4 years. The improved condition persists for up to 27 months after the original injection of the modified neurotoxin.

Example 7

Use of g-BoNT Shows a Fast Clearance Rate from Circulation

Recent studies have shown that glycosylated proteins can clear a circulatory system more quickly than their non-glycosylated counterparts. For example, Lucore et al., reported that glycosylation of tissue-type plaminogens facilitates clearance. *Biochemical determinants of clearance of tissue-type plasminogen activator from the circulation*, Circulation, 77: 906–914 (1988). Specifically, Lucore et al. studied the influences of glycosylation on clearance with enzymatically treated t-PA in which clearance was assessed with concomitant administration of selected neoglycoproteins that compete with t-PA for specific glycoprotein receptors. The role of an intact active catalytic site, as reflected by differences in clearance with and without prior treatment of t-PA with the protease inhibitor PPACK, was defined also. Their results indicate that clearance is altered by inhibition of the active site and that the nature and extent of glycosylation influence clearance as well. These findings suggest that mannose/N-acetylglucosamine-specific glycoprotein receptors expressed on hepatic reticuloendothelial cells participate in clearance of t-PA from the circulation but that galactose-specific glycoprotein receptors probably do not.

In an exemplary scenario, a 46 year old woman presents a shoulder-hand syndrome type pain, characteristic of a "shoulder-hand syndrome." The pain is particularly localized at the deltoid region. The patient is treated by a bolus injection of between about 0.05 U/kg to about 2 U/kg of a mixture of BOTOX® and active g-BoNT subcutaneously to the shoulder. The physician accidentally nicked a nearby artery with the injection needle, whereby the mixture of BOTOX® and active g-BoNT is introduced into the circulatory system. A therapeutically effective dose of active g-iBoNT is administered to neutralize the effects of BOTOX® and active g-BoNT. Blood levels of BOTOX® and active g-BoNT are also monitored. Test results show that active g-BoNT clears from the circulatory system more quickly than BOTOX®.

Example 8

Accidental Overdose in the Treatment of Postherpetic Neuralgia—Use of g-iBoNT as an Antidote The anaerobic, gram positive bacterium *Clostridium botulinum* produces a potent polypeptide neurotoxin, *botulinum* toxin. *Botulinum* toxin causes a neuroparalytic illness in humans and animals referred to as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The *botulinum* toxin can apparently pass unattenuated through the lining of the gut and attack peripheral motor neurons. Symptoms of *botulinum* toxin intoxication can progress from difficulty walking, swallowing, and speaking to paralysis of the respiratory muscles and death.

*Botulinum* toxin type A is the most lethal natural biological agent known to man. About 50 picograms of a commercially available *botulinum* toxin type A (purified neurotoxin complex) (Available from Allergan, Inc., of Irvine, Calif. under the tradename BOTOX® in 100 unit vials) is a $LD_{50}$ in mice (i.e. 1 unit). One unit of BOTOX® contains about 50 picograms (about 56 attomoles) of *botulinum* toxin type A complex. Interestingly, on a molar basis, *botulinum* toxin type A is about 1.8 billion times more lethal than diphtheria, about 600 million times more lethal than sodium cyanide, about 30 million times more lethal than cobra toxin and about 12 million times more lethal than cholera. Singh, *Critical Aspects of Bacterial Protein Toxins*, pages 63–84 (chapter 4) of Natural Toxins II, edited by B. R. Singh et al., Plenum Press, New York (1976) (where the stated $LD_{50}$ of botulinum toxin type A of 0.3 ng equals 1 U is corrected for the fact that about 0.05 ng of BOTOX® equals 1 unit). One unit (U) of *botulinum* toxin is defined as the $LD_{50}$ upon intraperitoneal injection into female Swiss Webster mice weighing 18 to 20 grams each.

Postherpetic neuralgia is one of the most intractable of chronic pain problems. Patients suffering this excruciatingly painful process often are elderly, have debilitating disease, and are not suitable for major interventional procedures. The diagnosis is readily made by the appearance of the healed lesions of herpes and by the patient's history. The pain is intense and emotionally distressing. Postherpetic neuralgia may occur any where, but is most often in the thorax.

In an exemplary scenario, a 76 year old man presents a postherpetic type pain. The pain is localized to the abdomen region. The patient is treated by a bolus injection of between about 0.05 U/kg to about 2 U/kg of a BOTOX® intradermally to the abdomen. The treating physician accidentally administers an excessive amount of BOTOX®. Upon realizing the error, the physician administers the same area with a therapeutically effective dose of g-iBoNT. The particular dose as well as the frequency of administrations g-iBoNT depends upon a variety of factors within the skill of the treating physician. Within 1–7 days after BOTOX® and corrective g-iBoNT administration, the patient's pain is substantially alleviated.

Example 9

Detoxification with g-iBoNT

Aerosol distribution of a BoNT can result in symptoms of botulism. For example. A pentavalent (ABCDE) *botulinum* toxoid is available from the Centers for Disease Control and Prevention, but its use may not be feasible as a propylaxis due to the need to wait for antibodies to be raised in the recipient before immunity can be conferred.

Thus, in terms of detoxification or post exposure treatments, the toxoid is unfeasible because it induces immunity over several months. Immediate immunity can be provided by passive administration of equinine *botulinum* antitoxin or by specific human hyperimmune globulin. However, these means of detoxification are not very effective. For example, a segment of the population is known to suffer from horse serum anaphylaxis with the administration of the equinine *botulinum* antitoxin.

g-iBoNT can play a significant role in the detoxification of the individuals contaminated with an active BoNT. In a clinical or emergency setting, injection of victims with g-iBoNT could provide enough competitive inhibition with active BoNT to minimize its effects. In some embodiments, g-iBoNT may be formulated in pills to allow safe, quick and easy access for a large patient population. Importantly, g-iBoNT is not expected to induce anaphylaxis because it has reduced antigenicity.

Example 10 g-iBoNT has Reduced Antigenicity

In general, the occurrence of immunogenicity is influenced by the properties of the immunogens, its molecular size and solubility, and adjuvants/carriers used in the formulation. Furthermore, host factors including genotype and concomitant disease associated with immune dysregulation, previous exposure to other therapeutic proteins that might cause cross reactivity, may also play a part. The route of administration may modify the host immune reaction. The intravenous, intraperitoneal, oral or aerosol route may favor tolerance, whereas subcutaneous or intradermal administration may mimic an active immunization. Repeated administration of an antigen will increase the likelihood of a strong immune response as compared to one-off treatment. Additionally, there has been some well-controlled studies that show a correlation between glycosylation and immunogenicity.

In an exemplary experiment, g-iBoNT/A is administered to two groups of Rhesus monkeys, each group having 4 monkeys. Group A monkeys are given subcutaneous injections and group B monkeys are given intravenous boluses. A control group having two monkeys are given active BoNT (3 units/kg, an equivalent of the g-iBoNT dosages given to monkeys of groups A and B) intravenously.

After 24 hours, all monkeys in experimental groups A and B show no sign of distress or impairment of neurological function. The control group monkeys are listless and show classic signs of botulism.

After 4 weeks, blood samples are extracted from monkeys of each group, and are analyzed for the presence of antibodies against active BoNT or g-iBoNT. Blood samples from monkeys in groups A and B contain no antibody against the injected g-iBoNT. However, the blood samples from the control group shows trace of antibodies against the active BoNT.

Example 11

Exemplary Methods of Linking a NTNH to a Targeting Moiety

The NTNH molecule is 1193 amino acids in length (GenPept Accession AAM75960). In accordance with the invention, an NTNH may be attached to a targeting moiety to form a modified NTNH. The NTNH upon which the targeting moiety is to be attached may be free from other attachments or may already be attached to another targeting moiety. Many approaches are known for linking chemical compounds to protein chains.

It is known that most molecules acting as substrates or binding molecules, such as the targeting moiety, have positions that are not sensitive to steric hindrance. In addition, the linkage process should not introduce chirality into the targeting moiety. Further, the linker and the targeting moiety should be attached through a covalent bond. The distance between the NTNH and the targeting moiety may be adjusted by the insertion of spacer components. Preferable spacers have functional groups capable of binding to the linker, targeting moiety and NTNH and serving to conjugate them. Preferred spacer components include:

1) $HOOC—(CH_2)_n—COOH$, where n=1–12, suitable for insertion at the amino terminal end of a peptide, to connect it with a linker on a targeting moiety.

2) $HO—(CH_2)_n—COOH$, where n>10, suitable for attachment at the amino terminal of a peptide to connect the L chain with a linker on a targeting moiety.

3) $(C_5H_6)_n$, where n>2, suitable for attachment to join the NTNH with a linker on the targeting moiety. The benzene rings provide a rigid spacer between the targeting moiety and NTNH. Of course, appropriate functional groups, for example as identified by X below, will be present on the benzene rings to link the drug and the NTNH.

Various linker types are envisioned. For example, in one type the targeting moiety-linker-NTNH molecule remains intact after introduction into the circulatory system.

In some embodiments, a cysteine residue is attached to the end of the NTNH molecule by methods well known in the art. For instance, the gene construct that expresses the NTNH protein can be mutated to express a cysteine residing at the N-terminal portion of the protein. A maleimide linker is then attached to the Cysteine residue by well known means.

In some embodiments, the linker is attached directly to the targeting moiety. A targeting moiety-X moiety can have the following groups wherein X may be, without limitation, OH, SH, $NH_2$, CONH, $CONH_2$, COOH, $COOR_{30}$ (where $R_{30}$ is an alkyl group). Of course, the proper group would not be in an active site or be sterically hindering. The following is an example of one reaction which would link the targeting moiety-X to the linker molecule.

targeting moiety-X $Br—CH_2$-Linker->targeting moiety-X—$CH_2$-Linker

Once the targeting moiety has a linker attached, the following reaction can be used to link the targeting moiety to the NTNH. In this reaction, the NTNH, preferably the NTNH has an accessible lysine group that is used as the attachment point for the targeting moiety. As discussed herein, an extra amino acid, such as lysine, can be readily added to the N-terminal portion of the NTNH gene and used as the attachment point for a targeting moiety. In the following reaction, sodium cyanoborohydride is used to attach the linker to the lysine group on the NTNH molecule.

targeting moiety-linker-CHO+$NaCNBH_3$+NTNH-Lys-> targeting moiety-linker-$CH_2$—NH-NTNH

Targeting moiety that are envisioned for use in the present invention include those that have a free —XH group and that can bind to liver and/or kidney transporters.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

What is claimed is:

1. A method of treating a *botulinum* toxin intoxication in a mammal, the method comprising the step of administering to the mammal an effective amount of a glycosylated inactive *botulinum* toxin, wherein the effective amount of the glycosylated inactive *botulinum* toxin is an amount of glycosylated inactive *botulinum* toxin sufficient to compete with an active *botulinum* toxin for:
   (a) binding to a cell surface receptor,
   (b) translocation through an endosomal membrane,
   (c) binding to the cleavage site of a SNAP-25 protein,
   (d) binding to the cleavage of a synaptobrevin (VAMP), or
   (e) binding to the cleavage site of a syntaxin,
   wherein the glycosylated inactive *botulinum* toxin has a mutated light chain,
   thereby reducing the ability of the active *botulinum* toxin to intoxicate a neuron.

2. The method of claim 1 wherein the mutated light chain is mutated in the zinc binding motif.

3. The method of claim 2 wherein the mutated light chain comprises a light chain having the amino acid sequence set forth in SEQ ID NO:4.

4. The method of claim 1 wherein the glycosylated inactive botulinum toxin has a reduced antigenicity.

5. The method of claim 1 wherein the glycosylated inactive botulinum toxin has a mutated heavy chain.

6. The method of claim 5 wherein the mutated heavy chain is mutated in the Hc region.

7. The method of claim 5 wherein the mutated heavy chain is mutated in the Hn region.

8. The method of claim 1 wherein the glycosylated inactive botulinum toxin is glycosylated chemically.

9. The method of claim 1 wherein the glycosylated inactive botulinum toxin is glycosylated by expression of the inactive *botulinum* toxin in a eukaryotic expression system.

10. The method of claim 9 wherein the eukaryotic expression system is a baculovirus expression system.

11. The method of claim 1 wherein the glycosylated inactive botulinum toxin is administered to the mammal after an exposure to an active botulinum toxin.

12. The method of claim 1 wherein the glycosylated inactive botulinum toxin is administered to the mammal before an exposure to an active botulinum toxin.

13. The method of claim 11 or 12 wherein administration of the glycosylated inactive *botulinum* toxin is administered orally.

14. The method of claim 11 or 12 wherein administration of the glycosylated inactive *botulinum* toxin is administered intravenously.

15. The method of claim 11 or 12 wherein administration of the glycosylated inactive *botulinum* toxin is administered locally.

16. The method of claim 1 wherein the glycosylated inactive botulinum toxin is selected from the group consisting of a *botulinum* toxin serotype A, a *botulinum* toxin serotype B, a *botulinum* toxin serotype C1, a *botulinum* toxin serotype D, a *botulinum* toxin serotype E, a *botulinum* toxin serotype F and a botulinum toxin serotype G.

* * * * *

SEQUENCE LISTING

<160> NUMBER OF SEQ ID NOS: 105

<210> SEQ ID NO 1
<211> LENGTH: 4
<212> TYPE: PRT
<213> ORGANISM: Artificial Sequence
<220> FEATURE:
<223> OTHER INFORMATION: chemically synthesized peptide
<220> FEATURE:
<221> NAME/KEY: MISC_FEATURE
<222> LOCATION: (2)..(3)
<223> OTHER INFORMATION: Xaa is any amino acid.

-continued

```
<400> SEQUENCE: 1

Glu Xaa Xaa His
1

<210> SEQ ID NO 2
<211> LENGTH: 5
<212> TYPE: PRT
<213> ORGANISM: Artificial sequence
<220> FEATURE:
<223> OTHER INFORMATION: chemically syntesized peptide
<220> FEATURE:
<221> NAME/KEY: MISC_FEATURE
<222> LOCATION: (3)..(4)
<223> OTHER INFORMATION: Xaa is any amino acid.

<400> SEQUENCE: 2

Gly Thr Xaa Xaa Asn
1               5

<210> SEQ ID NO 3
<211> LENGTH: 13
<212> TYPE: PRT
<213> ORGANISM: Artificial Sequence
<220> FEATURE:
<223> OTHER INFORMATION: chemically synthesized peptide

<400> SEQUENCE: 3

Arg Gly Ser His His His His His His Gly Ser Gly Thr
1               5                   10

<210> SEQ ID NO 4
<211> LENGTH: 1302
<212> TYPE: PRT
<213> ORGANISM: Clostridium botulinum

<400> SEQUENCE: 4

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190
```

-continued

```
Thr Phe Gly Phe Glu Glu Ser Leu Glu Val Asp Thr Asn Pro Leu Leu
        195                 200                 205
Gly Ala Gly Lys Phe Ala Thr Asp Pro Ala Val Thr Leu Ala His Glu
210                 215                 220
Leu Ile Tyr Ala Gly His Arg Leu Tyr Gly Ile Ala Ile Asn Pro Asn
225                 230                 235                 240
Arg Val Phe Lys Val Asn Thr Asn Ala Tyr Tyr Glu Met Ser Gly Leu
                245                 250                 255
Glu Val Ser Phe Glu Glu Leu Arg Thr Phe Gly Gly His Asp Ala Lys
            260                 265                 270
Phe Ile Asp Ser Leu Gln Glu Asn Glu Phe Arg Leu Tyr Tyr Asn
            275                 280                 285
Lys Phe Lys Asp Ile Ala Ser Thr Leu Asn Lys Ala Lys Ser Ile Val
290                 295                 300
Gly Thr Thr Ala Ser Leu Gln Tyr Met Lys Asn Val Phe Lys Glu Lys
305                 310                 315                 320
Tyr Leu Leu Ser Glu Asp Thr Ser Gly Lys Phe Ser Val Asp Lys Leu
                325                 330                 335
Lys Phe Asp Lys Leu Tyr Lys Met Leu Thr Glu Ile Tyr Thr Glu Asp
            340                 345                 350
Asn Phe Val Lys Phe Phe Lys Val Leu Asn Arg Lys Thr Tyr Leu Asn
            355                 360                 365
Phe Asp Lys Ala Val Phe Lys Ile Asn Ile Val Pro Lys Val Asn Tyr
370                 375                 380
Thr Ile Tyr Asp Gly Phe Asn Leu Arg Asn Thr Asn Leu Ala Ala Asn
385                 390                 395                 400
Phe Asn Gly Gln Asn Thr Glu Ile Asn Asn Met Asn Phe Thr Lys Leu
                405                 410                 415
Lys Asn Phe Thr Gly Leu Phe Glu Phe Tyr Lys Leu Leu Cys Val Arg
            420                 425                 430
Gly Ile Ile Thr Ser Lys Thr Lys Ser Leu Asp Lys Gly Tyr Asn Lys
            435                 440                 445
Ala Leu Asn Asp Leu Cys Ile Lys Val Asn Asn Trp Asp Leu Phe Phe
450                 455                 460
Ser Pro Ser Glu Asp Asn Phe Thr Asn Asp Leu Asn Lys Gly Glu Glu
465                 470                 475                 480
Ile Thr Ser Asp Thr Asn Ile Glu Ala Ala Glu Glu Asn Ile Ser Leu
                485                 490                 495
Asp Leu Ile Gln Gln Tyr Tyr Leu Thr Phe Asn Phe Asp Asn Glu Pro
            500                 505                 510
Glu Asn Ile Ser Ile Glu Asn Leu Ser Ser Asp Ile Ile Gly Gln Leu
            515                 520                 525
Glu Leu Met Pro Asn Ile Glu Arg Phe Pro Asn Gly Lys Lys Tyr Glu
530                 535                 540
Leu Asp Lys Tyr Thr Met Phe His Tyr Leu Arg Ala Gln Glu Phe Glu
545                 550                 555                 560
His Gly Lys Ser Arg Ile Ala Leu Thr Asn Ser Val Asn Glu Ala Leu
                565                 570                 575
Leu Asn Pro Ser Arg Val Tyr Thr Phe Phe Ser Ser Asp Tyr Val Lys
            580                 585                 590
Lys Val Asn Lys Ala Thr Glu Ala Ala Met Phe Leu Gly Trp Val Glu
            595                 600                 605
```

-continued

```
Gln Leu Val Tyr Asp Phe Thr Asp Glu Thr Ser Glu Val Ser Thr Thr
    610                 615                 620
Asp Lys Ile Ala Asp Ile Thr Ile Ile Pro Tyr Ile Gly Pro Ala
625                 630                 635                 640
Leu Asn Ile Gly Asn Met Leu Tyr Lys Asp Asp Phe Val Gly Ala Leu
                645                 650                 655
Ile Phe Ser Gly Ala Val Ile Leu Glu Phe Ile Pro Glu Ile Ala
            660                 665                 670
Ile Pro Val Leu Gly Thr Phe Ala Leu Val Ser Tyr Ile Ala Asn Lys
                675                 680                 685
Val Leu Thr Val Gln Thr Ile Asp Asn Ala Leu Ser Lys Arg Asn Glu
690                 695                 700
Lys Trp Asp Glu Val Tyr Lys Tyr Ile Val Thr Asn Trp Leu Ala Lys
705                 710                 715                 720
Val Asn Thr Gln Ile Asp Leu Ile Arg Lys Lys Met Lys Glu Ala Leu
                725                 730                 735
Glu Asn Gln Ala Glu Ala Thr Lys Ala Ile Ile Asn Tyr Gln Tyr Asn
                740                 745                 750
Gln Tyr Thr Glu Glu Lys Asn Asn Ile Asn Phe Asn Ile Asp Asp
                755                 760                 765
Leu Ser Ser Lys Leu Asn Glu Ser Ile Asn Lys Ala Met Ile Asn Ile
770                 775                 780
Asn Lys Phe Leu Asn Gln Cys Ser Val Ser Tyr Leu Met Asn Ser Met
785                 790                 795                 800
Ile Pro Tyr Gly Val Lys Arg Leu Glu Asp Phe Asp Ala Ser Leu Lys
                805                 810                 815
Asp Ala Leu Leu Lys Tyr Ile Tyr Asp Asn Arg Gly Thr Leu Ile Gly
                820                 825                 830
Gln Val Asp Arg Leu Lys Asp Lys Val Asn Asn Thr Leu Ser Thr Asp
            835                 840                 845
Ile Pro Phe Gln Leu Ser Lys Tyr Val Asp Asn Gln Arg Leu Leu Ser
850                 855                 860
Thr Phe Thr Glu Tyr Ile Lys Asn Ile Ile Asn Thr Ser Ile Leu Asn
865                 870                 875                 880
Leu Arg Tyr Glu Ser Asn His Leu Ile Asp Leu Ser Arg Tyr Ala Ser
                885                 890                 895
Lys Ile Asn Ile Gly Ser Lys Val Asn Phe Asp Pro Ile Asp Lys Asn
                900                 905                 910
Gln Ile Gln Leu Phe Asn Leu Glu Ser Ser Lys Ile Glu Val Ile Leu
            915                 920                 925
Lys Asn Ala Ile Val Tyr Asn Ser Met Tyr Glu Asn Phe Ser Thr Ser
930                 935                 940
Phe Trp Ile Arg Ile Pro Lys Tyr Phe Asn Ser Ile Ser Leu Asn Asn
945                 950                 955                 960
Glu Tyr Thr Ile Ile Asn Cys Met Glu Asn Asn Ser Gly Trp Lys Val
                965                 970                 975
Ser Leu Asn Tyr Gly Glu Ile Ile Trp Thr Leu Gln Asp Thr Gln Glu
            980                 985                 990
Ile Lys Gln Arg Val Val Phe Lys Tyr Ser Gln Met Ile Asn Ile Ser
            995                 1000                1005
Asp Tyr Ile Asn Arg Trp Ile Phe Val Thr Ile Thr Asn Asn Arg
    1010                1015                1020
```

-continued

```
Leu Asn Asn Ser Lys Ile Tyr Ile Asn Gly Arg Leu Ile Asp Gln
    1025                1030                1035

Lys Pro Ile Ser Asn Leu Gly Asn Ile His Ala Ser Asn Asn Ile
    1040                1045                1050

Met Phe Lys Leu Asp Gly Cys Arg Asp Thr His Arg Tyr Ile Trp
    1055                1060                1065

Ile Lys Tyr Phe Asn Leu Phe Asp Lys Glu Leu Asn Glu Lys Glu
    1070                1075                1080

Ile Lys Asp Leu Tyr Asp Asn Gln Ser Asn Ser Gly Ile Leu Lys
    1085                1090                1095

Asp Phe Trp Gly Asp Tyr Leu Gln Tyr Asp Lys Pro Tyr Tyr Met
    1100                1105                1110

Leu Asn Leu Tyr Asp Pro Asn Lys Tyr Val Asp Val Asn Asn Val
    1115                1120                1125

Gly Ile Arg Gly Tyr Met Tyr Leu Lys Gly Pro Arg Gly Ser Val
    1130                1135                1140

Met Thr Thr Asn Ile Tyr Leu Asn Ser Ser Leu Tyr Arg Gly Thr
    1145                1150                1155

Lys Phe Ile Ile Lys Lys Tyr Ala Ser Gly Asn Lys Asp Asn Ile
    1160                1165                1170

Val Arg Asn Asn Asp Arg Val Tyr Ile Asn Val Val Val Lys Asn
    1175                1180                1185

Lys Glu Tyr Arg Leu Ala Thr Asn Ala Ser Gln Ala Gly Val Glu
    1190                1195                1200

Lys Ile Leu Ser Ala Leu Glu Ile Pro Asp Val Gly Asn Leu Ser
    1205                1210                1215

Gln Val Val Val Met Lys Ser Lys Asn Asp Gln Gly Ile Thr Asn
    1220                1225                1230

Lys Cys Lys Met Asn Leu Gln Asp Asn Asn Gly Asn Asp Ile Gly
    1235                1240                1245

Phe Ile Gly Phe His Gln Phe Asn Asn Ile Ala Lys Leu Val Ala
    1250                1255                1260

Ser Asn Trp Tyr Asn Arg Gln Ile Glu Arg Ser Ser Arg Thr Leu
    1265                1270                1275

Gly Cys Ser Trp Glu Phe Ile Pro Val Asp Asp Gly Trp Gly Glu
    1280                1285                1290

Arg Pro Leu His His His His His His
    1295                1300

<210> SEQ ID NO 5
<211> LENGTH: 1296
<212> TYPE: PRT
<213> ORGANISM: Clostridium botulinum

<400> SEQUENCE: 5

Met Pro Phe Val Asn Lys Gln Phe Asn Tyr Lys Asp Pro Val Asn Gly
 1               5                  10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80
```

-continued

Asp Asn Glu Lys Asp Asn Tyr Leu Lys Gly Val Thr Lys Leu Phe Glu
            85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
            115                 120                 125

Val Ile Asp Thr Asn Cys Ile Asn Val Ile Gln Pro Asp Gly Ser Tyr
        130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
        210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
        290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
        370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
        435                 440                 445

Ala Leu Asn Asp Leu Cys Ile Lys Val Asn Asn Trp Asp Leu Phe Phe
        450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

```
Asp Leu Ile Gln Gln Tyr Tyr Leu Thr Phe Asn Phe Asp Asn Glu Pro
            500                 505                 510
Glu Asn Ile Ser Ile Glu Asn Leu Ser Ser Asp Ile Gly Gln Leu
        515                 520                 525
Glu Leu Met Pro Asn Ile Glu Arg Phe Pro Asn Gly Lys Lys Tyr Glu
    530                 535                 540
Leu Asp Lys Tyr Thr Met Phe His Tyr Leu Arg Ala Gln Glu Phe Glu
545                 550                 555                 560
His Gly Lys Ser Arg Ile Ala Leu Thr Asn Ser Val Asn Glu Ala Leu
                565                 570                 575
Leu Asn Pro Ser Arg Val Tyr Thr Phe Phe Ser Ser Asp Tyr Val Lys
            580                 585                 590
Lys Val Asn Lys Ala Thr Glu Ala Ala Met Phe Leu Gly Trp Val Glu
        595                 600                 605
Gln Leu Val Tyr Asp Phe Thr Asp Glu Thr Ser Glu Val Ser Thr Thr
    610                 615                 620
Asp Lys Ile Ala Asp Ile Thr Ile Ile Pro Tyr Ile Gly Pro Ala
625                 630                 635                 640
Leu Asn Ile Gly Asn Met Leu Tyr Lys Asp Asp Phe Val Gly Ala Leu
                645                 650                 655
Ile Phe Ser Gly Ala Val Ile Leu Leu Glu Phe Ile Pro Glu Ile Ala
            660                 665                 670
Ile Pro Val Leu Gly Thr Phe Ala Leu Val Ser Tyr Ile Ala Asn Lys
        675                 680                 685
Val Leu Thr Val Gln Thr Ile Asp Asn Ala Leu Ser Lys Arg Asn Glu
    690                 695                 700
Lys Trp Asp Glu Val Tyr Lys Tyr Ile Val Thr Asn Trp Leu Ala Lys
705                 710                 715                 720
Val Asn Thr Gln Ile Asp Leu Ile Arg Lys Lys Met Lys Glu Ala Leu
                725                 730                 735
Glu Asn Gln Ala Glu Ala Thr Lys Ala Ile Ile Asn Tyr Gln Tyr Asn
            740                 745                 750
Gln Tyr Thr Glu Glu Lys Asn Asn Ile Asn Phe Asn Ile Asp Asp
        755                 760                 765
Leu Ser Ser Lys Leu Asn Glu Ser Ile Asn Lys Ala Met Ile Asn Ile
    770                 775                 780
Asn Lys Phe Leu Asn Gln Cys Ser Val Ser Tyr Leu Met Asn Ser Met
785                 790                 795                 800
Ile Pro Tyr Gly Val Lys Arg Leu Glu Asp Phe Asp Ala Ser Leu Lys
                805                 810                 815
Asp Ala Leu Leu Lys Tyr Ile Tyr Asp Asn Arg Gly Thr Leu Ile Gly
            820                 825                 830
Gln Val Asp Arg Leu Lys Asp Lys Val Asn Asn Thr Leu Ser Thr Asp
        835                 840                 845
Ile Pro Phe Gln Leu Ser Lys Tyr Val Asp Asn Gln Arg Leu Leu Ser
    850                 855                 860
Thr Phe Thr Glu Tyr Ile Lys Asn Ile Ile Asn Thr Ser Ile Leu Asn
865                 870                 875                 880
Leu Arg Tyr Glu Ser Asn His Leu Ile Asp Leu Ser Arg Tyr Ala Ser
                885                 890                 895
Lys Ile Asn Ile Gly Ser Lys Val Asn Phe Asp Pro Ile Asp Lys Asn
            900                 905                 910
```

-continued

Gln Ile Gln Leu Phe Asn Leu Glu Ser Ser Lys Ile Glu Val Ile Leu
        915                 920                 925

Lys Asn Ala Ile Val Tyr Asn Ser Met Tyr Glu Asn Phe Ser Thr Ser
        930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Gly Asn Asn Ser Gly Trp Lys Val
                965                 970                 975

Ser Leu Asn Tyr Gly Glu Ile Ile Trp Thr Leu Gln Asp Thr Gln Glu
            980                 985                 990

Ile Lys Gln Arg Val Val Phe Lys Tyr Ser Gln Met Ile Asn Ile Ser
        995                 1000                1005

Asp Tyr Ile Asn Arg Trp Ile Phe Val Thr Ile Thr Asn Asn Arg
        1010                1015                1020

Leu Asn Asn Ser Lys Ile Tyr Ile Asn Gly Arg Leu Ile Asp Gln
        1025                1030                1035

Lys Pro Ile Ser Asn Leu Gly Asn Ile His Ala Ser Asn Asn Ile
        1040                1045                1050

Met Phe Lys Leu Asp Gly Cys Arg Asp Thr His Arg Tyr Ile Trp
        1055                1060                1065

Ile Lys Tyr Phe Asn Leu Phe Asp Lys Glu Leu Asn Glu Lys Glu
        1070                1075                1080

Ile Lys Asp Leu Tyr Asp Asn Gln Ser Asn Ser Gly Ile Leu Lys
        1085                1090                1095

Asp Phe Trp Gly Asp Tyr Leu Gln Tyr Asp Lys Pro Tyr Tyr Met
        1100                1105                1110

Leu Asn Leu Tyr Asp Pro Asn Lys Tyr Val Asp Val Asn Asn Val
        1115                1120                1125

Gly Ile Arg Gly Tyr Met Tyr Leu Lys Gly Pro Arg Gly Ser Val
        1130                1135                1140

Met Thr Thr Asn Ile Tyr Leu Asn Ser Ser Leu Tyr Arg Gly Thr
        1145                1150                1155

Lys Phe Ile Ile Lys Lys Tyr Ala Ser Gly Asn Lys Asp Asn Ile
        1160                1165                1170

Val Arg Asn Asn Asp Arg Val Tyr Ile Asn Val Val Val Lys Asn
        1175                1180                1185

Lys Glu Tyr Arg Leu Ala Thr Asn Ala Ser Gln Ala Gly Val Glu
        1190                1195                1200

Lys Ile Leu Ser Ala Leu Glu Ile Pro Asp Val Gly Asn Leu Ser
        1205                1210                1215

Gln Val Val Val Met Lys Ser Lys Asn Asp Gln Gly Ile Thr Asn
        1220                1225                1230

Lys Cys Lys Met Asn Leu Gln Asp Asn Asn Gly Asn Asp Ile Gly
        1235                1240                1245

Phe Ile Gly Phe His Gln Phe Asn Asn Ile Ala Lys Leu Val Ala
        1250                1255                1260

Ser Asn Trp Tyr Asn Arg Gln Ile Glu Arg Ser Ser Arg Thr Leu
        1265                1270                1275

Gly Cys Ser Trp Glu Phe Ile Pro Val Asp Asp Gly Trp Gly Glu
        1280                1285                1290

Arg Pro Leu
        1295

```
<210> SEQ ID NO 6
<211> LENGTH: 11
<212> TYPE: PRT
<213> ORGANISM: Artificial sequence
<220> FEATURE:
<223> OTHER INFORMATION: Peptide fragment (residues 167-177)

<400> SEQUENCE: 6

Ser Phe Gly His Glu Val Leu Asn Leu Thr Arg
1               5                   10

<210> SEQ ID NO 7
<211> LENGTH: 12
<212> TYPE: PRT
<213> ORGANISM: Artificial sequence
<220> FEATURE:
<223> OTHER INFORMATION: Peptide fragment (residues 382-393)

<400> SEQUENCE: 7

Val Asn Tyr Thr Ile Tyr Asp Gly Phe Asn Leu Arg
1               5                   10

<210> SEQ ID NO 8
<211> LENGTH: 22
<212> TYPE: PRT
<213> ORGANISM: Artificial sequence
<220> FEATURE:
<223> OTHER INFORMATION: Peptide fragment (residues 394-415)

<400> SEQUENCE: 8

Asn Thr Asn Leu Ala Ala Asn Phe Asn Gly Gln Asn Thr Glu Ile Asn
1               5                   10                  15

Asn Met Asn Phe Thr Lys
            20

<210> SEQ ID NO 9
<211> LENGTH: 10
<212> TYPE: PRT
<213> ORGANISM: Artificial Sequence
<220> FEATURE:
<223> OTHER INFORMATION: Peptide fragment (residues 418-427)

<400> SEQUENCE: 9

Asn Phe Thr Gly Leu Phe Glu Phe Tyr Lys
1               5                   10

<210> SEQ ID NO 10
<211> LENGTH: 21
<212> TYPE: PRT
<213> ORGANISM: Artificial sequence
<220> FEATURE:
<223> OTHER INFORMATION: Peptide fragment (residues 457-477)

<400> SEQUENCE: 10

Val Asn Asn Trp Asp Leu Phe Phe Ser Pro Ser Glu Asp Asn Phe Thr
1               5                   10                  15

Asn Asp Leu Asn Lys
            20

<210> SEQ ID NO 11
<211> LENGTH: 59
<212> TYPE: PRT
<213> ORGANISM: Artificial sequence
<220> FEATURE:
<223> OTHER INFORMATION: Peptide fragment (residues 478-536)
```

-continued

```
<400> SEQUENCE: 11

Gly Glu Glu Ile Thr Ser Asp Thr Asn Ile Glu Ala Ala Glu Glu Asn
1               5                   10                  15

Ile Ser Leu Asp Leu Ile Gln Gln Tyr Tyr Leu Thr Phe Asn Phe Asp
            20                  25                  30

Asn Glu Pro Glu Asn Ile Ser Ile Glu Asn Leu Ser Ser Asp Ile Ile
        35                  40                  45

Gly Gln Leu Glu Leu Met Pro Asn Ile Glu Arg
    50                  55

<210> SEQ ID NO 12
<211> LENGTH: 7
<212> TYPE: PRT
<213> ORGANISM: Artificial Sequence
<220> FEATURE:
<223> OTHER INFORMATION: Peptide fragment (residues 773-779)

<400> SEQUENCE: 12

Leu Asn Glu Ser Ile Asn Lys
1               5

<210> SEQ ID NO 13
<211> LENGTH: 20
<212> TYPE: PRT
<213> ORGANISM: Artificial Sequence
<220> FEATURE:
<223> OTHER INFORMATION: Peptide fragment (residues 787-806)

<400> SEQUENCE: 13

Phe Leu Asn Gln Cys Ser Val Ser Tyr Leu Met Asn Ser Met Ile Pro
1               5                   10                  15

Tyr Gly Val Lys
            20

<210> SEQ ID NO 14
<211> LENGTH: 15
<212> TYPE: PRT
<213> ORGANISM: Artificial Sequence
<220> FEATURE:
<223> OTHER INFORMATION: Peptide fragment (residues 841-855)

<400> SEQUENCE: 14

Val Asn Asn Thr Leu Ser Thr Asp Ile Pro Phe Gln Leu Ser Lys
1               5                   10                  15

<210> SEQ ID NO 15
<211> LENGTH: 11
<212> TYPE: PRT
<213> ORGANISM: Artificial Sequence
<220> FEATURE:
<223> OTHER INFORMATION: Peptide fragment (residues 872-882)

<400> SEQUENCE: 15

Asn Ile Ile Asn Thr Ser Ile Leu Asn Leu Arg
1               5                   10

<210> SEQ ID NO 16
<211> LENGTH: 19
<212> TYPE: PRT
<213> ORGANISM: Artificial Sequence
<220> FEATURE:
<223> OTHER INFORMATION: Peptide fragment (residues 930-948)
```

-continued

```
<400> SEQUENCE: 16

Asn Ala Ile Val Tyr Asn Ser Met Tyr Glu Asn Phe Ser Thr Ser Phe
1               5                   10                  15

Trp Ile Arg

<210> SEQ ID NO 17
<211> LENGTH: 24
<212> TYPE: PRT
<213> ORGANISM: Artificial Sequence
<220> FEATURE:
<223> OTHER INFORMATION: Peptide fragment (residues 952-975)

<400> SEQUENCE: 17

Tyr Phe Asn Ser Ile Ser Leu Asn Asn Glu Tyr Thr Ile Ile Asn Cys
1               5                   10                  15

Met Glu Asn Asn Ser Gly Trp Lys
            20

<210> SEQ ID NO 18
<211> LENGTH: 13
<212> TYPE: PRT
<213> ORGANISM: Artificial Sequence
<220> FEATURE:
<223> OTHER INFORMATION: Peptide fragment (residues 1001-1013)

<400> SEQUENCE: 18

Tyr Ser Gln Met Ile Asn Ile Ser Asp Tyr Ile Asn Arg
1               5                   10

<210> SEQ ID NO 19
<211> LENGTH: 5
<212> TYPE: PRT
<213> ORGANISM: Artificial Sequence
<220> FEATURE:
<223> OTHER INFORMATION: Peptide fragment (residues 1024-1028)

<400> SEQUENCE: 19

Leu Asn Asn Ser Lys
1               5

<210> SEQ ID NO 20
<211> LENGTH: 13
<212> TYPE: PRT
<213> ORGANISM: Artificial Sequence
<220> FEATURE:
<223> OTHER INFORMATION: Peptide fragment (residues 1086-1098)

<400> SEQUENCE: 20

Asp Leu Tyr Asp Asn Gln Ser Asn Ser Gly Ile Leu Lys
1               5                   10

<210> SEQ ID NO 21
<211> LENGTH: 16
<212> TYPE: PRT
<213> ORGANISM: Artificial Sequence
<220> FEATURE:
<223> OTHER INFORMATION: Peptide fragment (residues 1141-1156)

<400> SEQUENCE: 21

Gly Ser Val Met Thr Thr Asn Ile Tyr Leu Asn Ser Ser Leu Tyr Arg
1               5                   10                  15
```

-continued

```
<210> SEQ ID NO 22
<211> LENGTH: 12
<212> TYPE: PRT
<213> ORGANISM: Artificial Sequence
<220> FEATURE:
<223> OTHER INFORMATION: Peptide fragment (residues 1193-1204)

<400> SEQUENCE: 22

Leu Ala Thr Asn Ala Ser Gln Ala Gly Val Glu Lys
1               5                   10

<210> SEQ ID NO 23
<211> LENGTH: 20
<212> TYPE: PRT
<213> ORGANISM: Artificial Sequence
<220> FEATURE:
<223> OTHER INFORMATION: Peptide fragment (residues 1205-1224)

<400> SEQUENCE: 23

Ile Leu Ser Ala Leu Glu Ile Pro Asp Val Gly Asn Leu Ser Gln Val
1               5                   10                  15

Val Val Met Lys
            20

<210> SEQ ID NO 24
<211> LENGTH: 9
<212> TYPE: PRT
<213> ORGANISM: Artificial Sequence
<220> FEATURE:
<223> OTHER INFORMATION: Peptide fragment (residues 1261-1269)

<400> SEQUENCE: 24

Leu Val Ala Ser Asn Trp Tyr Asn Arg
1               5

<210> SEQ ID NO 25
<211> LENGTH: 21
<212> TYPE: PRT
<213> ORGANISM: Artificial Sequence
<220> FEATURE:
<223> OTHER INFORMATION: Peptide fragment (residues 20-40)

<400> SEQUENCE: 25

Val Asn Asn Trp Asp Leu Phe Phe Ser Pro Ser Glu Asp Asn Phe Thr
1               5                   10                  15

Asn Asp Leu Asn Lys
            20

<210> SEQ ID NO 26
<211> LENGTH: 59
<212> TYPE: PRT
<213> ORGANISM: Artificial Sequence
<220> FEATURE:
<223> OTHER INFORMATION: Peptide fragment (residues 41-99)

<400> SEQUENCE: 26

Gly Glu Glu Ile Thr Ser Asp Thr Asn Ile Glu Ala Ala Glu Glu Asn
1               5                   10                  15

Ile Ser Leu Asp Leu Ile Gln Gln Tyr Tyr Leu Thr Phe Asn Phe Asp
            20                  25                  30

Asn Glu Pro Glu Asn Ile Ser Ile Glu Asn Leu Ser Ser Asp Ile Ile
        35                  40                  45

Gly Gln Leu Glu Leu Met Pro Asn Ile Glu Arg
    50                  55
```

```
<210> SEQ ID NO 27
<211> LENGTH: 7
<212> TYPE: PRT
<213> ORGANISM: Artificial Sequence
<220> FEATURE:
<223> OTHER INFORMATION: Peptide fragment (residues 336-342)

<400> SEQUENCE: 27

Leu Asn Glu Ser Ile Asn Lys
1               5

<210> SEQ ID NO 28
<211> LENGTH: 20
<212> TYPE: PRT
<213> ORGANISM: Artificial Sequence
<220> FEATURE:
<223> OTHER INFORMATION: Peptide fragment (residues 350-369)

<400> SEQUENCE: 28

Phe Leu Asn Gln Cys Ser Val Ser Tyr Leu Met Asn Ser Met Ile Pro
1               5                   10                  15

Tyr Gly Val Lys
            20

<210> SEQ ID NO 29
<211> LENGTH: 15
<212> TYPE: PRT
<213> ORGANISM: Artificial Sequence
<220> FEATURE:
<223> OTHER INFORMATION: Peptide fragment (residues 404-418)

<400> SEQUENCE: 29

Val Asn Asn Thr Leu Ser Thr Asp Ile Pro Phe Gln Leu Ser Lys
1               5                   10                  15

<210> SEQ ID NO 30
<211> LENGTH: 11
<212> TYPE: PRT
<213> ORGANISM: Artificial Sequence
<220> FEATURE:
<223> OTHER INFORMATION: Peptide fragment (residues 435-445)

<400> SEQUENCE: 30

Asn Ile Ile Asn Thr Ser Ile Leu Asn Leu Arg
1               5                   10

<210> SEQ ID NO 31
<211> LENGTH: 19
<212> TYPE: PRT
<213> ORGANISM: Artificial Sequence
<220> FEATURE:
<223> OTHER INFORMATION: Peptide fragment (residues 493-511)

<400> SEQUENCE: 31

Asn Ala Ile Val Tyr Asn Ser Met Tyr Glu Asn Phe Ser Thr Ser Phe
1               5                   10                  15

Trp Ile Arg

<210> SEQ ID NO 32
<211> LENGTH: 24
<212> TYPE: PRT
<213> ORGANISM: Artificial Sequence
<220> FEATURE:
<223> OTHER INFORMATION: Peptide fragment (residues 515-538)
```

-continued

```
<400> SEQUENCE: 32

Tyr Phe Asn Ser Ile Ser Leu Asn Asn Glu Tyr Thr Ile Ile Asn Cys
1               5                   10                  15
Met Glu Asn Asn Ser Gly Trp Lys
            20

<210> SEQ ID NO 33
<211> LENGTH: 13
<212> TYPE: PRT
<213> ORGANISM: Artificial Sequence
<220> FEATURE:
<223> OTHER INFORMATION: Peptide fragment (residues 564-576)

<400> SEQUENCE: 33

Tyr Ser Gln Met Ile Asn Ile Ser Asp Tyr Ile Asn Arg
1               5                   10

<210> SEQ ID NO 34
<211> LENGTH: 5
<212> TYPE: PRT
<213> ORGANISM: Artificial Sequence
<220> FEATURE:
<223> OTHER INFORMATION: Peptide fragment (residues 587-591)

<400> SEQUENCE: 34

Leu Asn Asn Ser Lys
1               5

<210> SEQ ID NO 35
<211> LENGTH: 13
<212> TYPE: PRT
<213> ORGANISM: Artificial Sequence
<220> FEATURE:
<223> OTHER INFORMATION: Peptide fragment (residues 649-661)

<400> SEQUENCE: 35

Asp Leu Tyr Asp Asn Gln Ser Asn Ser Gly Ile Leu Lys
1               5                   10

<210> SEQ ID NO 36
<211> LENGTH: 16
<212> TYPE: PRT
<213> ORGANISM: Artificial Sequence
<220> FEATURE:
<223> OTHER INFORMATION: Peptide fragment (residues 704-719)

<400> SEQUENCE: 36

Gly Ser Val Met Thr Thr Asn Ile Tyr Leu Asn Ser Ser Leu Tyr Arg
1               5                   10                  15

<210> SEQ ID NO 37
<211> LENGTH: 12
<212> TYPE: PRT
<213> ORGANISM: Artificial Sequence
<220> FEATURE:
<223> OTHER INFORMATION: Peptide fragment (residues 756-767)

<400> SEQUENCE: 37

Leu Ala Thr Asn Ala Ser Gln Ala Gly Val Glu Lys
1               5                   10

<210> SEQ ID NO 38
<211> LENGTH: 20
<212> TYPE: PRT
<213> ORGANISM: Artificial Sequence
```

```
<220> FEATURE:
<223> OTHER INFORMATION: Peptide fragment (residues 768-787)

<400> SEQUENCE: 38

Ile Leu Ser Ala Leu Glu Ile Pro Asp Val Gly Asn Leu Ser Gln Val
1               5                  10                  15

Val Val Met Lys
            20

<210> SEQ ID NO 39
<211> LENGTH: 859
<212> TYPE: PRT
<213> ORGANISM: Clostridium botulinum

<400> SEQUENCE: 39

Lys Thr Lys Ser Leu Asp Lys Gly Tyr Asn Lys Ala Leu Asn Asp Leu
1               5                  10                  15

Cys Ile Lys Val Asn Asn Trp Asp Leu Phe Phe Ser Pro Ser Glu Asp
            20                  25                  30

Asn Phe Thr Asn Asp Leu Asn Lys Gly Glu Glu Ile Thr Ser Asp Thr
        35                  40                  45

Asn Ile Glu Ala Ala Glu Asn Ile Ser Leu Asp Leu Ile Gln Gln
    50                  55                  60

Tyr Tyr Leu Thr Phe Asn Phe Asp Asn Glu Pro Glu Asn Ile Ser Ile
65                  70                  75                  80

Glu Asn Leu Ser Ser Asp Ile Ile Gly Gln Leu Glu Leu Met Pro Asn
                85                  90                  95

Ile Glu Arg Phe Pro Asn Gly Lys Lys Tyr Glu Leu Asp Lys Tyr Thr
            100                 105                 110

Met Phe His Tyr Leu Arg Ala Gln Glu Phe Glu His Gly Lys Ser Arg
        115                 120                 125

Ile Ala Leu Thr Asn Ser Val Asn Glu Ala Leu Leu Asn Pro Ser Arg
    130                 135                 140

Val Tyr Thr Phe Phe Ser Ser Asp Tyr Val Lys Lys Val Asn Lys Ala
145                 150                 155                 160

Thr Glu Ala Ala Met Phe Leu Gly Trp Val Glu Gln Leu Val Tyr Asp
                165                 170                 175

Phe Thr Asp Glu Thr Ser Glu Val Ser Thr Thr Asp Lys Ile Ala Asp
            180                 185                 190

Ile Thr Ile Ile Ile Pro Tyr Ile Gly Pro Ala Leu Asn Ile Gly Asn
        195                 200                 205

Met Leu Tyr Lys Asp Asp Phe Val Gly Ala Leu Ile Phe Ser Gly Ala
    210                 215                 220

Val Ile Leu Leu Glu Phe Ile Pro Glu Ile Ala Ile Pro Val Leu Gly
225                 230                 235                 240

Thr Phe Ala Leu Val Ser Tyr Ile Ala Asn Lys Val Leu Thr Val Gln
                245                 250                 255

Thr Ile Asp Asn Ala Leu Ser Lys Arg Asn Glu Lys Trp Asp Glu Val
            260                 265                 270

Tyr Lys Tyr Ile Val Thr Asn Trp Leu Ala Lys Val Asn Thr Gln Ile
        275                 280                 285

Asp Leu Ile Arg Lys Lys Met Lys Glu Ala Leu Glu Asn Gln Ala Glu
    290                 295                 300

Ala Thr Lys Ala Ile Ile Asn Tyr Gln Tyr Asn Gln Tyr Thr Glu Glu
305                 310                 315                 320
```

-continued

```
Glu Lys Asn Asn Ile Asn Phe Asn Ile Asp Asp Leu Ser Ser Lys Leu
                325                 330                 335

Asn Glu Ser Ile Asn Lys Ala Met Ile Asn Ile Asn Lys Phe Leu Asn
            340                 345                 350

Gln Cys Ser Val Ser Tyr Leu Met Asn Ser Met Ile Pro Tyr Gly Val
        355                 360                 365

Lys Arg Leu Glu Asp Phe Asp Ala Ser Leu Lys Asp Ala Leu Leu Lys
    370                 375                 380

Tyr Ile Tyr Asp Asn Arg Gly Thr Leu Ile Gly Gln Val Asp Arg Leu
385                 390                 395                 400

Lys Asp Lys Val Asn Asn Thr Leu Ser Thr Asp Ile Pro Phe Gln Leu
                405                 410                 415

Ser Lys Tyr Val Asp Asn Gln Arg Leu Leu Ser Thr Phe Thr Glu Tyr
            420                 425                 430

Ile Lys Asn Ile Ile Asn Thr Ser Ile Leu Asn Leu Arg Tyr Glu Ser
        435                 440                 445

Asn His Leu Ile Asp Leu Ser Arg Tyr Ala Ser Lys Ile Asn Ile Gly
    450                 455                 460

Ser Lys Val Asn Phe Asp Pro Ile Asp Lys Asn Gln Ile Gln Leu Phe
465                 470                 475                 480

Asn Leu Glu Ser Ser Lys Ile Glu Val Ile Leu Lys Asn Ala Ile Val
                485                 490                 495

Tyr Asn Ser Met Tyr Glu Asn Phe Ser Thr Ser Phe Trp Ile Arg Ile
            500                 505                 510

Pro Lys Tyr Phe Asn Ser Ile Ser Leu Asn Asn Glu Tyr Thr Ile Ile
        515                 520                 525

Asn Cys Met Glu Asn Asn Ser Gly Trp Lys Val Ser Leu Asn Tyr Gly
    530                 535                 540

Glu Ile Ile Trp Thr Leu Gln Asp Thr Gln Glu Ile Lys Gln Arg Val
545                 550                 555                 560

Val Phe Lys Tyr Ser Gln Met Ile Asn Ile Ser Asp Tyr Ile Asn Arg
                565                 570                 575

Trp Ile Phe Val Thr Ile Thr Asn Asn Arg Leu Asn Asn Ser Lys Ile
            580                 585                 590

Tyr Ile Asn Gly Arg Leu Ile Asp Gln Lys Pro Ile Ser Asn Leu Gly
        595                 600                 605

Asn Ile His Ala Ser Asn Asn Ile Met Phe Lys Leu Asp Gly Cys Arg
    610                 615                 620

Asp Thr His Arg Tyr Ile Trp Ile Lys Tyr Phe Asn Leu Phe Asp Lys
625                 630                 635                 640

Glu Leu Asn Glu Lys Glu Ile Lys Asp Leu Tyr Asp Asn Gln Ser Asn
                645                 650                 655

Ser Gly Ile Leu Lys Asp Phe Trp Gly Asp Tyr Leu Gln Tyr Asp Lys
            660                 665                 670

Pro Tyr Tyr Met Leu Asn Leu Tyr Asp Pro Asn Lys Tyr Val Asp Val
        675                 680                 685

Asn Asn Val Gly Ile Arg Gly Tyr Met Tyr Leu Lys Gly Pro Arg Gly
    690                 695                 700

Ser Val Met Thr Thr Asn Ile Tyr Leu Asn Ser Ser Leu Tyr Arg Gly
705                 710                 715                 720

Thr Lys Phe Ile Ile Lys Lys Tyr Ala Ser Gly Asn Lys Asp Asn Ile
                725                 730                 735
```

-continued

```
Val Arg Asn Asn Asp Arg Val Tyr Ile Asn Val Val Lys Asn Lys
        740                 745                 750

Glu Tyr Arg Leu Ala Thr Asn Ala Ser Gln Ala Gly Val Glu Lys Ile
        755                 760                 765

Leu Ser Ala Leu Glu Ile Pro Asp Val Gly Asn Leu Ser Gln Val Val
        770                 775                 780

Val Met Lys Ser Lys Asn Asp Gln Gly Ile Thr Asn Lys Cys Lys Met
785                 790                 795                 800

Asn Leu Gln Asp Asn Asn Gly Asn Asp Ile Gly Phe Ile Gly Phe His
                805                 810                 815

Gln Phe Asn Asn Ile Ala Lys Leu Val Ala Ser Asn Trp Tyr Asn Arg
                820                 825                 830

Gln Ile Glu Arg Ser Ser Arg Thr Leu Gly Cys Ser Trp Glu Phe Ile
                835                 840                 845

Pro Val Asp Asp Gly Trp Gly Glu Arg Pro Leu
    850                 855
```

<210> SEQ ID NO 40
<211> LENGTH: 18
<212> TYPE: PRT
<213> ORGANISM: Artificial Sequence
<220> FEATURE:
<223> OTHER INFORMATION: Peptide fragment (residues 49-66)

<400> SEQUENCE: 40

```
Asp Thr Phe Thr Asn Pro Glu Glu Gly Asp Leu Asn Pro Pro Glu
1               5                   10                  15

Ala Lys
```

<210> SEQ ID NO 41
<211> LENGTH: 18
<212> TYPE: PRT
<213> ORGANISM: Artificial Sequence
<220> FEATURE:
<223> OTHER INFORMATION: Peptide fragment (residues 67-84)

<400> SEQUENCE: 41

```
Gln Val Pro Val Ser Tyr Tyr Asp Ser Thr Tyr Leu Ser Thr Asp Asn
1               5                   10                  15

Glu Lys
```

<210> SEQ ID NO 42
<211> LENGTH: 4
<212> TYPE: PRT
<213> ORGANISM: Artificial Sequence
<220> FEATURE:
<223> OTHER INFORMATION: Peptide fragment (residues 90-93)

<400> SEQUENCE: 42

```
Gly Val Thr Lys
1
```

<210> SEQ ID NO 43
<211> LENGTH: 8
<212> TYPE: PRT
<213> ORGANISM: Artificial Sequence
<220> FEATURE:
<223> OTHER INFORMATION: Peptide fragment (residues 98-105)

<400> SEQUENCE: 43

```
Ile Tyr Ser Thr Asp Leu Gly Arg
1               5
```

```
<210> SEQ ID NO 44
<211> LENGTH: 8
<212> TYPE: PRT
<213> ORGANISM: Artificial Sequence
<220> FEATURE:
<223> OTHER INFORMATION: Peptide fragment (residues 106-113)

<400> SEQUENCE: 44

Met Leu Leu Thr Ser Ile Val Arg
1               5

<210> SEQ ID NO 45
<211> LENGTH: 15
<212> TYPE: PRT
<213> ORGANISM: Artificial Sequence
<220> FEATURE:
<223> OTHER INFORMATION: Peptide fragment (residues 114-128)

<400> SEQUENCE: 45

Gly Ile Pro Phe Trp Gly Gly Ser Thr Ile Asp Thr Glu Leu Lys
1               5                   10                  15

<210> SEQ ID NO 46
<211> LENGTH: 17
<212> TYPE: PRT
<213> ORGANISM: Artificial Sequence
<220> FEATURE:
<223> OTHER INFORMATION: Peptide fragment (residues 129-145)

<400> SEQUENCE: 46

Val Ile Asp Thr Asn Cys Ile Asn Val Ile Gln Pro Asp Gly Ser Tyr
1               5                   10                  15

Arg

<210> SEQ ID NO 47
<211> LENGTH: 21
<212> TYPE: PRT
<213> ORGANISM: Artificial Sequence
<220> FEATURE:
<223> OTHER INFORMATION: Peptide fragment (residues 146-166)

<400> SEQUENCE: 47

Ser Glu Glu Leu Asn Leu Val Ile Ile Gly Pro Ser Ala Asp Ile Ile
1               5                   10                  15

Gln Phe Glu Cys Lys
            20

<210> SEQ ID NO 48
<211> LENGTH: 11
<212> TYPE: PRT
<213> ORGANISM: Artificial Sequence
<220> FEATURE:
<223> OTHER INFORMATION: Peptide fragment (residues 167-177)

<400> SEQUENCE: 48

Ser Phe Gly His Glu Val Leu Asn Leu Thr Arg
1               5                   10

<210> SEQ ID NO 49
<211> LENGTH: 10
<212> TYPE: PRT
<213> ORGANISM: Artificial Sequence
<220> FEATURE:
<223> OTHER INFORMATION: Peptide fragment (residues 178-187)
```

```
<400> SEQUENCE: 49

Asn Gly Tyr Gly Ser Thr Gln Tyr Ile Arg
1               5                   10

<210> SEQ ID NO 50
<211> LENGTH: 25
<212> TYPE: PRT
<213> ORGANISM: Artificial Sequence
<220> FEATURE:
<223> OTHER INFORMATION: Peptide fragment (residues 188-212)

<400> SEQUENCE: 50

Phe Ser Pro Asp Phe Thr Phe Gly Phe Glu Glu Ser Glu Leu Val Asp
1               5                   10                  15

Thr Asn Pro Leu Leu Gly Ala Gly Lys
            20                  25

<210> SEQ ID NO 51
<211> LENGTH: 19
<212> TYPE: PRT
<213> ORGANISM: Artificial Sequence
<220> FEATURE:
<223> OTHER INFORMATION: Peptide fragment (residues 213-231)

<400> SEQUENCE: 51

Phe Ala Thr Asp Pro Ala Val Thr Leu Ala His Glu Leu Ile His Ala
1               5                   10                  15

Gly His Arg

<210> SEQ ID NO 52
<211> LENGTH: 20
<212> TYPE: PRT
<213> ORGANISM: Artificial Sequence
<220> FEATURE:
<223> OTHER INFORMATION: Peptide fragment (residues 245-264)

<400> SEQUENCE: 52

Val Asn Thr Asn Ala Tyr Tyr Glu Met Ser Gly Leu Glu Val Ser Phe
1               5                   10                  15

Glu Glu Leu Arg
            20

<210> SEQ ID NO 53
<211> LENGTH: 8
<212> TYPE: PRT
<213> ORGANISM: Artificial Sequence
<220> FEATURE:
<223> OTHER INFORMATION: Peptide fragment (residues 265-272)

<400> SEQUENCE: 53

Thr Phe Gly Gly His Asp Ala Lys
1               5

<210> SEQ ID NO 54
<211> LENGTH: 11
<212> TYPE: PRT
<213> ORGANISM: Artificial Sequence
<220> FEATURE:
<223> OTHER INFORMATION: Peptide fragment (residues 273-283)

<400> SEQUENCE: 54

Phe Ile Asp Ser Leu Gln Glu Asn Glu Phe Arg
1               5                   10
```

```
<210> SEQ ID NO 55
<211> LENGTH: 8
<212> TYPE: PRT
<213> ORGANISM: Artificial Sequence
<220> FEATURE:
<223> OTHER INFORMATION: Peptide fragment (residues 292-299)

<400> SEQUENCE: 55

Asp Ile Ala Ser Thr Leu Asn Lys
1               5

<210> SEQ ID NO 56
<211> LENGTH: 13
<212> TYPE: PRT
<213> ORGANISM: Artificial Sequence
<220> FEATURE:
<223> OTHER INFORMATION: Peptide fragment (residues 302-314)

<400> SEQUENCE: 56

Ser Ile Val Gly Thr Thr Ala Ser Leu Gln Tyr Met Lys
1               5                   10

<210> SEQ ID NO 57
<211> LENGTH: 10
<212> TYPE: PRT
<213> ORGANISM: Artificial Sequence
<220> FEATURE:
<223> OTHER INFORMATION: Peptide fragment (residues 321-330)

<400> SEQUENCE: 57

Tyr Leu Ser Ser Glu Asp Thr Ser Gly Lys
1               5                   10

<210> SEQ ID NO 58
<211> LENGTH: 5
<212> TYPE: PRT
<213> ORGANISM: Artificial Sequence
<220> FEATURE:
<223> OTHER INFORMATION: Peptide fragment (residues 331-335)

<400> SEQUENCE: 58

Phe Ser Val Asp Lys
1               5

<210> SEQ ID NO 59
<211> LENGTH: 13
<212> TYPE: PRT
<213> ORGANISM: Artificial Sequence
<220> FEATURE:
<223> OTHER INFORMATION: Peptide fragment (residues 344-356)

<400> SEQUENCE: 59

Met Leu Thr Glu Ile Tyr Thr Glu Asp Asn Phe Val Lys
1               5                   10

<210> SEQ ID NO 60
<211> LENGTH: 7
<212> TYPE: PRT
<213> ORGANISM: Artificial Sequence
<220> FEATURE:
<223> OTHER INFORMATION: Peptide fragment (residues 365-371)

<400> SEQUENCE: 60

Thr Tyr Leu Asn Phe Asp Lys
1               5
```

```
<210> SEQ ID NO 61
<211> LENGTH: 12
<212> TYPE: PRT
<213> ORGANISM: Artificial Sequence
<220> FEATURE:
<223> OTHER INFORMATION: Peptide fragment (residues 382-393)

<400> SEQUENCE: 61

Val Asn Tyr Thr Ile Tyr Asp Gly Phe Asn Leu Arg
1               5                   10

<210> SEQ ID NO 62
<211> LENGTH: 22
<212> TYPE: PRT
<213> ORGANISM: Artificial Sequence
<220> FEATURE:
<223> OTHER INFORMATION: Peptide fragment (residues 394-415)

<400> SEQUENCE: 62

Asn Thr Asn Leu Ala Ala Asn Phe Asn Gly Gln Asn Thr Glu Ile Asn
1               5                   10                  15

Asn Met Asn Phe Thr Lys
            20

<210> SEQ ID NO 63
<211> LENGTH: 10
<212> TYPE: PRT
<213> ORGANISM: Artificial Sequence
<220> FEATURE:
<223> OTHER INFORMATION: Peptide fragment (residues 418-427)

<400> SEQUENCE: 63

Asn Phe Thr Gly Leu Phe Glu Phe Tyr Lys
1               5                   10

<210> SEQ ID NO 64
<211> LENGTH: 6
<212> TYPE: PRT
<213> ORGANISM: Artificial Sequence
<220> FEATURE:
<223> OTHER INFORMATION: Peptide fragment (residues 433-438)

<400> SEQUENCE: 64

Gly Ile Ile Thr Ser Lys
1               5

<210> SEQ ID NO 65
<211> LENGTH: 8
<212> TYPE: PRT
<213> ORGANISM: Artificial Sequence
<220> FEATURE:
<223> OTHER INFORMATION: Peptide fragment (residues 1227-1234)

<400> SEQUENCE: 65

Asn Asp Gln Gly Ile Thr Asn Lys
1               5

<210> SEQ ID NO 66
<211> LENGTH: 4
<212> TYPE: PRT
<213> ORGANISM: Artificial Sequence
<220> FEATURE:
<223> OTHER INFORMATION: Peptide fragment (residues 441-444)

<400> SEQUENCE: 66

Ser Leu Asp Lys
1
```

```
<210> SEQ ID NO 67
<211> LENGTH: 21
<212> TYPE: PRT
<213> ORGANISM: Artificial Sequence
<220> FEATURE:
<223> OTHER INFORMATION: Peptide fragment (residues 457-477)

<400> SEQUENCE: 67

Val Asn Asn Trp Asp Leu Phe Phe Ser Pro Ser Glu Asp Asn Phe Thr
1               5                   10                  15

Asn Asp Leu Asn Lys
            20

<210> SEQ ID NO 68
<211> LENGTH: 59
<212> TYPE: PRT
<213> ORGANISM: Artificial Sequence
<220> FEATURE:
<223> OTHER INFORMATION: Peptide fragment (residues 478-536)

<400> SEQUENCE: 68

Gly Glu Glu Ile Thr Ser Asp Thr Asn Ile Glu Ala Ala Glu Glu Asn
1               5                   10                  15

Ile Ser Leu Asp Leu Ile Gln Gln Tyr Tyr Leu Thr Phe Asn Phe Asp
            20                  25                  30

Asn Glu Pro Glu Asn Ile Ser Ile Glu Asn Leu Ser Ser Asp Ile Ile
        35                  40                  45

Gly Gln Leu Glu Leu Met Pro Asn Ile Glu Arg
    50                  55

<210> SEQ ID NO 69
<211> LENGTH: 8
<212> TYPE: PRT
<213> ORGANISM: Artificial Sequence
<220> FEATURE:
<223> OTHER INFORMATION: Peptide fragment (residues 548-555)

<400> SEQUENCE: 69

Tyr Thr Met Phe His Tyr Leu Arg
1               5

<210> SEQ ID NO 70
<211> LENGTH: 20
<212> TYPE: PRT
<213> ORGANISM: Artificial Sequence
<220> FEATURE:
<223> OTHER INFORMATION: Peptide fragment (residues 1205-1224)

<400> SEQUENCE: 70

Ile Leu Ser Ala Leu Glu Ile Pro Asp Val Gly Asn Leu Ser Gln Val
1               5                   10                  15

Val Val Met Lys
            20

<210> SEQ ID NO 71
<211> LENGTH: 16
<212> TYPE: PRT
<213> ORGANISM: Artificial Sequence
<220> FEATURE:
<223> OTHER INFORMATION: Peptide fragment (residues 566-581)

<400> SEQUENCE: 71

Ile Ala Leu Thr Asn Ser Val Asn Glu Ala Leu Leu Asn Pro Ser Arg
1               5                   10                  15
```

```
<210> SEQ ID NO 72
<211> LENGTH: 11
<212> TYPE: PRT
<213> ORGANISM: Artificial Sequence
<220> FEATURE:
<223> OTHER INFORMATION: Peptide fragment (residues 582-592)

<400> SEQUENCE: 72

Val Tyr Thr Phe Phe Ser Ser Asp Tyr Val Lys
1               5                   10

<210> SEQ ID NO 73
<211> LENGTH: 30
<212> TYPE: PRT
<213> ORGANISM: Artificial Sequence
<220> FEATURE:
<223> OTHER INFORMATION: Peptide fragment (residues 597-626)

<400> SEQUENCE: 73

Ala Thr Glu Ala Ala Met Phe Leu Gly Trp Val Glu Gln Leu Val Tyr
1               5                   10                  15

Asp Phe Thr Asp Glu Thr Ser Glu Val Ser Thr Thr Asp Lys
            20                  25                  30

<210> SEQ ID NO 74
<211> LENGTH: 23
<212> TYPE: PRT
<213> ORGANISM: Artificial Sequence
<220> FEATURE:
<223> OTHER INFORMATION: Peptide fragment (residues 627-649)

<400> SEQUENCE: 74

Ile Ala Asp Ile Thr Ile Ile Pro Tyr Ile Gly Pro Ala Leu Asn
1               5                   10                  15

Ile Gly Asn Met Leu Tyr Lys
            20

<210> SEQ ID NO 75
<211> LENGTH: 39
<212> TYPE: PRT
<213> ORGANISM: Artificial Sequence
<220> FEATURE:
<223> OTHER INFORMATION: Peptide fragment (residues 650-688)

<400> SEQUENCE: 75

Asp Asp Phe Val Gly Ala Leu Ile Phe Ser Gly Ala Val Ile Leu Leu
1               5                   10                  15

Glu Phe Ile Pro Glu Ile Ala Ile Pro Val Leu Gly Thr Phe Ala Leu
            20                  25                  30

Val Ser Tyr Ile Ala Asn Lys
        35

<210> SEQ ID NO 76
<211> LENGTH: 13
<212> TYPE: PRT
<213> ORGANISM: Artificial Sequence
<220> FEATURE:
<223> OTHER INFORMATION: Peptide fragment (residues 689-701)

<400> SEQUENCE: 76

Val Leu Thr Val Gln Thr Ile Asp Asn Ala Leu Ser Lys
1               5                   10
```

<210> SEQ ID NO 77
<211> LENGTH: 9
<212> TYPE: PRT
<213> ORGANISM: Artificial Sequence
<220> FEATURE:
<223> OTHER INFORMATION: Peptide fragment (residues 712-720)

<400> SEQUENCE: 77

Tyr Ile Val Thr Asn Trp Leu Ala Lys
1               5

<210> SEQ ID NO 78
<211> LENGTH: 9
<212> TYPE: PRT
<213> ORGANISM: Artificial Sequence
<220> FEATURE:
<223> OTHER INFORMATION: Peptide fragment (residues 721-729)

<400> SEQUENCE: 78

Val Asn Thr Gln Ile Asp Leu Ile Arg
1               5

<210> SEQ ID NO 79
<211> LENGTH: 11
<212> TYPE: PRT
<213> ORGANISM: Artificial Sequence
<220> FEATURE:
<223> OTHER INFORMATION: Peptide fragment (residues 734-744)

<400> SEQUENCE: 79

Glu Ala Leu Glu Asn Gln Ala Glu Ala Thr Lys
1               5                   10

<210> SEQ ID NO 80
<211> LENGTH: 15
<212> TYPE: PRT
<213> ORGANISM: Artificial Sequence
<220> FEATURE:
<223> OTHER INFORMATION: Peptide fragment (residues 745-759)

<400> SEQUENCE: 80

Ala Ile Ile Asn Tyr Gln Tyr Asn Gln Tyr Thr Glu Glu Glu Lys
1               5                   10                  15

<210> SEQ ID NO 81
<211> LENGTH: 13
<212> TYPE: PRT
<213> ORGANISM: Artificial Sequence
<220> FEATURE:
<223> OTHER INFORMATION: Peptide fragment (residues 760-772)

<400> SEQUENCE: 81

Asn Asn Ile Asn Phe Asn Ile Asp Asp Leu Ser Ser Lys
1               5                   10

<210> SEQ ID NO 82
<211> LENGTH: 7
<212> TYPE: PRT
<213> ORGANISM: Artificial Sequence
<220> FEATURE:
<223> OTHER INFORMATION: Peptide fragment (residues 773-779)

<400> SEQUENCE: 82

Leu Asn Glu Ser Ile Asn Lys
1               5

<210> SEQ ID NO 83
<211> LENGTH: 20
<212> TYPE: PRT
<213> ORGANISM: Artificial Sequence
<220> FEATURE:
<223> OTHER INFORMATION: Peptide fragment (residues 787-806)

<400> SEQUENCE: 83

Phe Leu Asn Gln Cys Ser Val Ser Tyr Leu Met Asn Ser Met Ile Pro
1               5                   10                  15

Tyr Gly Val Lys

<210> SEQ ID NO 84
<211> LENGTH: 9
<212> TYPE: PRT
<213> ORGANISM: Artificial Sequence
<220> FEATURE:
<223> OTHER INFORMATION: Peptide fragment (residues 808-816)

<400> SEQUENCE: 84

Leu Glu Asp Phe Asp Ala Ser Leu Lys
1               5

<210> SEQ ID NO 85
<211> LENGTH: 9
<212> TYPE: PRT
<213> ORGANISM: Artificial Sequence
<220> FEATURE:
<223> OTHER INFORMATION: Peptide fragment (residues 828-836)

<400> SEQUENCE: 85

Gly Thr Leu Ile Gly Gln Val Asp Arg
1               5

<210> SEQ ID NO 86
<211> LENGTH: 15
<212> TYPE: PRT
<213> ORGANISM: Artificial Sequence
<220> FEATURE:
<223> OTHER INFORMATION: Peptide fragment (residues 841-855)

<400> SEQUENCE: 86

Val Asn Asn Thr Leu Ser Thr Asp Ile Pro Phe Gln Leu Ser Lys
1               5                   10                  15

<210> SEQ ID NO 87
<211> LENGTH: 10
<212> TYPE: PRT
<213> ORGANISM: Artificial Sequence
<220> FEATURE:
<223> OTHER INFORMATION: Peptide fragment (residues 862-871)

<400> SEQUENCE: 87

Leu Leu Ser Thr Phe Thr Glu Tyr Ile Lys
1               5                   10

<210> SEQ ID NO 88
<211> LENGTH: 11
<212> TYPE: PRT
<213> ORGANISM: Artificial Sequence
<220> FEATURE:
<223> OTHER INFORMATION: Peptide fragment (residues 872-882)

<400> SEQUENCE: 88

Asn Ile Ile Asn Thr Ser Ile Leu Asn Leu Arg
1               5                   10

```
<210> SEQ ID NO 89
<211> LENGTH: 11
<212> TYPE: PRT
<213> ORGANISM: Artificial Sequence
<220> FEATURE:
<223> OTHER INFORMATION: Peptide fragment (residues 883-893)

<400> SEQUENCE: 89

Tyr Glu Ser Asn His Leu Ile Asp Leu Ser Arg
1               5                   10

<210> SEQ ID NO 90
<211> LENGTH: 4
<212> TYPE: PRT
<213> ORGANISM: Artificial Sequence
<220> FEATURE:
<223> OTHER INFORMATION: Peptide fragment (residues 894-897)

<400> SEQUENCE: 90

Tyr Ala Ser Lys
1

<210> SEQ ID NO 91
<211> LENGTH: 6
<212> TYPE: PRT
<213> ORGANISM: Artificial Sequence
<220> FEATURE:
<223> OTHER INFORMATION: Peptide fragment (residues 898-903)

<400> SEQUENCE: 91

Ile Asn Ile Gly Ser Lys
1               5

<210> SEQ ID NO 92
<211> LENGTH: 12
<212> TYPE: PRT
<213> ORGANISM: Artificial Sequence
<220> FEATURE:
<223> OTHER INFORMATION: Peptide fragment (residues 912-923)

<400> SEQUENCE: 92

Asn Gln Ile Gln Leu Phe Asn Leu Glu Ser Ser Lys
1               5                   10

<210> SEQ ID NO 93
<211> LENGTH: 19
<212> TYPE: PRT
<213> ORGANISM: Artificial Sequence
<220> FEATURE:
<223> OTHER INFORMATION: Peptide fragment (residues 930-948)

<400> SEQUENCE: 93

Asn Ala Ile Val Tyr Asn Ser Met Tyr Glu Asn Phe Ser Thr Ser Phe
1               5                   10                  15

Trp Ile Arg

<210> SEQ ID NO 94
<211> LENGTH: 24
<212> TYPE: PRT
<213> ORGANISM: Artificial Sequence
<220> FEATURE:
<223> OTHER INFORMATION: Peptide fragment (residues 952-975)
```

-continued

```
<400> SEQUENCE: 94

Tyr Phe Asn Ser Ile Ser Leu Asn Asn Glu Tyr Thr Ile Ile Asn Cys
1               5                   10                  15
Met Glu Asn Asn Ser Gly Trp Lys
            20

<210> SEQ ID NO 95
<211> LENGTH: 19
<212> TYPE: PRT
<213> ORGANISM: Artificial Sequence
<220> FEATURE:
<223> OTHER INFORMATION: Peptide fragment (residues 976-994)

<400> SEQUENCE: 95

Val Ser Leu Asn Tyr Gly Glu Ile Ile Trp Thr Leu Gln Asp Thr Gln
1               5                   10                  15
Glu Ile Lys

<210> SEQ ID NO 96
<211> LENGTH: 13
<212> TYPE: PRT
<213> ORGANISM: Artificial Sequence
<220> FEATURE:
<223> OTHER INFORMATION: Peptide fragment (residues 1001-1013)

<400> SEQUENCE: 96

Tyr Ser Gln Met Ile Asn Ile Ser Asp Tyr Ile Asn Arg
1               5                   10

<210> SEQ ID NO 97
<211> LENGTH: 10
<212> TYPE: PRT
<213> ORGANISM: Artificial Sequence
<220> FEATURE:
<223> OTHER INFORMATION: Peptide fragment (residues 1014-1023)

<400> SEQUENCE: 97

Trp Ile Phe Val Thr Ile Thr Asn Asn Arg
1               5                   10

<210> SEQ ID NO 98
<211> LENGTH: 5
<212> TYPE: PRT
<213> ORGANISM: Artificial Sequence
<220> FEATURE:
<223> OTHER INFORMATION: Peptide fragment (residues 1024-1028)

<400> SEQUENCE: 98

Leu Asn Asn Ser Lys
1               5

<210> SEQ ID NO 99
<211> LENGTH: 22
<212> TYPE: PRT
<213> ORGANISM: Artificial Sequence
<220> FEATURE:
<223> OTHER INFORMATION: Peptide fragment (residues 1035-1056)

<400> SEQUENCE: 99

Leu Ile Asp Gln Lys Pro Ile Ser Asn Leu Gly Asn Ile His Ala Ser
1               5                   10                  15
Asn Asn Ile Met Phe Lys
            20
```

```
<210> SEQ ID NO 100
<211> LENGTH: 4
<212> TYPE: PRT
<213> ORGANISM: Artificial Sequence
<220> FEATURE:
<223> OTHER INFORMATION: Peptide fragment (residues 1062-1065)

<400> SEQUENCE: 100

Asp Thr His Arg
1

<210> SEQ ID NO 101
<211> LENGTH: 13
<212> TYPE: PRT
<213> ORGANISM: Artificial Sequence
<220> FEATURE:
<223> OTHER INFORMATION: Peptide fragment (residues 1086-1098)

<400> SEQUENCE: 101

Asp Leu Tyr Asp Asn Gln Ser Asn Ser Gly Ile Leu Lys
1               5                   10

<210> SEQ ID NO 102
<211> LENGTH: 16
<212> TYPE: PRT
<213> ORGANISM: Artificial Sequence
<220> FEATURE:
<223> OTHER INFORMATION: Peptide fragment (residues 1141-1156)

<400> SEQUENCE: 102

Gly Ser Val Met Thr Thr Asn Ile Tyr Leu Asn Ser Ser Leu Tyr Arg
1               5                   10                  15

<210> SEQ ID NO 103
<211> LENGTH: 12
<212> TYPE: PRT
<213> ORGANISM: Artificial Sequence
<220> FEATURE:
<223> OTHER INFORMATION: Peptide fragment (residues 1193-1204)

<400> SEQUENCE: 103

Leu Ala Thr Asn Ala Ser Gln Ala Gly Val Glu Lys
1               5                   10

<210> SEQ ID NO 104
<211> LENGTH: 6
<212> TYPE: PRT
<213> ORGANISM: Artificial Sequence
<220> FEATURE:
<223> OTHER INFORMATION: Peptide fragment (residues 1165-1170)

<400> SEQUENCE: 104

Tyr Ala Ser Gly Asn Lys
1               5

<210> SEQ ID NO 105
<211> LENGTH: 20
<212> TYPE: PRT
<213> ORGANISM: Artificial Sequence
<220> FEATURE:
<223> OTHER INFORMATION: Peptide fragment (residues 1277-1296)
```

-continued

```
<400> SEQUENCE: 105

Thr Leu Gly Cys Ser Trp Glu Phe Ile Pro Val Asp Asp Gly Trp Gly
1               5                   10                  15

Glu Arg Pro Leu
            20
```